(12) United States Patent
Elledge et al.

(10) Patent No.: US 6,828,093 B1
(45) Date of Patent: *Dec. 7, 2004

(54) RAPID SUBCLONING USING SITE-SPECIFIC RECOMBINATION

(75) Inventors: Stephen J. Elledge, Houston, TX (US); Qinghua Liu, Houston, TX (US)

(73) Assignee: Baylor College of Medicine, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/122,384

(22) Filed: Jul. 24, 1998

Related U.S. Application Data

(63) Continuation-in-part of application No. 08/864,224, filed on Feb. 28, 1997, now Pat. No. 5,851,808.

(51) Int. Cl.[7] .................................................. C12Q 1/68
(52) U.S. Cl. ........................ 435/6; 435/462; 435/476; 435/477; 435/252.33; 435/196
(58) Field of Search ........................... 435/91.4, 91.41, 435/320.1, 476, 477, 194, 6, 402, 252.33

(56) References Cited

U.S. PATENT DOCUMENTS

| | | |
|---|---|---|
| 4,673,640 A | 6/1987 | Backman |
| 4,683,195 A | 7/1987 | Mullis et al. ............... 435/6 |
| 4,683,202 A | 7/1987 | Mullis ...................... 435/91.2 |
| 4,743,546 A | 5/1988 | Backman et al. |
| 4,959,317 A | 9/1990 | Sauer ........................ 435/462 |
| 4,965,188 A | 10/1990 | Mullis et al. ............... 435/6 |
| 5,093,257 A | 3/1992 | Gray ......................... 435/202 |
| 5,102,797 A | 4/1992 | Tucker et al. .............. 435/473 |
| 5,159,062 A | 10/1992 | Knapp et al. .............. 530/350 |
| 5,227,288 A | 7/1993 | Blattner |
| 5,286,632 A | 2/1994 | Jones |
| 5,334,375 A | 8/1994 | Nabi et al. |
| 5,334,575 A | 8/1994 | Noonan et al. |
| 5,348,886 A | 9/1994 | Lee et al. |
| 5,354,668 A | 10/1994 | Auerbach |
| 5,378,618 A | 1/1995 | Sternberg et al. .......... 435/91.1 |
| 5,434,066 A | 7/1995 | Bebee et al. |
| 5,470,727 A | 11/1995 | Mascarenhas et al. |
| 5,591,609 A | 1/1997 | Auerbach |
| 5,605,793 A | 2/1997 | Stemmer .................... 435/6 |
| 5,614,389 A | 3/1997 | Auerbach |
| 5,635,381 A | 6/1997 | Hooykaas et al. |
| 5,650,308 A | 7/1997 | Baum |
| 5,650,557 A | 7/1997 | Hannah et al. |
| 5,658,772 A | 8/1997 | Odell et al. |
| 5,677,170 A | 10/1997 | Devine et al. |
| 5,677,177 A | 10/1997 | Wahl et al. |
| 5,710,248 A | 1/1998 | Grose |
| 5,723,765 A | 3/1998 | Oliver et al. |
| 5,728,551 A | 3/1998 | Devine et al. |
| 5,733,733 A | 3/1998 | Auerbach |
| 5,733,743 A | 3/1998 | Johnson |
| 5,744,336 A | 4/1998 | Hodges et al. |
| 5,766,891 A | 6/1998 | Shuman |
| 5,776,449 A | 7/1998 | Baum |
| 5,830,707 A | 11/1998 | Bushman |
| 5,837,242 A | 11/1998 | Holliger et al. |
| 5,843,772 A | 12/1998 | Devine et al. |

(List continued on next page.)

FOREIGN PATENT DOCUMENTS

| | | |
|---|---|---|
| CA | 2141412 | 2/1994 |
| EP | 0160571 | 11/1985 |
| EP | 0300422 | 1/1989 |
| WO | WO 90/11375 | 10/1990 |
| WO | WO 91/02801 | 3/1991 |
| WO | WO 91/16427 | 10/1991 |
| WO | 92/15694 | 9/1992 |
| WO | WO 92/20791 | 11/1992 |
| WO | WO 92/22650 | 12/1992 |
| WO | 93/15191 | 8/1993 |
| WO | WO 93/19172 | 9/1993 |
| WO | WO 94/03624 | 2/1994 |
| WO | WO 94/09127 | 4/1994 |
| WO | WO 94/17176 | 8/1994 |
| WO | 94/18333 | 8/1994 |
| WO | WO 95/00555 | 1/1995 |
| WO | 96/30498 | 10/1996 |
| WO | WO 96/40722 | 12/1996 |
| WO | WO 96/40724 | 12/1996 |
| WO | WO 97/06265 | 2/1997 |
| WO | WO 97/09436 | 3/1997 |
| WO | WO 97/25446 | 7/1997 |
| WO | WO 97/32481 | 9/1997 |
| WO | WO 98/10086 | 3/1998 |
| WO | WO 98/53056 | 11/1998 |
| WO | WO 99/25851 | 5/1999 |
| WO | WO 99/55851 | 11/1999 |
| WO | WO 00/12687 | 3/2000 |
| WO | WO 01/05961 | 1/2001 |
| WO | WO 01/07572 A3 | 2/2001 |
| WO | WO 01/07572 A2 | 2/2001 |
| WO | WO 01/11058 | 2/2001 |

OTHER PUBLICATIONS

Written Record of Telephonic Interviews dated Jun. 27, 2003.

(List continued on next page.)

*Primary Examiner*—James Ketter
(74) *Attorney, Agent, or Firm*—Vinson & Elkins L.L.P.

(57) ABSTRACT

The present invention provides compositions, including vectors, and methods for the rapid subcloning of nucleic acid sequences in vivo and in vitro. In particular, the invention provides vectors used to contain a gene of interest that comprise a sequence-specific recombinase target site. These vectors are used to rapidly transfer the gene or genes of interest into any vector that contains a sequence-specific recombinase target site located downstream of a regulatory element so that the gene of interest may be regulated.

26 Claims, 35 Drawing Sheets

U.S. PATENT DOCUMENTS

| | | | | |
|---|---|---|---|---|
| 5,851,808 | A | * 12/1998 | Elledge et al. | 435/91.4 |
| 5,858,657 | A | 1/1999 | Winter et al. | |
| 5,871,907 | A | 2/1999 | Winter et al. | |
| 5,874,259 | A | 2/1999 | Szybalski | |
| 5,888,732 | A | 3/1999 | Hartley et al. | 435/6 |
| 5,916,804 | A | 6/1999 | Bushman | |
| 5,919,676 | A | 7/1999 | Graham et al. | |
| 5,928,914 | A | 7/1999 | Leboulch et al. | |
| 5,981,177 | A | 11/1999 | Demirjian et al. | 435/6 |
| 5,989,872 | A | 11/1999 | Luo et al. | 435/91.2 |
| 6,010,884 | A | 1/2000 | Griffiths et al. | 435/69.7 |
| 6,040,430 | A | 3/2000 | Stewart | 530/358 |
| 6,063,627 | A | 5/2000 | McVey et al. | 435/440 |
| 6,080,576 | A | 6/2000 | Zambrowicz et al. | 435/320.1 |
| 6,143,557 | A | 11/2000 | Hartley et al. | 435/320.1 |
| 6,171,861 | B1 | 1/2001 | Hartley et al. | |
| 6,262,341 | B1 | 7/2001 | Baszczynski et al. | 800/278 |
| 6,271,436 | B1 | 8/2001 | Piedrahita et al. | 800/21 |
| 6,361,972 | B1 | 3/2002 | Harrington et al. | 435/69.1 |
| 6,410,266 | B1 | 6/2002 | Harrington et al. | 435/69.1 |
| 6,410,317 | B1 | 6/2002 | Farmer | 435/320.1 |
| 6,436,707 | B1 | 8/2002 | Zambrowicz et al. | 435/455 |

OTHER PUBLICATIONS

Bauer, et al., "Extent of Sequence Homology Required for Bacteriophage Lamba Site–specific Recombination," J. Mol. Biol. 181:187–97, 1985.

Cherepanov and Wackernagel, "Gene disruption in *Escherichia coli:* TcR and KmR cassettes with the option of Flp–catalyzed excision of the antibiotic–resistance determinant," Gene, 158:9–14, 1995.

Colls and Hall, "Expression of Antibiotic Resistance Genes in the Integrated Cassettes of Integrons," Antimicrobial Agents and Chemotherapy, 39(1):155–62, 1995.

Backman et al., "Use of synchronous site–specific recombination in vivo to regulate gene expression," *Bio/Technology*, 1045–49, 1984.

Bernard et al., "The F plasmid CcdB protein induces efficient ATP–dependent DNA cleavage by gyrase," *J. Mol. Biol.*, 234:534–41, 1993.

Curcio et al., "Single–step selection for Ty1 element retrotransposition," *Proc. Natl. Acad. Sci. USA*, 88:936–40, 1991.

Francia et al., "The IntI1 integron integrase preferentially binds single–stranded DNA of the attC site," *Journal of Bacteriology*, 181:21, 6844–49, 1999.

Guo et al., "Asymmetric DNA bending in the Cre–loxP site–specific recombination synapse," *Proc. Natl. acad. Sci. USA*, 96:7143–48, 1999.

Hehl et al., "Structural analysis of Tam3, a transposable element from *Antirrhinum majus*, reveals homologies to the Ac element from maize," *Plant Molecular Biology*, 16:369–71, 1991.

Iida et al., "A site–specific, conservative recombination system carried by bacteriophage P1. mapping the recombinase gene cin and the cross–over sites cix for the inversion of the C segment," *The EMBO Journal*, 1:11, 1445–53, 1982.

Kim et al., "Lambda int protein bridges between higher order complexes at two distant chromosomal loci attL and attR," *Science*, 256:198–203, 1992.

Lorbach et al., "Site–specific recombination in human cells catalyzed by Phage λ integrase mutants," *J. Mol. Biol.*, 296:1175–81, 2000.

Nagy, "Cre recombinase: the universal reagent for genome tailoring," *genesis*, 26:99–109, 2000.

Sauer, "Inducible gene targeting in mice using the Cre/lox system," *METHODS: A Companion to Methods in Enzymology*, 14:381–92, 1998.

Segall et al., "Architectural elements in nucleoprotein complexes: interchangeability of specific and non–specific DNA binding proteins," *The EMBO Journal*, 13:19, 4536–48, 1994.

Sheffield et al., "Overcoming expression and purification problems of RhoGDI using a family of "Parallel" expression vectors," *Protein Expression and Purification*, 15:34–39, 1999.

Simpson et al., "Systematic subcellular localization of novel proteins identified by large–scale cDNA sequencing," *EMBO Reports*, 1:3, 287–92, 2000.

Voziyanov et al., "A general model for site–specific recombination by the integrase family recombinases," *Nucleic Acids Research*, 27:4, 930–41, 1999.

Wild et al., "Targeting and retrofitting pre–existing libraries of transposon insertions with FRT and oriV elements for in–vivo generation of large quantities of any genomic fragment," *Gene*, 223, 55–66, 1998.

Yoon et al., "Cre/loxP–mediated in vivo excision of large segments from yeast genome and their amplification based on the 2 $\mu$m plasmid–derived system," *Gene*, 223:67–76, 1998.

Zahra et al., "Selectable in–vivo recombination to increase antibody library size—an improved phage display vector system," *Gene*, 227:49–54, 1999.

Zhang et al., "A new logic for DNA engineering using recombination in *Escherichia coli*," *nature genetics*, 20:123–128, 1998.

Abremski and Gottesman, "Purification of the Bacteriophage λ xis Gene Product Required for λ Excisive Recombination", The Journal of Biological Chemistry, 257(16)9658–62, 1982.

Abremski and Hoess, "Bacteriophage P1 Site–specific Recombination", The Journal of Biological Chemistry, 259(3):1509–14, 1984.

Abremski, et al., "Bacteriophage P1 Cre–LoxP Site–specific Recombination", The Journal of Biological Chemistry, 261(1):391–96, 1986.

Adams, et al., "Cre–lox Recombination in *Escherichia coli* Cells", J. Mol. Biol., 226(3):661–73, 1992.

Andrews, et al., "The FLP Recombinase of the $2\mu$ Circle DNA of Yeast: Interaction with Its Target Sequences", CELL, 40(4):795–803, 1985.

Andrews, et al., "Interaction of the FLP Recombinase of the *Saccharmoyces cerevisiae* $2\mu$m Plasmid with Mutated Target Sequences", Molecular and Cellular Biology, 6(7):2482–89, 1986.

Anton and Graham, "Site–Specific Recombination Mediated by an Adenovirus Vector Expressing the Cre Recombinase Protein: A Molecular Switch for Control of Gene Expression", Journal of Virology, 69(8):4600–06, 1995.

Araki, et al., "Site–specific Recombinase, R, Encoded by Yeast Plasmid pSR1", J. Mol. Biol, 225:25–37, 1992.

Argos, et al, "The integrase family of site–specific recombinases: regional similarities and global diversity", The EMBO Journal, 5(2):433–440, 1986.

Astumian, et al., "Site–Specific Recombination between Cloned attP and attB Sites from the *Haemophilus influenzae* Bacteriophase HP1 Propagated in Recombination–Deficient *Escherichia coli*", Journal of Bacteriology, 171(3):1747–1750, 1989.

Atlung, et al., "A versatile method for integration of genes and gene fusions into the λ attachment site of *Escherichia coli*", GENE, 107:11–17, 1991.

Ausubel, et al., "Current Protocols in Molecular Biology", Supplement 26, Boston, MA: John Wiley & Sons, Inc. (1995).

Ausubel, et al., "Current Protocols in Molecular Biology", Supplement 15, Boston, MA: John Wiley & Sons, Inc. (1995).

Balakrishnan, et al., "A gene cassette for adapting *Escherichia coli* strains as hosts for att–Int–mediated rearrangement and $p_L$ expression vectors", GENE, 138:101–04, 1994.

Bayley, et al., "Exchange of gene activity in transgenic plants catalyzed by the Cre–lox site–specific recombination system", Plant Molecular Biology, 18:353–361, 1992.

Bethke and Sauer, "Segmental genomic replacement by Cre–mediated recombination: genotoxic stress activation of the p53 promoter in single–copy transformants", Nucleic Acids Research, 25(14):2828–34, 1997.

Bernard and Couturier, "Cell Killing by the F Plasmid CcdB Protein Involves Poisoning of DNA–Topisomerase II Complexes", J. Mol. Biol., 226:735–45, 1992.

Bernard, et al., "Positive–selection vectors using the F plasmid ccdB killer gene", GENE, 148:71–74, 1994.

Betz, et al., "Bypass of lethality with mosaic mice generated by Cre–loxP–mediated recombination", Current Biology, 6(10):1307–16, 1996.

Bhandari and Gowrishankar, "An *Escherichia coli* Host Strain Useful for Efficient Overproduction of Cloned Gene Products with NaCl as the Inducer", Journal of Bacteriology, 179(13):4403–06, 1997.

Black, "In vitro packaging into phage T4 particles and specific recirculatization of phase lambda DNAs", GENE, 46:97–101, 1986.

Bloch, et al., "Purification of *Escherichia coli* Chromosomal Segments without Cloning", Biochemical and Biophysical Research Communications, 223(1):104–11, 1996.

Bochner, et al., "Positive Selection for Loss of Tetracycline Resistance", Journal of Bacteriology, 143(2):926–33, 1980.

Boyd, "Turbo cloning: a fast, efficient method for cloning PCR products and other blunt–ended DNA fragments into plasmids", Nucleic Acids Research, 21(4):817–21, 1993.

Broach, et al., "Recombination within the Yeast Plasmid 2μ Circle is Site–Specific", CELL, 29:227–34, 1982.

Brunelli and Pall, "A Series of Yeast/ *Escherichia coli* λ Expression Vectors Designed for Directional Cloning of cDNAs and cre / lox–Mediated Plasmid Excision", YEAST, 9:1309–18, 1993.

Bubeck, et al., "Rapid cloning by homologous recombination in vivo", Nucleic Acids Research, 21(15):3601–02, 1993.

Buchholz, et al., "A simple assay to determine the functionality of Cre or FLP recombination targets in genomic manipulation constructs", Nucleic Acids Research, 24(15):3118–19, 1996.

Buchholz, et al., "Different thermostabilities of FLP and Cre recombinases: implications for applied site–specific recombination", Nucleic Acids Research, 24(21):4256–62, 1996.

Burioni, et al., "An improved phage display vector for antibody repertoire cloning by construction for combinatorial libraries", Res. Virol., 148:161–64, 1997.

Bushman, et al., "Control of Directionality in Lambda Site Specific Recombination", SCIENCE, 230(4728):906–11, 1985.

Campbell, "Chromosomal Insertion Sites for Phages and Plasmids", Journal of Bacteriology, 174(23):7495–99, 1992.

Capone, "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells", Molecular and Cellular Biology, 6(9):3059–67, 1986.

Chanock, "Human Monoclonal Antibody Fab Fragments Cloned from Combinatorial Libraries: Potential Usefulness in Prevention and/or Treatment of Major Human Viral Diseases", Infectious Agents and Disease, 2(3):118–31, 1993.

Chapin, et al., "Differential Expression of Alternatively Spliced Forms of MAP4; A repertoire of Structurally Different Microtubule–Binding Domains", BIOCHEMISTRY, 34(7):2289–2301, 1995.

Chatterjee and Coren, "Isolating large nested deletions in bacterial and P1 artificial chromosomes by in vivo P1 packaging of products of Cre–catalysed recombination between the endogenous and a transposed loxP site", Nucleic Acids Research, 25(11):2205–12, 1997.

Chong, et al., "Single–column purification of free recombinant proteins using a self–cleavable affinity tag derived from a protein splicing element", GENE, 192:271–81, 1997.

Cox, "The FLP protein of the yeast 2–μm plasmid: Expression of a eukaryotic genetic recombination system in *Escherichia coli*", Proc. Natl. Acad. Sci. USA, 80(14):4223–27, 1983.

Craig and Nash, "The Mechanism of Phage λ Site–Specific Recombination: Site–Specific Breakage of DNA by Int Topoisomerase", CELL, 35(3):795–803, 1983.

Dale and Ow, "Intra– and intermolecular site–specific recombination in plant cells mediated by bacteriophage P1 recombinase", GENE, 91:79–85, 1990.

Dale and Ow, "Gene transfer with subsequent removal of the selection gene from the host genome", Proc. Natl. Acad. Sci. USA, 88:10558–62, 1991.

Dang and Perrimon, "Use of a Yeast Site–Specific Recombinase to Generate Embryonic Mosaics in *Drosophila*", Developmental Genetics, 13:367–75, 1992.

Davis, et al., "Analysis of the Mechanisms of Action of the *Saccharomyces cerevisiae* Dominant Lethal cdc42$^{G12V}$ and Dominant Negative cdc42$^{D118A}$ Mutations", The Journal of Biological Chemistry, 273(2):849–58, 1998.

Degryse, "In vivo intermolecular recombination in *Escherichia coli:* application to plasmid constructions", GENE, 170(1):45–50, 1996.

Derbyshire and Belfort, "Lightning strikes twice: Intron–intein coincidence", Proc. Natl. Acad. Sci. USA, 95:1356–57, 1998.

Devine and Boeke, Efficient integration of artificial transposons into plasmid targets in vitro: a useful tool for DNA mapping, sequencing and genetic analysis, Nucleic Acids Research, 22(18):3765–72, 1994.

Diederich, et al., "New Cloning Vectors for Integration into the λ Attachment Site attB of the *Escherichia coli* Chromosome", PLASMID, 28:14–24, 1992.

Dymecki, "A modular set of Flp, FRT and LacZ fusion vectors for manipulating genes by site–specific recombination", Gene, 171(2):197–201, 1996.

Esposito and Scocca, "The integrase family of tyrosine recombinases: evolution of a conserved active site domain", Nucleic Acids Research, 25(18):3605–14, 1997.

Feil, et al., "Regulation of Cre Recombinase Activity by Mutated Estrogen Receptor Ligand–Binding Domains", Biochemical and Biophysical Research Communications, 237(3):752–57, 1997.

Ferguson, et al., "Construction and characterization of three yeast–Escherichia coli shuttle vectors designed for rapid subcloning of yeast genes on small DNA fragments", GENE, 16:191–97, 1981.

Fiering, et al., "An 'in–out' strategy using gene targeting and FLP recombinase for the functional dissection of complex DNA regulatory elements: Analysis of the β–globin locus control region", Proc. Natl. Acad. Sci. USA, 90:8469–73, 1993.

Filutowicz, et al., "Purification of the Escherichia coli integration host factor (IHF) in one chromatographic step", GENE, 147:149–50, 1994.

Fukushige and Sauer, "Genomic targeting with a positive–selection lox integration vector allows highly reproducible gene expression in mammalian cells", Proc. Natl. Acad. Sci. USA, 89:7905–09, 1992.

Gage, et al., "A Cell–Free Recombination System for Site–Specific Integration of Multigenic Shuttle Plasmids into the Herpes Simplex Virus Type 1 Genome", Journal of Virology, 66(9):5509–15, 1992.

Geoffroy, et al., "A new phage display system to construct multicombinatorial libraries of very large antibody repertoires", GENE, 151:109–13, 1994.

Golic and Lindquist, "The FLP Recombinase of Yeast Catalyzes Site–Specific Recombination in the Drosophila Genome", CELL, 59:499–509, 1989.

Gotz, et al., "Escherichia coli 30S mutants lackgin protein S20 are defective in translation initiation", Biochimica et Biophysica Acta, 1050:93–97, 1990.

Green and Noller, "Ribosomes and Translation", Annu. Rev. Biochem 1997, 66:679–716, 1997.

Gu, et al., "Deletion of a DNA Polymerase β Gene Segment in T Cells Using Cell Type–Specific Gene Targeting", SCIENCE, 265:103–106, 1994.

Hardy, et al., "Construction of Adenovirus Vectors through Cre–lox Recombination", Journal of Virology, 71(3):1842–49, 1997.

Hasan and Szybalski, "Control of cloned gene expression by promoter inversion in vivo: construction if improved vectors with a multiple cloning site and the $p_{tac}$ promoter", GENE, 56:145–51, 1987.

Hashimoto–Gotoh, et al., "Improved vector, pHSG664, for direct streptomycin–resistance selection: cDNA cloning with G: C–tailing procedure and subcloning of double–digest DNA fragments", GENE, 41:125–28, 1986.

Hoekstra, et al., "Shuttle Mutagenesis: Bacterial Transposons for Genetic Manipulations in Yeast", Methods in Enzymology, 194:329–42, 1991.

Hoess and Abremski, "The Cre–lox Recombination System", Nucleic Acids and Molecular Biology, Eckstein, Lilley, eds., 4:98–109, 1990.

Hoogenboom, et al., "Multi–subunit proteins on the surface of filamentous phase: methodologies for displaying antibody (Fab) heavy and light chains", Nucleic Acids Research, 19(15):4133–37, 1991.

Jaffe, et al., Effects of the ccd Function of the F Plasmid on Bacterial Growth, Journal of Bacteriology, 163(3):841–49, 1985.

Jayaram, "The Int family of site–specific recombinases: Some thoughts on a general reaction mechanism", J. Genet., 67(1):29–36, 1988.

Jeong, et al., "Cloning and nucleotide sequencing of the genes, rplU and rpmA, for ribosomal proteins L21 and L27 of Escherichia coli", J.DNA Sequencing and Mapping, 4(1):59–67, 1993.

Kanaar, et al., "Gin–Mediated Recombination of Catenated and Knotted DNA Substrates: Implications for the Mechanism of Interaction Between Cis–Acting Sites", CELL, 58:147–59, 1989.

Katz, et al., "Site–specific recombination in Escherichia coli between the att sites of plasmid pSE211 from Saccharopolyspora erythraea", Mol. Gen. Genet., 227:155–59, 1991.

Kealey, et al., "Production of a polyketide natural product in nonpolyketide–producing prokaryotic and eukarytotic hosts", Proc. Natl. Acad. Sci. USA, 95:505–09, 1998.

Kholodenko, et al., "Metabolic Design: How to Engineer a Living Cell to Desired Metabolite Concentrations and Fluxes", Biotechnology and Bioengineering, 59(2):239–47, 1998.

Kilby, et al., "Site–specific recombinases: tools for genome engineering", Trends in Genetics, 9(12):413–21, 1993.

Kim and Landy, "Lambda Int Protein Bridges Between Higher Order Complexes at Two Distant Chromosomal Loci attL and attR", SCIENCE, 256:198–203, 1992.

Kitts and Nash, "Bacteriophage Lambda Site–specific Recombination Proceeds with a Defined Order of Strand Exchanges", J. Mol. Biol., 204(1):95–107, 1988.

Kouprina, et al., "Rescue of Targeted Regions of Mammalian chromosomes by in Vivo Recombination in Yeast", Genome Research, 8:666–72, 1998.

Kozak, "Comparison of Initiation of Protein Synthesis in Procaryotes, Eucaryotes, and Organelles", Microbiological Reviews, 47(1):1–45, 1983.

Kozak, "An analysis of 5'–noncoding sequences from 699 vertebrate messenger RNAs", Nucleic Acids Research, 15(20):8125–49, 1987.

Kozak, "Structural Features in Eukaryotic mRNAs That Modulate the Initiation of Translation", The Journal of Biological Chemistry, 266(30):19867–70, 1991.

Kuhn, et al., "Inducible Gene Targeting in Mice", SCIENCE, 269:1427–29, 1995.

Lafontaine and Tollervey, "One–step PCR mediated strategy for the construction of conditionally expressed and epitope tagged yeast proteins", Nucleic Acids Research, 24(17):3469–72, 1996.

Lake, "Evolving Ribosome Structure: Domains in Archaebacteria, Eubacteria, Eocytes and Eukaryotes", Ann. Rev. Biochem. 1985, 54:507–30, 1985.

Lakso, et al., "Targeted oncogene activation by site–specific recombination in transgenic mice", Proc. Natl. Acad. Sci. USA, 89:6232–36, 1992.

Lander, "The New Genomics: Global Views of Biology", SCIENCE, 274:536–39, 1996.

Landy, "Dynamic, Structural, and Regulatory Aspects of λ Site–Specific Recombination", Annu. Rev. Biochem., 58:913–49, 1989.

Landy, "Mechanistic and structural complexity in the site–specific recombination pathways of Int and FLP", Current Opinion in Genetics and Development, 3:699–707, 1993.

Lebreton, et al., "Mutations That Improve the Binding of Yeast FLP Recombinase to Its Substrate", GENETICS, 118:393–400, 1988.

Lee, et al., "Genetic Analysis of *Escherichia coli* Integration Host Factor Interactions with Its Bacteriophage λ H' Recognition Site", Journal of Bacteriology, 173(2):609–17, 1991.

Leong, et al., "Generation of single base–pair deletions, insertions, and substitutions by a site–specific recombination system", Proc. Natl. Acad. Sci. USA, 82:6990–94, 1985.

Leung, "Application of Combinatrial Libraries and Protein Engineering to the Discovery of Novel Anti–Thrombotic Drugs", Journal of the International Society of Thrombosis and Haemostasis, 74(1):373–76, 1995.

Luckow, et al., "Efficient Generation of Infectious Recombinant Baculoviruses by Site–Specific Transposon–Mediated Insertion of Foreign Genes into a Baculovirus Genome Propataged in *Escherichia coli*", Journal of Virology, 67(8):4566–79, 1993.

Mackie, "Nucleotide Sequence of the Gene for Ribosomal Protein S20 and Its Flanking Regions", The Journal of Biological Chemistry, 256(15):8177–82, 1981.

Maeser and Kahmann, "The Gin recombinase of phage Mu can catalyse site–specific recombination in plant protoplasts", Mol. Gen. Genet., 230:170–76, 1991.

Mahillon, et al., "IS231 and other *Bacillus thuringiensis* transposable elements: a review", GENETICA, 93:13–26, 1994.

Mahillon, et al., "Subdivision of the *Escherichia coli* K–12 genome for sequencing: manipulation and DNA sequence of transposable elements introducing unique restriction sites", GENE, 223:47–54, 1998.

Matsuzaki, et al., "Chromosome Engineering in *Saccharomyces cerevisiae* by Using a Site–Specific Recombination System of a Yeast Plasmid", Journal of Bacteriology, 172(2):610–18, 1990.

McCarthy and Brimacombe, "Prokaryotic translation: the interactive pathway leading to initiation", Trends in Genetics, 10(11):402–07, 1994.

Medberry, et al., "Intra–chromosomal rearrangements generated by Cre–lox site–specific recombination", Nucleic Acids Research, 23(3):485–90, 1995.

Miki, et al., "Control of Segregation of Chromosomal DNA by Sex Factor F in *Escherichia coli*", J. Mol. Biol., 225(1):39–52, 1992.

Mizuuchi and Mizuuchi, "Integrative Recombination of Bacteriophage λ: In Vitro Study of the Intermolecular Reaction", Cold Spring Harbor Symposia on Quantitive Biology, XLIII:1111–14, 1979.

Mizuuchi and Mizuuchi, "The extent of DNA sequence required for a functional bacterial attachment site of phage lambda", Nucleic Acids Research, 13(4):1193–1208, 1985.

Mozo and Hooykaas, "Design of a novel system for the construction of vectors for Agrobacterium–mediated plant transformation", Mol. Gen. Genet., 236:1–7, 1992.

Mullins, et al., "Efficient Cre–lox linearisation of BACs: applications to physical mapping and generation of transgenic animals", Nucleic Acids Research, 25(12):2539–40, 1997.

Nagaraja and Weisberg, "Specificity Determinants in the Attachment Sites of Bacteriophages HK022 and λ", Journal of Bacteriology, 172:6540–50, 1990.

Nash, "Integrative Recombination of Bacteriophage Lambda DNA In Vitro", Proc. Natl. Acad. Sci. USA, 72(3):1072–76, 1975.

Nash, "Purification and Properties of the Bacteriophage Lambda Int Protein", Methods in Enzymology, 100:210–16, 1983.

Nash, "Bending and supercoiling of DNA at the attachment site of bacteriophage λ", Trends in Biochemical Sciences, 15: 222–27, 1990.

Nash and Robertson, "Purification and Properties of the *Escherichia coli* Protein Factor Required for λ Integrative Recombination", The Journal of Biological Chemistry, 256(17):9246–53, 1981.

Nash and Robertson, "Heteroduplex substrates for bacteriophage lambda site–specific recombination: cleavage and strand transfer products", The EMBO Journal, 8(11):3523–33, 1989.

Nash, et al., "Role of homology in site–specific recombination of bacteriophage λ: Evidence against joining of cohesive ends", Proc. Natl. Acad. Sci. USA, 84(12):4049–53, 1987.

Nomura, et al., "Regulation of the Synthesis of Ribosomes and Ribosomal Components", Ann. Rev. Biochem. 1984, 53:75–117, 1984.

Numrych, et al., "A comparison of the effects of single–base and triple–base changes in the integrase arm–type binding sites on the site–specific recombination of bacteriophage lambda", Nucleic Acids Research, 18(13):3953–59, 1990.

Numrych, et al., "Characterization of the bacteriophage lambda excisionase (Xis) protein: the C–terminus is required for Xis–integrase cooperativity but not for DNA binding", The EMBO Journal, 11(10):3797–3806, 1992.

Nunes–Duby, et al., "Half–att Site Substrates Reveal the Homology Independence and Minimal Protein Requirements for Productive Synapsis in λ Excisive Recombination", CELL, 59:197–206, 1989.

Nunes–Duby, et al., "Similarities and differences among 105 members of the Int family of site–specific recombinases", Nucleic Acids Research, 26(2):391–406, 1998.

Oberto, et al., "A segment of the phage HK022 chromosome is a mosaic of other lambdoid chromosomes", Nucleic Acids Research, 22(3):354–56, 1994.

O'Gara, et al., "Identification and Molecular Genetic Analysis of Multiple Loci Contributing to High–Level Tellurite Resistance in *Rhodobacter sphaeroides* 2.4.1", Applied and Environmental Microbiology, 63(12):4713–20, 1997.

Oliner, et al., "In vivo cloning of PCR products in *E coli*", Nucleic Acids Research, 21(22):5192–97, 1993.

Orban, et al., "Tissue– and site–specific DNA recombination in transgenic mice", Proc. Natl. Acad. Sci. USA, 89(15):6861–65, 1992.

Osborne, et al., "A system for insertional mutagenesis and chromosomal rearrnagement using the Ds transposon and Cre–lox", The Plant Journal, 7(4):687–701, 1995.

Padgett and Sorge, "Creating seamless junctions independent of restriction sites in PCR cloning", GENE, 168:31–35, 1996.

Pan, et al., "Ligation of Synthetic Activated DNA Substrates by Site–Specific Recombinases and Topoisomerase I", The Journal of Biological Chemistry, 268(5):3683–89, 1992.

Panke, et al., "Engineering of Quasi–Natural *Pseudomonas putida* Strains for Toluene Metabolism through an ortho–Cleavage Degradation Pathway", Applied and Environmental Microbiology, 64(2):748–51, 1998.

Parks and Graham, "A Helper–Dependent System for Adenovirus Vector Production Helps Define a Lower Limit for Efficient DNA Packaging", Journal of Virology, 71(4):3293–98, 1997.

Peakman, et al., "Highly efficient generation of recombinant baculoviruses by enzymatically mediated site–specific in vitro recombination", Nucleic Acids Research, 20(3):495–500, 1992.

Peredelchuk and Bennett, "A method for construction of *E. coli* strains with multiple DNA insertions in the chromosome", GENE, 187:231–38, 1997.

Persson, "Combinatorial Libraries", Intern. Rev. Immunol., 10(2–3):153–63, 1993.

Phillips–Jones, et al., "Context Effects on Misreading and Suppression at UAG Codons in Human Cells", Molecular and Cellular Biology, 15(12):6593–6600, 1995.

Pichel, et al., "Timing of SV40 oncogene activation by site–specific recombination determines subsequent tumor progression during murine lens development", ONCOGENE, 8:3333–42, 1993.

Pierce, et al., "A positive selection vector for cloning high molecular weight DNA by the Bacteriophage P1 system: Improved cloning efficacy", Proc. Natl. Acad. Sci. USA, 89:2056–60, 1992.

Podhajska, et al., "Control of cloned gene expression by promoter inversion in vivo: construction of the heat-–pulse–activated att–nutL–p–att–N module", GENE, 40:163–68, 1985.

Posfai, et al., "In vivo excision and amplification of large segments of the *Escherichia coli* genome", Nucleic Acids Research, 22(12):2392–98, 1994.

Powell, "Enhanced concatemer cloning—a modification to the SAGE (Serial Analysis of Gene Expression) technique", Nucleic Acids Research, 26(14):3445–46, 1998.

Prasad, et al., "Substrate Recognition by the $2\mu$m Circle Site–Specific Recombinase: Effect of Mutations within the Symmetry Elements of the Minimal Substrate", Molecular and Cellular Biology, 6(12):4329–34, 1986.

Prieto, et al., "Molecular Characterization of the 4–Hydroxyphenylacetate Catabolic Pathway of *Escherichia coli* W: Engineering a Mobile Aromatic Degradative Cluster", Journal of Bacteriology, 178(1):111–20, 1996.

Qian, et al., "Reactions between Half– and Full–FLP Recombination Target Sites", The Journal of Biological Chemistry, 267(11):7794–7805, 1992.

Reed and Grindley, "Transposon–Mediated Site–Specific Recombination in Vitro: DNA Cleavage and Protein–DNA Linkage at the Recombination Site", CELL, 25:721–728, 1981.

Richet, et al., "The Interaction of Recombination Proteins with Supercoiled DNA: Defining the Role of Supercoiling in Lambda Integrative Recombination", CELL, 46:1011–21, 1986.

Richet, et al., "Synapsis of the Attachment Sites during Lambda Integrative Recombination Involves Capture of a Naked DNA by a Protein–DNA Complex", CELL, 52:9–17, 1988.

Ross and Landy, "Patterns of $\lambda$ Int Recognition in the Regions of Strand Exchange", CELL, 33:261–72, 1983.

Sadowski, "Site–Specific Recombinases: Changing Partners and Doing the Twist", Journal of Bacteriology, 165(2):341–47, 1986.

Sadowski, "The Flp Recombinase of the $2-\mu$m Plasmid of *Saccharomyces cerevisiae*", Progress in Nucleic Acid Research and Molecular Biology, 51:53–91, 1995.

Sandhu, "Protein Engineering of Antibodies", Critical Reviews in Biotechnology, 12(5/6):437–62, 1992.

Sauer, "Manipulation of Transgenes by Site–Specific Recombination: Use of Cre Recombinase", Methods in Enzymology, 225:890–900, 1993.

Sauer, "Site–specific recombination: developments and applications", Current Opinion in Biology, 5:521–27, 1994.

Sauer, "Multiplex Cre/lox recombination permits selective site–specific DNA targeting to both a natural and an engineered site in the yeast genome", Nucleic Acids Research, 24(23):4608–13, 1996.

Sauer, "Inducible Gene Targeting in Mice Using the Cre/lox System", Methods: A Companion to Methods in Enzymology, 14(4):381–92, 1998.

Sauer and Henderson, "The cyclization of linear DNA in *Escherichia coli* by site–specific recombination", GENE, 70:331–341, 1988.

Sauer and Henderson, "Cre–stimulated recombination at loxP–containing DNA sequences placed into the mammalian genome", Nucleic Acids Research, 17(1):147–61, 1989.

Sauer, et al., "Site–specific insertion of DNA into a pseudorabies virus vector", Proc. Natl. Acad. Sci. USA, 84:9108–12, 1987.

Schindelhauer and Cooke, "Efficient combination of large DNA in vitro: in gel specific recombination (IGSSR) of PAC fragments containing $\alpha$ satellite DNA and the human HPRT gene locus", Nucleic Acids Research, 25(11):2241–43, 1997.

Schlake and Bode, "Use of Mutated FLP Recognition Target (FRT) Sites for the Exchange of Expression Cassettes at Defined Chromosomal Loci", BIOCHEMISTRY, 33:12746–51, 1994.

Segall and Nash, "Synaptic intermediates in bacteriophage lambda site–specific recombination: integrase can align pairs of attachment sites", The EMBO Journal, 12(12):4567–76, 1993.

Segall and Nash, "Architectural flexibility in lambda site–specific recombination: three alternate conformations channel the attL site into three distinct pathways", Genes to Cells, 1:453–63, 1996.

Senecoff, et al., "DNA Recognition by the FLP Recombinase of the Yeast $2\mu$ plasmid", J. Mol. Biol, 201(2):405–21, 1988.

Shuman, "Recombination mediated by vaccinia virus DNA topoisomerase I in *Escherichia coli* is sequence specific", Proc. Natl. Acad. Sci. USA, 88:10104–08, 1991.

Sizemore, et al., "Quantitative analysis of the Tn10 Tet repressor binding to a complete set of tet operator mutants", Nucleic Acids Research, 18(10):2875–80, 1990.

Skraly, et al., "Construction and Characterization of a 1,3–Propanediol Operon", Applied and Environmental Microbiology, 64(1):98–105, 1998.

Smith, et al., "A site–directed chromosomal translocation induced in embryonic stem cells by Cre–loxP recombination", Nature Genetics, 9:376–85, 1995.

Snaith, et al., "Multiple cloning sites carrying loxP and FRT recognition sites for the Cre and Flp site–specific recombinases", GENE, 166(1):173–74, 1995.

Spengler, et al., "The Stereostructure of Knots and Catenanes Produced by Phase λ Integrative Recombination: Implications for Mechanism and DNA Structure", CELL, 42:325–34, 1985.

Stassi, et al., "Ethyl–substituted erythromycin derivatives produced by directed metabolic engineering", Proc. Natl. Acad. Sci. USA, 95:7305–09, 1998.

Sternberg, "Bacteriophage P1 cloning system for the isolation, amplification, and recovery of DNA fragments as large as 100 kilobase pairs", Proc. Natl. Acad. Sci. USA, 87(1):103–07, 1990.

Sternberg, et al., "Site–specific Recombination and Its Role in the Life Cycle of Bacteriophage P1", *Cold Spring Harbor Symp. Quant. Biol.* 45:297–309, 1981.

Storck, et al., "Rapid construction in yeast of complex targeting vectors for gene manipulation in the mouse", Nucleic Acids Research, 24(22):4594–96, 1996.

Strathmann, et al., "Transposon–facilitated DNA sequencing", Proc. Natl. Acad. Sci. USA, 88:1247–50, 1991.

Thompson, et al., "Mutations in an Integration Host Factor–Binding Site: Effect on Lambda Site–Specific Recombination and Regulatory Implications", Journal of Bacteriology, 168(3):1343–51, 1986.

Thompson, et al., "Helical–repeat dependence of integrative recombination of Bacteriophage λ: Role of the P1 and H1 protein binding sites", Proc. Natl. Acad. Sci. USA, 85:6323–27, 1988.

Thorpe and Smith, "In vitro site–specific integration of Bacteriophage DNA catalyzed by a recombinase of the resolvase/invertase family", Proc. Natl. Acad. Sci. USA, 95:5505–10, 1998.

Vanin, et al., "Development of High–Titer Retroviral Producer Cell Lines by Using Cre–Mediated Recombination", Journal of Virology, 71:7820–26, 1997.

Wasserman, et al., "The helical repeat of double–stranded DNA varies as a function of catenation and supercoiling", Nature, 334:448–50, 1988.

Wierzbicki, et al., "A Mutational Analysis of the Bacteriophage P1 Recombinase Cre", J. Mol. Biol, 195:785–94, 1987.

Wild, et al., "A broad–host–range in vivo pop–out and amplification system for generating large quantities of 50– to 100–kb genomic fragments for direct DNA sequencing", GENE, 179:181–88, 1996.

Winoto, et al., "Directional Control of Site–specific Recombination by Bacteriophage λ", J. Mol. Biol, 192:677–80, 1986.

Wittman, "Architecture of Prokaryotic Ribosomes", Ann. Rev. of Biochem., 52:35–65, 1983.

Wittman, "Components of Bacterial Ribosomes", Ann. Rev. of Biochem., 51:155–83, 1982.

Yanisch–Perron, et al., "Improved M13 phage cloning vectors and host strains: nucleotide sequences of the M13mp18 and pUC19 vectors", GENE, 33:103–19, 1985.

York, et al., "Simple and efficient generation in vitro of nested deletions and inversions: Tn5 intramolecular transposition", Nucleic Acids Research, 26(8):1927–33, 1998.

Zhu, et al., "Homology Requirements for Ligation and Strand exchange by the FLP Recombinase", The Journal of Biological Chemistry, 270(19):11646–53, 1995.

Albert, et al., "Site–specific integration of DNA into wild–type and mutant lox sites placed in the plant genome", The Plant Journal, 7(4):649–59, 1995.

Bernard, "Positive Selection of Recombinant DNA by CcdB", BIOTECHNIQUES, 21(2):320–23, 1996.

Dale and Ow, "Mutations in the CRE/LOX Recombination Site Enhance the Stability of Recombinations Products: Applications for Gene Targeting in Plants", The Journal of Cellular Biochemistry, 16F:206, 1992.

Davies and Riechmann, "An antibody VH domain with a lox–Cre site integrated into its coding region: bacterial recombination within a single polypeptide chain", FEBS Letters, 377(1):92–96, 1995.

Hall and Collis, "Mobile gene cassettes and integrons: capture and spread of genes by site–specific recombination", Molecular Microbiology, 15(4):593–600, 1995.

Henikoff, "Unidirectional digestion with exonuclease III creates targeted breakpoints for DNA sequencing", GENE, 28(3):351–59, 1984.

Krafte, et al., "Stable Expression and Functional Characterization of a human Cardiac Na$^+$ Channel Gene in Mammalian Cells", J. Mol. Cell Cardiol., 27(2):823–30, 1995.

Lee and Saito, "Role of nucleotide sequences of loxP spacer region in Cre–mediated recombination", GENE, 216(1):55–65, 1998.

Venkatesh and Radding, "Ribosomal Protein S1 and NusA Protein Complexed to Recombination Protein β of Phage λ", Journal of Bacteriology, 175(6):1844–46, 1993.

"Current Protocols in Molecular Biology, vol. 1", Ausubel, et al., eds., John Wiley & Sons, Inc., 1.5.1–1.5.17, 1998.

"Current Protocols in Molecular Biology, vol. 1", Ausubel, et al., eds., John Wiley & Sons, Inc., 8.5.1–8.5.10, 1998.

Reed, "Transposon–Mediated Site–Specific Recombination: A Defined in Vitro System", CELL, 25:713–19, 1981.

Yang and Mizuuchi, "Site–Specific Recombination in plane view", STRUCTURE, 5:1401–06, 1997.

Hasan, et al., "*Escherichia coli* genome targeting, I. Cre–lox–mediated in vitro generation of ori$^-$ plasmids and their in vivo chromosomal integration and retrieval," *Gene* 150:51–56 (1994).

Holt, et al., "A novel phage λ replacement Cre–lox vector that has automatic subcloning capabilities," Gene 133:95–97 (1993).

Elledge, et al., "YES: A multifunctional cDNA expression vector for the isolation of genes by complementation of yeast and *Escherichia coli* mutations," Proc. *Natl. Acad. Sci. USA* 88:1731–1735 (1991).

Brunelli, et al., "Lambda/Plasmid Vector Construction by In Vivo Cre/lox–Mediated Recombination," BioTechniques 16(6):1061–1064 (1994).

Stryer, *Biochemistry*, $2^{nd}$ ed., W.H. Freeman and Co., San Francisco, CA (1981), p. 610.

Sambrook, J., et al., *Molecular Cloning: A Laboratory Manual*, $2^{nd}$ ed., Cold Spring Harbor Laboratory press, New York (1989) pp. 16.6–16.8.

Maniatis, et al., "Regulation of Inducible and Tissue–Specific Gene Expression," *Science* 236:1237–1245 (1987).

Voss, et al., "The role of enhancers in the regulation of cell–type–specific transcriptional control," *Trends Biochem. Sci.*, 11:287–289 (1986).

Dijkema, et al., "Cloning and expression of the chromosomal immune interferon gene of the rate," EMBO J. 4:761–767 (1985).

Uetsuki, et al., "Isolation and Characterization of the Human Chromosomal Gene for Polypeptide Chain Elongation Factor–1α*," *J. Biol. Chem.*, 264:5791–5798 (1989).

Kim, et al., "Use of the human elongation factor 1α promoter as a versatile and efficient expression system," *Gene* 91:217–223 (1990).

Mizushima and Nagata, "pEF–BOS, a powerful mammalian expression vector," *Nuc. Acids. Res.*, 18:5322 (1990).

Gorman, et al., "The Rous sarcoma virus long terminal repeat is a strong promoter when introduced into a variety of eukaryotic cells by DNA–mediated transfection," *Proc. Natl. Acad. Sci. USA* 79:6777–6781 (1982).

Boshart, et al., "A Very Strong Enhancer Is Located Upstream of an Immediate Early Gene of Human Cytomegalovirus," *Cell* 41:521–530 (1985).

Metcalf, et al. (1996) "Conditionally Replicative and Conjugative Plasmids Carrying lacZa for Cloning, Mutagenesis, and Allele Replacement in Bacteria," *Plasmid* 35:1–13.

Ayres, et al. (1993) "Precise Deletions in Large Bacterial Genomes by Vector–mediated Excision (VEX): The trfA Gene of Promiscuous Plasmid RK2 is Essential for Replication in Several Gram–negative Hosts," *J. Mol. Biol.* 230:174–185.

Pal, et al. (1986) "P1 Plasmid Replication Role of Initiator Titration in Copy Number Control," *J. Mol. Biol.* 192:275–285.

Sugiura, et al., (1992) "Minimal Essential Origin of Plasmid pSC101 Replication: Requirement of a Region Downstream of Iterons," *J. Bacteriol.* 175:5993–6001.

Stenzel, et al., "The Integration Host Factor of *Escherichia coli* Binds to Bent DNA at the Origin of Replication of the Plasmid pSC101," (1987) Cell 49:709.

Grindley and Kelley (1976) "Effects of Different Alleles of the *E. coli* K12 polA Gene on the Replication of Non–transferring Plasmids," *Mol. Gen. Genet.* 143:311–318.

Mendiola and de la Cruz (1989) "Specificity of Insertion of 1S91, an Insertion Sequence Present in alpha–haemolysin plasmids of *Escherichia coli*," *Mol. Microbiol.* 3:979.

Francia and Lobo (1996) "Gene Integration in the *Escherichia coli* Chromosome Mediated by Tn21 Integrase (Int21)," *J. Bact.* 178:894–898.

Sternberg, et al., (1981) "Site–specific Recombination and Its Role in the Life Cycle of Bacteriophage P1," *Cold Spring Harbor Symp. Quant. Biol.* 45:297–309.

Hoess, et al., (1982) "P1 site–specific recombination: Nucleotide sequence of the recombining sites," *Proc. Natl. Acad. Sci. USA* 79:3398–3402.

Hoess, et al., (1984) "Interaction of the bacteriophage P1 recombinase Cre with the recombining site loxP," *Proc. Natl. Acad. Sci. USA* 81:1026–1029.

Abremski, et al., (1983) "Studies on the Properties of P1 Site–Specific Recombination: Evidence for Topologically Unlinked Products following Recombination," *Cell* 32:1301–1311.

Abremski, et al., (1984) "Bacteriophage P1 Site–specific Recombination," *Journal of Biological Chemistry* 259:1509–1514.

Hoess and Abremski, (1985) "Mechanism of Strand Cleavage and Exchange in the Cre–lox Site–specific Recombination System," *J. Mol. Biol.* 181:351–362.

Cox (1983) "The FLP protein of the yeast 2–μm plasmid: Expression of a eukaryotic genetic recombination system in *Escherichia coli*," *Proc. Natl. Acad. Sci. USA* 80:4223–4227.

Meyer–Lean, et al. (1987) "Purification of the FLP site–specific recombinase by affinity chromatography and re–examination of basic properties of the system," *Nucleic Acids Res.* 15:6469–6488.

Babineau, et al., (1985) "The FLP Protein of the 2–micron Plasmid of Yeast," *J. Biol. Chem.* 260:12313–12319.

Gronostajski and Sadowski (1985) "The FLP Protein of the 2–micron Plasmid of Yeast," *J. Biol. Chem.* 260–12328–12335.

Weisberg, et al., "Site–specific recombination in Phage Lambda," In: *Lambda II*, Hendrix, et al. Eds., Cold Spring Harbor Press, Cold Spring Harbor, NY (1983) pp. 211–250.

Leslie and Sherratt (1995) "Site–specific recombination in the replication terminus region of *Escherichia coli*: functional replacement of dif," *EMBO J.* 14:1561.

Lu and Churchward (1994) "Conjugative transposition: Tn916 integrase contains two independent DNA binding domains that recognize different DNA sequences," *EMBO J.* 13:1541–1548.

Mercier, et al. (1990) "Structural and Functional Characterization of tnpl, a Recombinase Locus in Tr21 and Related β–Lactamase Transposons," *J. Bacteriol.* 172:3745–3757.

Flanagan, et al.(1989) "Analysis of Inhibitors of the Site–specific Recombination Reaction Mediated by Tn3 Resolvase," *J. Mol. Biol.* 206:295.

Stark, et al. (1989) "Site–Specific Recombination by Tn3 Resolvase: Topological Changes in the Forward and Reverse Reactions," *Cell* 58:779–790.

Sato, et al. (1990) "The cisA Cistron of *Bacillus subtilis* Sporulation Gene spoIVC Encodes a Protein Homologous to a Site–Specific Recombinase," *J. Bacteriol.* 172:1092–1098.

Glasgow, et al. (1989) "DNA–binding Properties of the Hin Recombinase," *J. Biol. Chem.* 264:10072–10082.

Hafter, et al. (1988) "Enhancer–independent mutants of the Cin recombinase have a relaxed topological specificity," *EMBO J.* '7:3991–3996.

Malynn, et al. Cell (1988) "The scid Defect Affects the Final Step of the Immunoglobin VDJ Recombinase Mechanism," 54:453–460.

Schild, et al. (1990) "Cloning of three human multifunctional de novo purine biosynthetic genes by functional complementation of yeast mutations," *Proc. Natl. Acad. Sci. USA* 87:2916–2920.

Bai, et al. (1996) "SKPI Connects Cell Cycle Regulators to the Ubiquitin Proteolysis Machinery through a Novel Motif, the F–Box," *Cell* 86:263–274.

Hoess, et al. (1986) "The role of the loxP spacer region in P1 site–specific recombination," *Nucleic Acids Res.* 14:2287–2300.

Gay, et al. (1985) "Positive Selection Procedure for Entrapment of Insertion Sequence Elements in Gram–Negative Bacteria," *J. Bacteriol.* 164:918–1237.

Gay, et al. (1983) "Cloning Structural Gene sacB, Which Codes for Exoenzyme Levansucrase of *Bacillus subtilis*: Expression of the Gene in *Escherichia coli*," *J. Bacteriol.* 153:1424–1431.

Cigan, et al. (1988) "Mutational Analysis of the HIS4 Translational Initiator Region in *Saccharomyces cerevisiae*," *Mol. Cell. Biol.* 8:2964–2975.

Yoon, et al. (1992) "SSL1, a Suppressor of a HIS4 5'–UTR Stem–Loop Mutation, is Essential for Translation Initiation and Affects UV Resistance in Yeast," *Genes and Dev.* 6:2463.

Kaniga, et al., "A wide–host–range suicide vector for improving reverse genetics in Gram–negative bacteria: inactivation of the blaA gene of *Yersinia enterocolitica*," *Gene* 109(1):137–141 (1991).

Holt & May, "A novel phage λ replacement Cre–lox vector that has automatic subcloning capabilities," *Cell Biology*, 95–97 (1993).

Wang, et al., "pDUAL: a transposon–based cosmid cloning vector for generating nested deletions and DNA sequencing templates in vivo," *Proc. Natl. Acad. Sci. USA* 90(16):7874–7878 (1993).

Palazzolo, et al., "Phage lambda cDNA cloning vectors for subtractive hybridization, fusion–protein synthesis and Cre––loxP automatic plasmid subcloning," *Gene* 88:25–36 (1990).

Waterhouse, et al., "Combinatorial infection and in vivo recombination: a strategy for making large phage antibody repertoires," *Nucleic Acids Research* 21(9):2265–2266 (1993).

Sauer, "Functional Expression of the cre–lox Site–Specific Recombination System in the Yeast *Saccharomyces cerevisiae*," *Molecular and Cellular Biology* 7(6):2087–2096 (1987).

Sternberg, et al., "Bacteriophage P1 cre Gene and its Regulatory Region Evidence for Multiple Promoters and for Regulation by DNA Methylation," *Mol. Biol.* 187:197–212 (1986).

Tsurushita, et al., "Phage display vectors for in vivo recombination of immunoglobulin heavy and light chain genes to make large combinatorial libraries," *Gene* 172:59–63 (1996).

Hoess, et al., "Formation of small circular DNA molecules via an in vitro site–specific recombination system," *Gene* 40:325–329 (1985).

Kolb and Siddell, "Genomic targeting with an MBP–Cre fusion protein," *Gene* 183:53–60 (1996).

* cited by examiner

```
 (401) NotI   KpnI                        LOX
GC GGC CGC  GGT ACC  ATA ACT TCG TAT AGC ATA CAT TAT ACG AAG TTA TCT

EcoRI    SmaI     XhoI      NdeI    NcoI    BamHI     NotI
GGA ATT  CCC CGG  GCT CGA  GAA CAT  ATG GCC  ATG GGG  ATC CGC GGC CGC

HpaI       SalI      SacI
AAT TGT TAA  CAG ATC CGT CGA  CGA GCT CGC TA (530)
```

CONSTRUCTION OF pGst-lox:

A  LINKER: C ATG GCT ATA ACT TCG TAT AGC ATA CAT TAT ACG AAG TTA TG (SEQ ID NO: 3)
            CGA TAT TGA AGC ATA TCG TAT GTA ATA TGC TTC AAT AC CTAG (SEQ ID NO: 4)
           NcoI                                                    BamHI

B  MCS: CAT ATG CCC ATG GCT CGA GGA TCC GAA TTC
        NdeI    NcoI   XhoI   BamHI  EcoRI pGEX-2TKcs (5.0kb), Ap^R, P_tac, Gst CONSTRUCTION OF pVL1392-lox:

A

LINKER: GG CCG GAC GTC ATA ACT TCG TAT AGC ATA CAT TAT ACG AAG TTA TG (SEQ ID NO: 6)
C CTG CAG TAT TGA AGC ATA TCG TAT GTA ATA TGC TTC AAT AC CTAG (SEQ ID NO: 7)

B

MCS: BglII/PstI/NotI/XmaI/EcoRI/XbaI/SmaI/BamHI

FIG. 13

```
                      T        C
                      |        |
loxP:    A T A A C T T C G T A T A   G C A T A C A T   T A T A C G A A G T T A T (SEQ ID NO: 12)
         1 2 3 4 5 6 7 8 9 10 11 12 13                 13 12 11 10 9 8 7 6 5 4 3 2 1 loxP2:   A T A A C T T C G T A T A   G C A T A C A T   T A T A C G A A G T T A T (SEQ ID NO: 13)
         1 2 3 4 5 6 7 8 9 10 11 12 13                 13 12 11 10 9 8 7 6 5 4 3 2 1

T
                                                              |
loxP3:   A T A A C T T C G T A T A   G C A T A C A T   T A T A C G A A G T T A T (SEQ ID NO: 14)
         1 2 3 4 5 6 7 8 9 10 11 12 13                 13 12 11 10 9 8 7 6 5 4 3 2 1

T                                       T
                      |                                       |
loxP23:  A T A A C T T C G T A T A   G C A T A C A T   T A T A C G A A G T T A T (SEQ ID NO: 15)
         1 2 3 4 5 6 7 8 9 10 11 12 13                 13 12 11 10 9 8 7 6 5 4 3 2 1
```

| GST-Cre (μg) | NUMBER OF Ap^R TRANSFORMANTS | NUMBER OF Kn^R TRANSFORMANTS | Kn^R/Ap^R (%) |
|---|---|---|---|
| 0 | $4.0 \times 10^5$ | 0 | 0 |
| 0.02 | $3.0 \times 10^5$ | 231 | 0.1 |
| 0.04 | $2.3 \times 10^5$ | 406 | 0.2 |
| 0.06 | $2.4 \times 10^5$ | 868 | 0.4 |
| 0.08 | $3.3 \times 10^5$ | 1,336 | 0.4 |
| 0.10 | $6.0 \times 10^4$ | 594 | 1.0 |
| 0.20 | $7.8 \times 10^4$ | 580 | 0.7 |
| 0.40 | $5.8 \times 10^4$ | 1,910 | 3.3 |
| 0.60 | $9.2 \times 10^4$ | 10,750 | 11.7 |
| 0.80 | $3.1 \times 10^5$ | 28,660 | 9.2 |
| 1.00 | $1.0 \times 10^5$ | 16,840 | 16.8 |

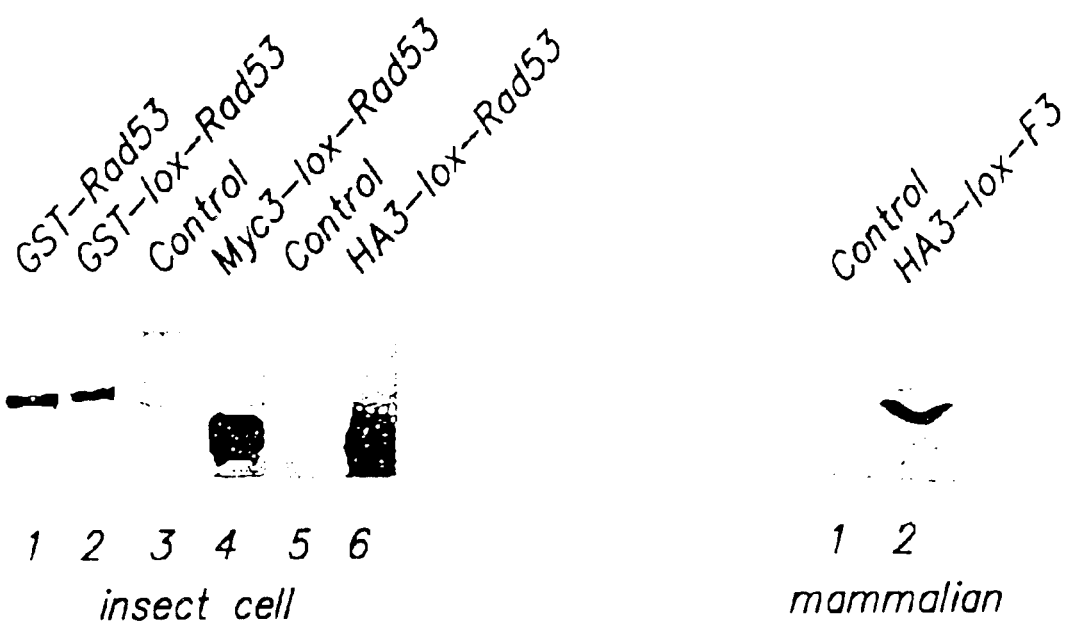
FIG. 18
FIG. 19
FIG. 21
Pvu II restriction analysis of recombinant plasmids made by one-step POT
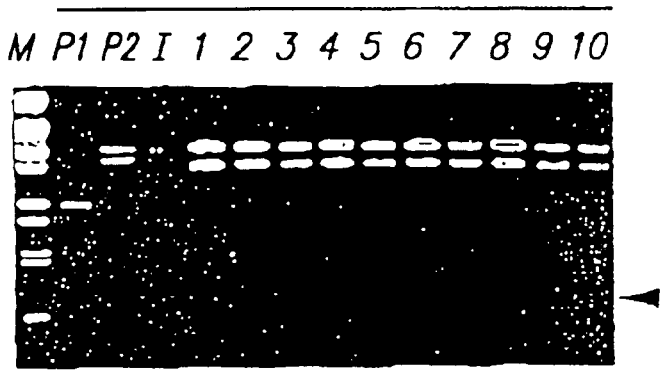

pUNI 10 POLYLINKER SEQUENCE

| (401) NotI | KpnI | | | LOX | | | |
|---|---|---|---|---|---|---|---|
| GC GGC CGC | GGT ACC | ATA ACT | TCG TAT | AGC ATA | CAT TAT | ACG A | |

| | EcoRI | SmaI | XhoI | | NdeI | NcoI |
|---|---|---|---|---|---|---|
| AG TTA TCT | GGA ATT | CCC CGG | GCT CGA | GAA | CAT ATG | GCC ATG G |

| BamHI | NotI | | HpaI | | SalI | SacI (530) |
|---|---|---|---|---|---|---|
| GG ATC | CGC GGC CGC | AAT | TGT TAA | CAG | ATC CGT CGA | CGA GCT | pUNI 20 POLYLINKER SEQUENCE

<u>(157) KpnI</u>                                      <u>LOX</u>
GGT ACC ATA ACT TCG TAT AGC ATA CAT TAT ACG AAG TTA T

<u>EcoR I</u>   <u>SmaI</u>   <u>XhoI</u>   <u>Nde I</u>   <u>Nco I</u>   <u>BamHI</u>
CT GGA ATT CCC CGG GCT CGA GAA CAT ATG GCC ATG GGA TC

<u>Not I (246)</u>
CGC GGC CGC pUNI 30 POLYLINKER SEQUENCE

<u>(37) KpnI</u>                                              <u>LOX</u>
GGT ACC ATA ACT TCG TAT AGC ATA CAT TAT ACG AAG TTA TC

<u>EcoR I</u>   <u>SmaI</u>    <u>XhoI</u>           <u>EcoIIIII</u>
T GGA ATT CCC CGG GCT CGA GCC AGT CCA GCG CTC ACA ATT
                                              <u>half IacO</u>

<u>Not I</u>       <u>HpaI</u>         <u>Sal I</u>   <u>SacI (155)</u>
GCG GGC GCA ATT GTT AAC AGA TCC GTC GAC GAG CTC GC
         <u>MunI</u>

FIG. 26A-1

SEQUENCE DESCRIPTION: SEQ ID NO:1:

```
AATTCTGTCA GCCGTTAAGT GTTCCTGTGT CACTGAAAAT TGCTTTGAGA GGCTCTAAGG
60
GCTTCTCAGT GCGTTACATC CCTGGCTTGT TGTCCACAAC CGTTAAACCT TAAAAGCTTT
120
AAAAGCCTTA TATATTCTTT TTTTTCTTAT AAAACTTAAA ACCTTAGAGG CTATTTAAGT
180
TGCTGATTTA TATTAATTTT ATTGTTCAAA CATGAGAGCT TAGTACGTGA AACATGAGAG
240
CTTAGTACGT TAGCCATGAG AGCTTAGTAC GTTAGCCATG AGGGTTTAGT TCGTTAAACA
300
TGAGAGCTTA GTACGTTAAA CATGAGAGCT TAGTACGTGA AACATGAGAG CTTAGTACGT
360
ACTATCAACA GGTTGAACTG CTGATCAACA GATCCTCTAC GCGGCCGCGG TACCATAACT
420
TCGTATAGCA TACATTATAC GAAGTTATCT GGAATTCCCC GGGCTCGAGA ACATATGGCC
480
ATGGGGATCC GCGGCCGCAA TTGTTAACAG ATCCGTCGAC GAGCTCGCTA TCAGCCCTCGA
540
```

FIG. 26A-2

```
CTGTGCCTTC TAGTTGCCAG CCATCTGTTG TTTGCCCCTC CCCCGTGCCT TCCTTGACCC
600
TGGAAGGTGC CACTCCCACT GTCCTTTCCT AATAAAATGA GGAAATTGCA TCGCATTGTC
660
TGAGTAGGTG TCATTCTATT CTGGGGGGTG GGGTGGGGCA GGACAGCAAG GGGGAGGATT
720
GGGAAGACAA TAGCAGGCAT GCTGGGGATT CTAGAAGATC CGGCTGCTAA CAAAGCCCGA
780
AAGGAAGCTG AGTTGGCTGC TGCCACCGCT GAGCAATAAC TAGCATAACC CCTTGGGGCC
840
TCTAAACGGG TCTTGAGGGG TTTTTTGCTG AAAGGAGGAA CTATATCCGG ATATCCCGGG
900
GTGGGCGAAG AACTCCAGCA TGAGATCCCC GCGCTGGAGG ATCATCCAGC CGGCGTCCCG
960
GAAAACGATT CCGAAGCCCA ACCTTTCATA GAAGGCGGGCG GTGGAATCGA AATCTCGTGA
1020
TGGCAGGTTG GGCGTCGCTT GGTCGGTCAT TTCGAACCCC AGAGTCCCGC TCAGAAGAAC
1080
```

FIG. 26A-3

```
1140  TCGTCAAGAA GGCGATAGAA GGCGATGCGC TGCGAATCGG GAGCGGGCGAT ACCGTAAAGC
1200  ACGAGGAAGC GGTCAGCCCA TTCGCCGCCA AGCTCTTCAG CAATATCACG GGTAGCCAAC
1260  GCTATGTCCT GATAGCGGTC CGCCACACCC AGCCGGCCAC AGTCGATGAA TCCAGAAAAG
1320  CGGCCATTTT CCACCATGAT ATTCGGCAAG CAGGCATCGC CATGGGTCAC GACGAGATCC
1380  TCGCCGTCGG GCATGCGCGC CTTGAGCCTG GCGAACAGTT CGGCTGGCGC GAGCCCCTGA
1440  TGCTCTTCGT CCAGATCATC CTGATCGACA AGACCGGCTT CCATCCGAGT ACGTGCTCGC
1500  TCGATGCGAT GTTTCGCTTG GTGGTCGAAT GGGCAGGTAG CCGGATCAAG CGTATGCAGC
1560  CGCCGCATTG CATCAGCCAT GATGGATACT TTCTCGGCAG GAGCAAGGTG AGATGACAGG
1620  AGATCCTGCC CCGGCACTTC GCCCAATAGC AGCCAGTCCC TTCCCGCTTC AGTGACAACG
1680  TCGAGCACAG CTGCGCAAGG AACGCCCGTC GTGGCCAGCC ACGATAGCCG CGCTGCCTCG
```

FIG. 26A-4

```
TCCTGCAGTT CATTCAGGGC ACCGGACAGG TCGGTCTTGA CAAAAAGAAC CGGGGCCCC
1740
TGCGCTGACA GCCGGAACAC GGCGGGCATCA GAGCAGCCGA TTGTCTGTTG TGCCCAGTCA
1800
TAGCCCGAATA GCCTCTCCAC CCAAGCGGGCC GGAGAACCTG CGTGCAATCC ATCTTGTTCA
1860
ATCATGCGAA ACGATCCTCA TCCTGTCTCT TGATCAGATC TTGATCCCCT GCGCCATCAG
1920
ATCCTTGGCG GCAAGAAAGC CATCCAGTTT ACTTTGCAGG GCTTCCCAAC CTTACCAGAG
1980
GGCGCCCCAG CTGGCAATTC CGGTTCGCTT GCTGTCCATA AAACCGCCCA GTCTAGCTAT
2040
CGCCATGTAA GCCCACTGCA AGCTACCTGC TTTCTCTTTG CGCTTGCGTT TTCCCTTGTC
2100
CAGATAGCCC AGTAGCTGAC ATTCATCCGG GGTCAGCACC GTTTCTGCGG ACTGGCTTTC
2160
TACGTGTTCC GCTTCCTTTA GCAGCCCTTG CGCCCTGAGT GCTTGCGGGCA GCGTGAAGCT
2220
```

FIG. 26B-1

SEQUENCE DESCRIPTION: SEQ ID NO:10:

```
     ATG TCC CCT ATA CTA GGT TAT TGG AAA ATT AAG GGC CTT GTG CAA CCC
48
     Met Ser Pro Ile Leu Gly Tyr Trp Lys Ile Lys Gly Leu Val Gln Pro
     1               5                  10                  15

ACT CGA CTT CTT TTG GAA TAT CTT GAA GAA AAA TAT GAA GAG CAT TTG
96
     Thr Arg Leu Leu Leu Glu Tyr Leu Glu Glu Lys Tyr Glu Glu His Leu
                 20                  25                  30

TAT GAG CGC GAT GAA GGT GAT AAA TGG CGA AAC AAA AAG TTT GAA TTG
144
     Tyr Glu Arg Asp Glu Gly Asp Lys Trp Arg Asn Lys Lys Phe Glu Leu
             35                  40                  45

GGT TTG GAG TTT CCC AAT CTT CCT TAT TAT ATT GAT GGT GAT GTT AAA
192
     Gly Leu Glu Phe Pro Asn Leu Pro Tyr Tyr Ile Asp Gly Asp Val Lys
     50                  55                  60

TTA ACA CAG TCT ATG GCC ATC ATA CGT TAT ATA GCT GAC AAG CAC AAC
240
     Leu Thr Gln Ser Met Ala Ile Ile Arg Tyr Ile Ala Asp Lys His Asn
     65                  70                  75                  80
```

FIG. 26B-2

```
ATG TTG GGT GGT TGT CCA AAA GAG CGT GCA GAG ATT TCA ATG CTT GAA
288
Met Leu Gly Gly Cys Pro Lys Glu Arg Ala Glu Ile Ser Met Leu Glu
                85                  90                  95

GGA GCG GTT TTG GAT ATT AGA TAC GGT GTT TCG AGA ATT GCA TAT AGT
336
Gly Ala Val Leu Asp Ile Arg Tyr Gly Val Ser Arg Ile Ala Tyr Ser
                100                 105                 110

AAA GAC TTT GAA ACT CTC AAA GTT GAT TTT CTT AGC AAG CTA CCT GAA
384
Lys Asp Phe Glu Thr Leu Lys Val Asp Phe Leu Ser Lys Leu Pro Glu
            115                 120                 125

ATG CTG AAA ATG TTC GAA GAT CGT TTA TGT CAT AAA ACA TAT TTA AAT
432
Met Leu Lys Met Phe Glu Asp Arg Leu Cys His Lys Thr Tyr Leu Asn
            130                 135                 140

GGT GAT CAT GTA ACC CAT CCT GAC TTC ATG TTG TAT GAC GCT CTT GAT
480
Gly Asp His Val Thr His Pro Asp Phe Met Leu Tyr Asp Ala Leu Asp
            145                 150                 155                 160
```

FIG. 26B-3

```
528  GTT GTT TTA TAC ATG GAC CCA ATG TGC CTG GAT GCG TTC CCA AAA TTA
     Val Val Leu Tyr Met Asp Pro Met Cys Leu Asp Ala Phe Pro Lys Leu
             165                 170                 175

576  GTT TGT TTT AAA AAA CGT ATT GAA GCT ATC CCA CAA ATT GAT AAG TAC
     Val Cys Phe Lys Lys Arg Ile Glu Ala Ile Pro Gln Ile Asp Lys Tyr
             180                 185                 190

624  TTG AAA TCC AGC AAG TAT ATA GCA TGG CCT TTG CAG GGC TGG CAA GCC
     Leu Lys Ser Ser Lys Tyr Ile Ala Trp Pro Leu Gln Gly Trp Gln Ala
             195                 200                 205

672  ACG TTT GGT GGT GGC GAC CAT CCT CCA AAA TCG GAT CTG GTT CCG CGT
     Thr Phe Gly Gly Gly Asp His Pro Pro Lys Ser Asp Leu Val Pro Arg
             210                 215                 220

720  GGA TCT CGT GCA TCT GTT GGA TCG CAT ATG CCC ATG GCC AAT TTA
     Gly Ser Arg Ala Ser Val Gly Ser His Met Pro Met Ala Asn Leu
             225                 230                 235         240

768  CTG ACC GTA CAC CAA AAT TTG CCT GCA TTA CCG GTC GAT GCA ACG AGT
     Leu Thr Val His Gln Asn Leu Pro Ala Leu Pro Val Asp Ala Thr Ser
             245                 250                 255
```

FIG. 26B-4

```
     GAT GAG GTT CGC AAG AAC CTG ATG GAC ATG TTC AGG GAT CGC CAG GCG
816  Asp Glu Val Arg Lys Asn Leu Met Asp Met Phe Arg Asp Arg Gln Ala
                 260                 265                 270

TTT TCT GAG CAT ACC TGG AAA ATG CTT CTG TCC GTT TGC CGG TCG TGG
864  Phe Ser Glu His Thr Trp Lys Met Leu Leu Ser Val Cys Arg Ser Trp
                 275                 280                 285

GCG GCA TGC AAG TTG AAT AAC CGG AAA TGG TTT CCC GCA GAA CCT
912  Ala Ala Cys Lys Leu Asn Asn Arg Lys Trp Phe Pro Ala Glu Pro
         290                 295                 300

GAA GAT GTT CGC GAT TAT CTT CTA TAT CTT CAG GCG CGC GGT CTG GCA
960  Glu Asp Val Arg Asp Tyr Leu Leu Tyr Leu Gln Ala Arg Gly Leu Ala
                 305                 310                 315             320

GTA AAA ACT ATC CAG CAA CAT TTG GGC CAG CTA AAC ATG CTT CAT CGT
1008 Val Lys Thr Ile Gln Gln His Leu Gly Gln Leu Asn Met Leu His Arg
                 325                 330                 335

CGG TCC GGG CTG CCA CGA CCA AGT GAC AGC AAT GCT GTT TCA CTG GTT
1056 Arg Ser Gly Leu Pro Arg Pro Ser Asp Ser Asn Ala Val Ser Leu Val
                 340                 345                 350
```

FIG. 26B-5

```
1104 ATG CGG CGG ATC CGA AAA GAA AAC GTT GAT GCC GGT GAA CGT GCA AAA
     Met Arg Arg Ile Arg Lys Glu Asn Val Asp Ala Gly Glu Arg Ala Lys
         355                     360                 365

1152 CAG GCT CTA GCG TTC GAA CGC ACT GAT TTC GAC CAG GTT CGT TCA CTC
     Gln Ala Leu Ala Phe Glu Arg Thr Asp Phe Asp Gln Val Arg Ser Leu
                 370                 375                 380

1200 ATG GAA AAT AGC GAT CGC TGC CAG GAT ATA CGT AAT CTG GCA TTT CTG
     Met Glu Asn Ser Asp Arg Cys Gln Asp Ile Arg Asn Leu Ala Phe Leu
     385                 390                 395                 400

1248 GGG ATT GCT TAT AAC ACC CTG TTA CGT ATA ATC GAA ATT GCC AGG ATC
     Gly Ile Ala Tyr Asn Thr Leu Leu Arg Ile Ile Ala Glu Ile Ala Arg Ile
             405                 410                 415

1296 AGG GTT AAA GAT ATC TCA CGT ACT GAC GGT GGG AGA ATG TTA ATC CAT
     Arg Val Lys Asp Ile Ser Arg Thr Asp Gly Gly Arg Met Leu Ile His
                 420                 425                 430

1344 ATT GGC AGA ACG AAA ACG CTG GTT AGC ACC GCA GGT GTA GAG AAG GCA
     Ile Gly Arg Thr Lys Thr Leu Val Ser Thr Ala Gly Val Glu Lys Ala
     435                 440                 445
```

FIG. 26B-6

```
1392  CTT AGC CTG GGG GTA ACT AAA CTG GTC GAG CGA TGG ATT TCC GTC TCT
      Leu Ser Leu Gly Val Thr Lys Leu Val Glu Arg Trp Ile Ser Val Ser
          450             455             460

1440  GGT GTA GCT GAT GAT CCG AAT AAC TAC CTG TTT TGC CGG GTC AGA AAA
      Gly Val Ala Asp Asp Pro Asn Asn Tyr Leu Phe Cys Arg Val Arg Lys
      465             470             475             480

1488  AAT GGT GTT GCC GCG CCA TCT GCC ACC AGC CAG CTA TCA ACT CGC GCC
      Asn Gly Val Ala Ala Pro Ser Ala Thr Ser Gln Leu Ser Thr Arg Ala
              485             490             495

1536  CTG GAA GGG ATT TTT GAA GCA ACT CAT CGA TTG ATT TAC GGC GCT AAG
      Leu Glu Gly Ile Phe Glu Ala Thr His Arg Leu Ile Tyr Gly Ala Lys
          500             505             510

1584  GAT GAC TCT GGT CAG AGA TAC CTG GCC TGG TCT GGA CAC AGT GCC CGT
      Asp Asp Ser Gly Gln Arg Tyr Leu Ala Trp Ser Gly His Ser Ala Arg
              515             520             525

1632  GTC GGA GCC GCC CGA GAT ATG GCC CGC GCT GGA GTT TCA ATA CCG GAG
      Val Gly Ala Ala Arg Asp Met Ala Arg Ala Gly Val Ser Ile Pro Glu
          530             535             540
```

FIG. 26B-7

```
ATC ATG CAA GCT GGT GGC TGG ACC AAT GTA AAT ATT GTC ATG AAC TAT
1680
Ile Met Gln Ala Gly Gly Trp Thr Asn Val Asn Ile Val Met Asn Tyr
545                     550                 555                 560

ATC CGT AAC CTG GAT AGT GAA ACA GGG GCA ATG GTG CGC CTG CTG GAA
1728
Ile Arg Asn Leu Asp Ser Glu Thr Gly Ala Met Val Arg Leu Leu Glu
            565                 570                 575

GAT GGC GAT TAG
1740
Asp Gly Asp
```

FIG. 26C-1

SEQUENCE DESCRIPTION: SEQ ID NO:11:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
        100                 105                 110

Lys Asp Phe Glu Thr Leu Lys Val Asp Phe Leu Ser Lys Leu Pro Glu
    115                 120                 125

FIG. 26C-2

```
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
    145                 150                 155                 160
Val Val Leu Tyr Met Asp Pro Met Cys Leu Asp Ala Phe Pro Lys Leu
                165                 170                 175
Val Cys Phe Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Asp His Pro Pro Lys Ser Asp Leu Val Pro Arg
    210                 215                 220
Gly Ser Arg Arg Ala Ser Val Gly Ser His Met Pro Met Ala Asn Leu
225                 230                 235                 240
Leu Thr Val His Gln Asn Leu Pro Ala Leu Pro Val Asp Ala Thr Ser
            245                 250                 255
Asp Glu Val Arg Lys Asn Leu Met Asp Met Phe Arg Asp Arg Gln Ala
        260                 265                 270
```

FIG. 26C-3

```
Phe Ser Glu His Thr Trp Lys Met Leu Leu Ser Val Cys Arg Ser Trp
        275                 280                 285
Ala Ala Trp Cys Lys Leu Asn Arg Lys Trp Phe Pro Ala Glu Pro
        290                 295                 300
Glu Asp Val Arg Asp Tyr Leu Leu Tyr Leu Gln Ala Arg Gly Leu Ala
        305                 310                 315                 320
Val Lys Thr Ile Gln His Leu Gly Gln Leu Asn Met Leu His Arg
        325                 330                 335
Arg Ser Gly Leu Pro Arg Pro Ser Asp Ser Asn Ala Val Ser Leu Val
        340                 345                 350
Met Arg Arg Ile Arg Lys Glu Asn Val Asp Ala Gly Glu Arg Ala Lys
        355                 360                 365
Gln Ala Leu Ala Phe Glu Arg Thr Asp Phe Asp Gln Val Arg Ser Leu
        370                 375                 380
Met Glu Asn Ser Asp Arg Cys Gln Asp Ile Arg Asn Leu Ala Phe Leu
        385                 390                 395                 400
Gly Ile Ala Tyr Asn Thr Leu Leu Arg Ile Ala Glu Ile Ala Arg Ile
        405                 410                 415
Arg Val Lys Asp Ile Ser Arg Thr Asp Gly Gly Arg Met Leu Ile His
        420                 425                 430
```

FIG. 26C-4

Ile Gly Arg Thr Lys Thr Leu Val Ser Thr Ala Gly Val Glu Lys Ala
435                          440                          445

Leu Ser Leu Gly Val Thr Lys Leu Val Glu Arg Trp Ile Ser Val Ser
450                          455                          460

Gly Val Ala Asp Asp Pro Asn Asn Tyr Leu Phe Cys Arg Val Arg Lys
465                          470                          475                          480

Asn Gly Val Ala Ala Pro Ser Ala Thr Ser Gln Leu Ser Thr Arg Ala
485                          490                          495

Leu Glu Gly Ile Phe Glu Ala Thr His Arg Leu Ile Tyr Gly Ala Lys
500                          505                          510

Asp Asp Ser Gly Gln Arg Tyr Leu Ala Trp Ser Gly His Ser Ala Arg
515                          520                          525

Val Gly Ala Ala Arg Asp Met Ala Arg Ala Gly Val Ser Ile Pro Glu
530                          535                          540

Ile Met Gln Ala Gly Gly Trp Thr Asn Val Asn Ile Val Met Asn Tyr
545                          550                          555                          560

Ile Arg Asn Leu Asp Ser Glu Thr Gly Ala Met Val Arg Leu Leu Glu
565                          570                          575

Asp Gly Asp

SEQUENCE LISTING

<160> NUMBER OF SEQ ID NOS: 32

<210> SEQ ID NO 1
<211> LENGTH: 2220
<212> TYPE: DNA
<213> ORGANISM: Artificial Sequence
<220> FEATURE:
<223> OTHER INFORMATION: Description of Artificial Sequence: Synthetic

<400> SEQUENCE: 1

```
aattctgtca gccgttaagt gttcctgtgt cactgaaaat tgctttgaga ggctctaagg      60
gcttctcagt gcgttacatc cctggcttgt tgtccacaac cgttaaacct taaaagcttt     120
aaaagcctta tatattcttt tttttcttat aaaacttaaa accttagagg ctatttaagt     180
tgctgattta tattaatttt attgttcaaa catgagagct tagtacgtga aacatgagag     240
cttagtacgt tagccatgag agcttagtac gttagccatg agggtttagt tcgttaaaca     300
tgagagctta gtacgttaaa catgagagct tagtacgtga aacatgagag cttagtacgt     360
actatcaaca ggttgaactg ctgatcaaca gatcctctac gcggccgcgg taccataact     420
tcgtatagca tacattatac gaagttatct ggaattcccc gggctcgaga acatatggcc     480
atggggatcc gcggccgcaa ttgttaacag atccgtcgac gagctcgcta tcagcctcga     540
ctgtgccttc tagttgccag ccatctgttg tttgcccctc ccccgtgcct tccttgaccc     600
tggaaggtgc cactcccact gtcctttcct aataaaatga ggaaattgca tcgcattgtc     660
tgagtaggtg tcattctatt ctggggggtg gggtggggca ggacagcaag ggggaggatt     720
gggaagacaa tagcaggcat gctgggggatt ctagaagatc cggctgctaa caaagcccga     780
aaggaagctg agttggctgc tgccaccgct gagcaataac tagcataacc ccttgggggcc     840 tctaaacggg tcttgagggg ttttttgctg aaggaggaa ctatatccgg atatcccggg     900
gtgggcgaag aactccagca tgagatcccc gcgctggagg atcatccagc cggcgtcccg    960
gaaaacgatt ccgaagccca acctttcata gaaggcggcg gtggaatcga aatctcgtga   1020
tggcaggttg ggcgtcgctt ggtcggtcat ttcgaacccc agagtcccgc tcagaagaac   1080
```

```
tcgtcaagaa ggcgatagaa ggcgatgcgc tgcgaatcgg gagcggcgat accgtaaagc    1140
acgaggaagc ggtcagccca ttcgccgcca agctcttcag caatatcacg ggtagccaac    1200
gctatgtcct gatagcggtc cgccacaccc agccggccac agtcgatgaa tccagaaaag    1260
cggccatttt ccaccatgat attcggcaag caggcatcgc catgggtcac gacgagatcc    1320
tcgccgtcgg gcatgcgcgc cttgagcctg gcgaacagtt cggctggcgc gagcccctga    1380
tgctcttcgt ccagatcatc ctgatcgaca agaccggctt ccatccgagt acgtgctcgc    1440
tcgatgcgat gtttcgcttg gtggtcgaat gggcaggtag ccggatcaag cgtatgcagc    1500
cgccgcattg catcagccat gatggatact ttctcggcag gagcaaggtg agatgacagg    1560
agatcctgcc ccggcacttc gcccaatagc agccagtccc ttcccgcttc agtgacaacg    1620
tcgagcacag ctgcgcaagg aacgcccgtc gtggccagcc acgatagccg cgctgcctcg    1680
tcctgcagtt cattcagggc accggacagg tcggtcttga caaaaagaac cgggcgcccc    1740
tgcgctgaca gccggaacac ggcggcatca gagcagccga ttgtctgttg tgcccagtca    1800
tagccgaata gcctctccac ccaagcggcc ggagaacctg cgtgcaatcc atcttgttca    1860
atcatgcgaa acgatcctca tcctgtctct tgatcagatc ttgatcccct gcgccatcag    1920
atccttggcg gcaagaaagc catccagttt actttgcagg gcttcccaac cttaccagag    1980
ggcgccccag ctggcaattc cggttcgctt gctgtccata aaaccgccca gtctagctat    2040
cgccatgtaa gcccactgca agctacctgc tttctctttg cgcttgcgtt ttcccttgtc    2100
cagatagccc agtagctgac attcatccgg ggtcagcacc gtttctgcgg actggctttc    2160
tacgtgttcc gcttcctttta gcagcccttg cgccctgagt gcttgcggca gcgtgaagct    2220

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 2
ggatccccgg gaattc                                                     16

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 3
ggatcgcata tgcccatggc tcgaggatcc gaattc                               36

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 4
catggctata acttcgtata gcatacatta tacgaagtta tg                        42

<210> SEQ ID NO 5
<211> LENGTH: 42
<212> TYPE: DNA
<213> ORGANISM: Artificial Sequence
```

```
-continued

<220> FEATURE:
<223> OTHER INFORMATION: Description of Artificial Sequence: Synthetic

<400> SEQUENCE: 5
gatccataac ttcgtataat gtatgctata cgaagttata gc                           42

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic

<400> SEQUENCE: 6
ggccggacgt cataacttcg tatagcatac attatacgaa gttatg                       46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic

<400> SEQUENCE: 7
gatccataac ttcgtataat gtatgctata cgaagttatg acgtcc                       46

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic

<400> SEQUENCE: 8
tcgagacgtc ataacttcgt atagcataca ttatacgaag ttatgc                       46

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic

<400> SEQUENCE: 9
ggccgcataa cttcgtataa tgtatgctat acgaagttat gacgtc                       46

<210> SEQ ID NO 10
<211> LENGTH: 1740
<212> TYPE: DNA
<213> ORGANISM: Artificial Sequence
<220> FEATURE:
<223> OTHER INFORMATION: Description of Artificial Sequence: Synthetic

<400> SEQUENCE: 10
atgtccccta tactaggtta ttggaaaatt aagggccttg tgcaacccac tcgacttctt        60
ttggaatatc ttgaagaaaa atatgaagag catttgtatg agcgcgatga aggtgataaa       120
tggcgaaaca aaaagtttga attgggtttg gagtttccca atcttcctta ttatattgat       180
ggtgatgtta aattaacaca gtctatggcc atcatacgtt atatagctga caagcacaac       240
atgttgggtg gttgtccaaa agagcgtgca gagatttcaa tgcttgaagg agcggttttg       300
gatattagat acgtgtttc gagaattgca tatagtaaag actttgaaac tctcaaagtt       360
gattttctta gcaagctacc tgaaatgctg aaaatgttcg aagatcgttt atgtcataaa       420
```

-continued

```
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatctcg tcgtgcatct gttggatcgc atatgcccat ggccaattta    720
ctgaccgtac accaaaattt gcctgcatta ccggtcgatg caacgagtga tgaggttcgc    780
aagaacctga tggacatgtt cagggatcgc caggcgtttt ctgagcatac ctggaaaatg    840
cttctgtccg tttgccggtc gtgggcggca tggtgcaagt tgaataaccg gaaatggttt    900
cccgcagaac ctgaagatgt tcgcgattat cttctatatc ttcaggcgcg cggtctggca    960
gtaaaaacta tccagcaaca tttgggccag ctaaacatgc ttcatcgtcg gtccgggctg   1020
ccacgaccaa gtgacagcaa tgctgtttca ctggttatgc ggcggatccg aaaagaaaac   1080
gttgatgccg gtgaacgtgc aaaacaggct ctagcgttcg aacgcactga tttcgaccag   1140
gttcgttcac tcatggaaaa tagcgatcgc tgccaggata tacgtaatct ggcatttctg   1200
gggattgctt ataacaccct gttacgtata gccgaaattg ccaggatcag ggttaaagat   1260
atctcacgta ctgacggtgg gagaatgtta atccatattg gcagaacgaa aacgctggtt   1320
agcaccgcag gtgtagagaa ggcacttagc ctggggggta actaaactggt cgagcgatgg   1380 atttccgtct ctggtgtagc tgatgatccg aataactacc tgttttgccg ggtcagaaaa   1440
aatggtgttg ccgcgccatc tgccaccagc cagctatcaa ctcgcgccct ggaagggatt   1500
tttgaagcaa ctcatcgatt gatttacggc gctaaggatg actctggtca gagatacctg   1560
gcctggtctg gacacagtgc ccgtgtcgga gccgcgcgag atatggcccg cgctggagtt   1620
tcaataccgg agatcatgca agctggtggc tggaccaatg taaatattgt catgaactat   1680
atccgtaacc tggatagtga aacaggggca atggtgcgcc tgctggaaga tggcgattag   1740
```

<210> SEQ ID NO 11
<211> LENGTH: 579
<212> TYPE: PRT
<213> ORGANISM: Artificial Sequence
<220> FEATURE:
<223> OTHER INFORMATION: Description of Artificial Sequence: Synthetic

<400> SEQUENCE: 11

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
```

```
                130               135               140
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
210                 215                 220

Gly Ser Arg Arg Ala Ser Val Gly Ser His Met Pro Met Ala Asn Leu
225                 230                 235                 240

Leu Thr Val His Gln Asn Leu Pro Ala Leu Pro Val Asp Ala Thr Ser
                245                 250                 255

Asp Glu Val Arg Lys Asn Leu Met Asp Met Phe Arg Asp Arg Gln Ala
                260                 265                 270

Phe Ser Glu His Thr Trp Lys Met Leu Leu Ser Val Cys Arg Ser Trp
                275                 280                 285

Ala Ala Trp Cys Lys Leu Asn Asn Arg Lys Trp Phe Pro Ala Glu Pro
290                 295                 300

Glu Asp Val Arg Asp Tyr Leu Leu Tyr Leu Gln Ala Arg Gly Leu Ala
305                 310                 315                 320

Val Lys Thr Ile Gln Gln His Leu Gly Gln Leu Asn Met Leu His Arg
                325                 330                 335

Arg Ser Gly Leu Pro Arg Pro Ser Asp Ser Asn Ala Val Ser Leu Val
                340                 345                 350

Met Arg Arg Ile Arg Lys Glu Asn Val Asp Ala Gly Glu Arg Ala Lys
                355                 360                 365

Gln Ala Leu Ala Phe Glu Arg Thr Asp Phe Asp Gln Val Arg Ser Leu
370                 375                 380

Met Glu Asn Ser Asp Arg Cys Gln Asp Ile Arg Asn Leu Ala Phe Leu
385                 390                 395                 400

Gly Ile Ala Tyr Asn Thr Leu Leu Arg Ile Ala Glu Ile Ala Arg Ile
                405                 410                 415

Arg Val Lys Asp Ile Ser Arg Thr Asp Gly Gly Arg Met Leu Ile His
                420                 425                 430

Ile Gly Arg Thr Lys Thr Leu Val Ser Thr Ala Gly Val Glu Lys Ala
                435                 440                 445

Leu Ser Leu Gly Val Thr Lys Leu Val Glu Arg Trp Ile Ser Val Ser
450                 455                 460

Gly Val Ala Asp Asp Pro Asn Asn Tyr Leu Phe Cys Arg Val Arg Lys
465                 470                 475                 480

Asn Gly Val Ala Ala Pro Ser Ala Thr Ser Gln Leu Ser Thr Arg Ala
                485                 490                 495

Leu Glu Gly Ile Phe Glu Ala Thr His Arg Leu Ile Tyr Gly Ala Lys
                500                 505                 510

Asp Asp Ser Gly Gln Arg Tyr Leu Ala Trp Ser Gly His Ser Ala Arg
                515                 520                 525

Val Gly Ala Ala Arg Asp Met Ala Arg Ala Gly Val Ser Ile Pro Glu
530                 535                 540

Ile Met Gln Ala Gly Gly Trp Thr Asn Val Asn Ile Val Met Asn Tyr
545                 550                 555                 560
```

```
Ile Arg Asn Leu Asp Ser Glu Thr Gly Ala Met Val Arg Leu Leu Glu
            565                 570                 575

Asp Gly Asp

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 12
ataacttcgt atagcataca ttatacgaag ttat                              34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 13
attacctcgt atagcataca ttatacgaag ttat                              34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 14
ataacttcgt atagcataca ttatatgaag ttat                              34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 15
attacctcgt atagcataca ttatatgaag ttat                              34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 16
ataacttcgt atagtataca ttatacgaag ttat                              34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 17
acaacttcgt ataatgtatg ctatacgaag ttat                              34
```

```
<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 18
gaagttccta ttctctagaa agtataggaa cttc                                 34

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 19
gcggccgctg agtgttaaat gtccaatt                                        28

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 20
cccgggctaa tcgccatctt ccagc                                           25

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 21
ccatggccaa tttactgacc gtacac                                          26

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 22
catggctata acttcgtata gcatacatta tacgaagtta tg                        42

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 23
gatccataac ttcgtataat gtatgctata cgaagttat                            39

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 24
tcgagacgtc ataacttcgt atagcataca ttatacgaag ttatgc                    46

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic

<400> SEQUENCE: 25
gccgcataac ttcgtataat gtatgctata cgatgttatg acgtc                     45

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 26
catggctata acttcgtata gcatacatta tacgaagtta tg                        42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 27
gatccataac ttcgtataat gtatgctata cgaagttata gc                        42

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 28
aaatttctcg aggctctgag caaaagctca t                                    31

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 29
tatatatagc ggccgcttaa ttaagatcct cctcggata                            39

<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: Synthetic

<400> SEQUENCE: 30
ccagaggagg aggctgccat taggcgtgaa aatgaatggg ctgaagaccg tctgagcaaa     60
agctcatttc                                                            70
```

```
<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:  Synthetic

<400> SEQUENCE: 31
ggatatagtt cctcctttca gc                                              22

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence:  Synthetic

<400> SEQUENCE: 32
attacctcat atagcataca ttatacgaag ttat                                 34
```

RAPID SUBCLONING USING SITE-SPECIFIC RECOMBINATION

This is a Continuation-in-Part of U.S. patent application Ser. No. 08/864,224, filed Feb. 28, 1997, now U.S. Pat No. 5,851,808.

FIELD OF THE INVENTION

The invention relates to recombinant DNA technology. In particular, the invention relates to compositions, including vectors, and methods for the rapid subcloning of nucleic acid sequences in vivo and in vitro.

BACKGROUND OF THE INVENTION

Molecular biotechnology has revolutionized the production of protein and polypeptide compounds of pharmacological importance. The advent of recombinant DNA technology permitted for the first time the production of proteins on a large scale in a recombinant host cell rather than by the laborious and expensive isolation of the protein from tissues which may only contain minute quantities of the desired protein (e.g., isolation of human growth hormone from cadaver pituitary). The production of proteins, including human proteins, on a large scale in a heterologous host requires the ability to express the protein of interest in the heterologous host. This process typically involves isolation or cloning of the gene encoding the protein of interest followed by transfer of the coding region into an expression vector that contains elements (e.g., promoters) which direct the expression of the desired protein in the heterologous host cell. The most commonly used means of transferring or subcloning a coding region into an expression vector involves the in vitro use of restriction endonucleases and DNA ligases. Restriction endonucleases are enzymes which generally recognize and cleave a specific DNA sequence in a double-stranded DNA molecule. Restriction enzymes are used to excise the coding region from the cloning vector and the excised DNA fragment is then joined using DNA ligase to a suitably cleaved expression vector in such a manner that a functional protein may be expressed.

The ability to transfer the desired coding region to an expression vector is often limited by the availability or suitability of restriction enzyme recognition sites. Often multiple restriction enzymes must be employed for the removal of the desired coding region and the reaction conditions used for each enzyme may differ such that it is necessary to perform the excision reactions in separate steps. In addition, it may be necessary to remove a particular enzyme used in an initial restriction enzyme reaction prior to completing all restriction enzyme digestions; this requires a time-consuming purification of the subcloning intermediate. Ideal methods for the subcloning of DNA molecules would permit the rapid transfer of the target DNA molecule from one vector to another in vitro or in vivo without the need to rely upon restriction enzyme digestions.

SUMMARY OF THE INVENTION

The present invention provides reagents and methods which comprise a system for the rapid subcloning of nucleic acid sequences in vivo and in vitro without the need to use restriction enzymes.

The present invention provides a method for the recombination of nucleic acid constructs, comprising: providing a first nucleic acid construct comprising, in operable order, an origin of replication, a first sequence-specific recombinase target site, and a nucleic acid of interest, a second nucleic acid construct comprising, in operable order, an origin of replication, a regulatory element and a second sequence-specific recombinase target site adjacent to and downstream from the regulatory element, and a site-specific recombinase; contacting the first and the second nucleic acid constructs with the site-specific recombinase under conditions such that the first and second nucleic acid constructs are recombined to form a third nucleic acid construct, wherein the nucleic acid of interest is operably linked to the regulatory element. The present invention contemplates the use of any type of regulatory element. In some embodiments of the present invention, the regulatory element comprises a promoter element, a fusion peptide (e.g., an affinity domain), or an epitope tag. In preferred embodiments, the nucleic acid of interest comprises a gene.

In some embodiments, the first nucleic acid construct further comprises a selectable marker.- In other embodiments, the second nucleic acid construct further comprises a selectable marker. The present invention contemplates that the first and second nucleic acid constructs both comprise selectable markers. In preferred embodiments the selectable markers of the first and second nucleic acid constructs are different from one another. Selectable markers include, but are not limited to a kanamycin resistance gene, an ampicillin resistance gene, a tetracycline resistance gene, a chloramphenicol resistance gene, a streptomycin resistance gene, a spectinomycin resistance gene, the aadA gene, the $\Phi$X174 E gene, the strA gene, and the sacB gene.

In preferred embodiments, the first nucleic acid construct further comprises a prokaryotic termination sequence. Prokaryotic termination sequences include, but are en not limited to the T7 termination sequence. In other preferred embodiments, the first nucleic acid construct further comprises a eukaryotic polyadenylation sequence. Polyadenylation sequences include, but are not limited to, the bovine growth hormone polyadenylation sequence, the simian virus 40 polyadenylation sequence, and the Herpes Simplex virus thymidine kinase polyadenylation sequence. In yet other preferred embodiments, the first nucleic acid construct further comprises a conditional origin of replication.

In preferred embodiments of the present invention, the first and second sequence-specific recombinase target sites are selected from the group consisting of loxP, loxP2, loxP3, loxP23, loxP511, loxB, loxC2, loxL, loxR, lox$\Delta$86, lox$\Delta$117, frt, dif, loxH and att. The present invention contemplates that the first and second sequence-specific recombinase target sites may comprise the same sequence or may comprise different sequences.

In yet other embodiments of the present invention, the first nucleic acid construct further comprises a polylinker.

The present invention contemplates that the recombination methods can be used in vitro and in vivo. In some in vivo embodiments, the site-specific recombinase is provided by a host cell expressing the site-specific recombinase. In some in vivo methods, the contacting of the first and the second nucleic acid constructs with the site-specific recombinase comprises introducing the first and said second nucleic acid constructs into a host cell under conditions such that the third nucleic acid construct is capable of replicating in the host cell.

The present invention further provides methods for precise transfer of nucleic acid molecules by recombination. In some embodiments, the first nucleic acid construct further comprises a third sequence-specific recombinase target site and said second nucleic acid constructs further comprises a fourth sequence-specific recombinase target site. In preferred embodiments, the first sequence-specific recombinase and the third sequence-specific recombinase in the first nucleic acid construct are located on opposite sides of the nucleic acid of interest. It is contemplated that the first and third sequence-specific recombinase target sites are contiguous with, adjacent to, or distant from the nucleic acid of interest. In particularly preferred embodiments the third and fourth sequence-specific recombinase target sites are selected from the group consisting of RS sites and Res sites, although other target sites are contemplated by the present invention. In some embodiments of the this method of the present invention, the first nucleic acid construct further comprises a third sequence-specific recombinase target site and the second nucleic acid constructs further comprises a fourth sequence-specific recombinase target site, wherein the method further comprises providing a second site-specific recombinase and the step of contacting the third nucleic acid construct with the second site-specific recombinase under conditions such that the third nucleic acid construct is recombined to form a fourth and a fifth nucleic acid construct.

The present invention also provides a recombined nucleic acid construct prepared according to any of the above methods.

The present invention further provides a method for the recombination of nucleic acid constructs, comprising: providing a vector, a linear nucleic acid molecule comprising a sequence complementary to at least a portion of said vector, and an E. coli host cell, wherein said host cell comprises an endogenous recombination system, a loss of function rec mutation, a suppressor, and a loss of function endogenous restriction modification system mutation; and introducing the vector and the linear nucleic acid molecule into the host cell under conditions such that the linear nucleic acid molecule and the vector are recombined to form a recombinant nucleic acid construct. In preferred embodiments the loss of function rec mutation is selected from the group consisting of recBC and recD. In other preferred embodiments, the suppressor comprises sbc. In yet other preferred embodiments, the loss of function endogenous restriction modification system mutation comprises hsdR.

The present invention further provides a method for generating a nucleic acid fusion on the 3' end of the nucleic acid of interest in the first nucleic acid construct from above, comprising: providing a tagged linear nucleic acid sample comprising a tag to be added to the 3' end of the nucleic acid of interest, and a sequence complementary to a region of the first nucleic acid construct that is 3' of the nucleic acid of interest; and a host cell capable of endogenous homologous recombination of complementary nucleic acid molecules; and introducing the tagged linear nucleic acid sample and the first nucleic acid construct into the host cell under conditions such that the tagged linear nucleic acid sample and the first nucleic acid construct are recombined to form a tagged nucleic acid construct.

The present invention further provides a method for the cloning of nucleic acid libraries, comprising: providing a plurality of first nucleic acid constructs comprising, in operable order, an origin of replication, a first sequence-specific recombinase target site, and a nucleic acid member from a nucleic acid library, a plurality of second nucleic acid construct comprising, in operable order, an origin of replication, a regulatory element and a second sequence-specific recombinase target site adjacent to and downstream from the regulatory element, and a site-specific recombinase; contacting the plurality of first and second nucleic acid constructs with the site-specific recombinase under conditions such that the plurality of first and second nucleic acid constructs are recombined to form a plurality of third nucleic acid constructs, wherein the nucleic acid members from the nucleic acid library are operably linked to the regulatory elements. The present invention further provides a nucleic acid library prepared according to the above method.

The present invention also provides a method for the directional cloning of a nucleic acid molecule, comprising: providing first and second portions of a regulatory element, a first nucleic acid molecule comprising the first portion of the regulatory element; and a second nucleic acid molecule comprising the second portion of the regulatory element; and combining the first and the second nucleic acid molecules to produce a third nucleic acid molecule under conditions whereby an intact regulatory element is produced from the combination of the first and the second portions of the regulatory element, wherein the presence of the intact regulatory element in the third nucleic acid molecule indicates a direction of cloning of the first nucleic acid molecule with respect to the second nucleic acid molecule.

The present invention also provides a method for the directional cloning of a nucleic acid molecule, comprising providing: the nucleic acid molecule to be cloned, a first primer comprising sequence complementary to the nucleic acid molecule, a second primer comprising sequence complementary to the nucleic acid molecule and sequence corresponding to a first portion of a lacO site, amplification means, and a target nucleic acid molecule comprising a second portion of the lacO site; amplifying the nucleic acid molecule with the first and second primers to produce a modified nucleic acid molecule comprising the first portion of a lacO site; and ligating the modified nucleic acid molecule into the target nucleic acid such that, when cloned in the desired direction, an intact lacO site is produced. In some embodiments, the method further comprises the step of detecting the intact lacO site. In particularly preferred embodiments, the target nucleic acid molecule comprises pUNI-30.

The present invention further provides a method for regulated recombination in host cells that constitutively express a recombinase, comprising: providing a host cell expressing a recombinase, a first nucleic acid construct comprising an origin of replication, a first site-specific recombinase site, a second site-specific recombinase site that differs in sequence from the first site-specific recombinase site such that the recombinase will not initiate recombination between the first and second site-specific recombinase sites, and a selectable marker gene between the first and second site-specific recombinase sites, and a second nucleic acid construct comprising an origin of replication, a third site-specific recombinase target site, and a fourth site-specific recombinase target site that differs in sequence from the third site-specific recombinase site such that the recombinase will not initiate recombination between the third and fourth site-specific recombinase sites; and introducing the first and second nucleic acid constructs into the host cell under conditions such that the first and second nucleic acid constructs are recombined. In some embodiments, the method further comprises the step of selecting for a desired recombinant nucleic acid molecule using the selectable marker. In preferred embodiments, the first nucleic acid construct is a Univector. In alternative preferred embodiments, the second nucleic acid construct is a Univector.

The present invention also provides, a nucleic acid construct comprising, in operable order: a conditional origin of replication; a sequence-specific recombinase target site having a 5' and a 3' end; and a unique restriction enzyme site, said restriction enzyme site located adjacent to the 3' end of the sequence-specific recombinase target site. In some embodiments, the construct further comprises a prokaryotic termination sequence. In yet other embodiments, the construct further comprises a eukaryotic polyadenylation sequence. The present invention contemplates the use of any prokaryotic termination sequence and any eukaryotic polyadenylation sequence. In preferred embodiments, the construct fruitier comprises one or more selectable marker genes. Selectable marker genes include, but are not limited to the kanamycin resistance gene, the ampicillin resistance gene, the tetracycline resistance gene, the chloramphenicol resistance gene, the streptomycin resistance gene, the strA gene, and the sacB gene. In preferred embodiments, the sequence-specific recombinase target site is selected from the group consisting of loxP, loxP2, loxP3, loxP23, loxP511, loxB, loxC2, loxL, loxR, loxΔ86, loxΔ117, frt, dif, loxH and att.

In some embodiments the construct further comprises a gene of interest inserted into the unique restriction enzyme site. In particular embodiments, the construct has the nucleotide sequence set forth in SEQ ID NO: 1 (FIG. 26A). In other embodiments, the construct further comprises a second sequence-specific recombinase target site. In preferred embodiments, the second sequence-specific recombinase target site is selected from the group consisting of RS site and a Res site. In yet other embodiments, the construct further comprises a polylinker.

The present invention further provides a nucleic acid construct comprising in 5' to 3' operable order: an origin of replication; a promoter element having a 5' and a 3 end; and a sequence-specific recombinase target site having a 5' and a 3' end. In some embodiments, the construct further comprises a selectable marker gene.

The present invention also provides a nucleic acid construct comprising in operable order: a promoter element having a 5' and a 3' end; a first sequence-specific recombinase target site having a 5' and a 3' end, wherein the 3' end of the promoter element is located upstream of the 5' end of the sequence-specific recombinase target site; a gene of interest joined to the 3' end of the sequence-specific recombinase target site such that a functional translational reading frame is created; a conditional origin of replication; a first selectable marker gene; a second sequence-specific recombinase target site; and an origin of replication. In some embodiments, the construct further comprises a second selectable marker gene.

The present invention also provides a method for the recombination of nucleic acid constructs, comprising: providing a first nucleic acid construct comprising a loxH site, a second nucleic acid construct comprising a loxH site; and a site-specific recombinase; and contacting the first and the second nucleic acid constructs with the site-specific recombinase under conditions such that the first and second nucleic acid constructs are recombined. The present invention also provides a recombed nucleic acid construct prepared according to the above method.

DESCRIPTION OF THE DRAWINGS

FIG. 13 provides the nucleotide sequence of the wild-type loxP site (SEQ ID NO:12), the loxP2 site (SEQ ID NO:13), the loxP3 site (SEQ ID NO:14) and the loxP23 site (SEQ ID NO:15).

FIG. 18 shows the expression of UPS-derived baculovirus expression constructs in insect cells.

FIG. 19 shows immunblotting with anti-HA antibodies of Hela cells expressing Myc-tagged F-box protein under the control of the CMV promoter.

FIG. 21 shows restriction digestion assays of sample that underwent POT with SKP1 replacing the E gene in pAS2-E.

FIG. 26 shows the sequence for: A) SEQ ID NO:1; B) SEQ ID NO:10; and C) SEQ ID NO:11.

DEFINITIONS

Figure 1:
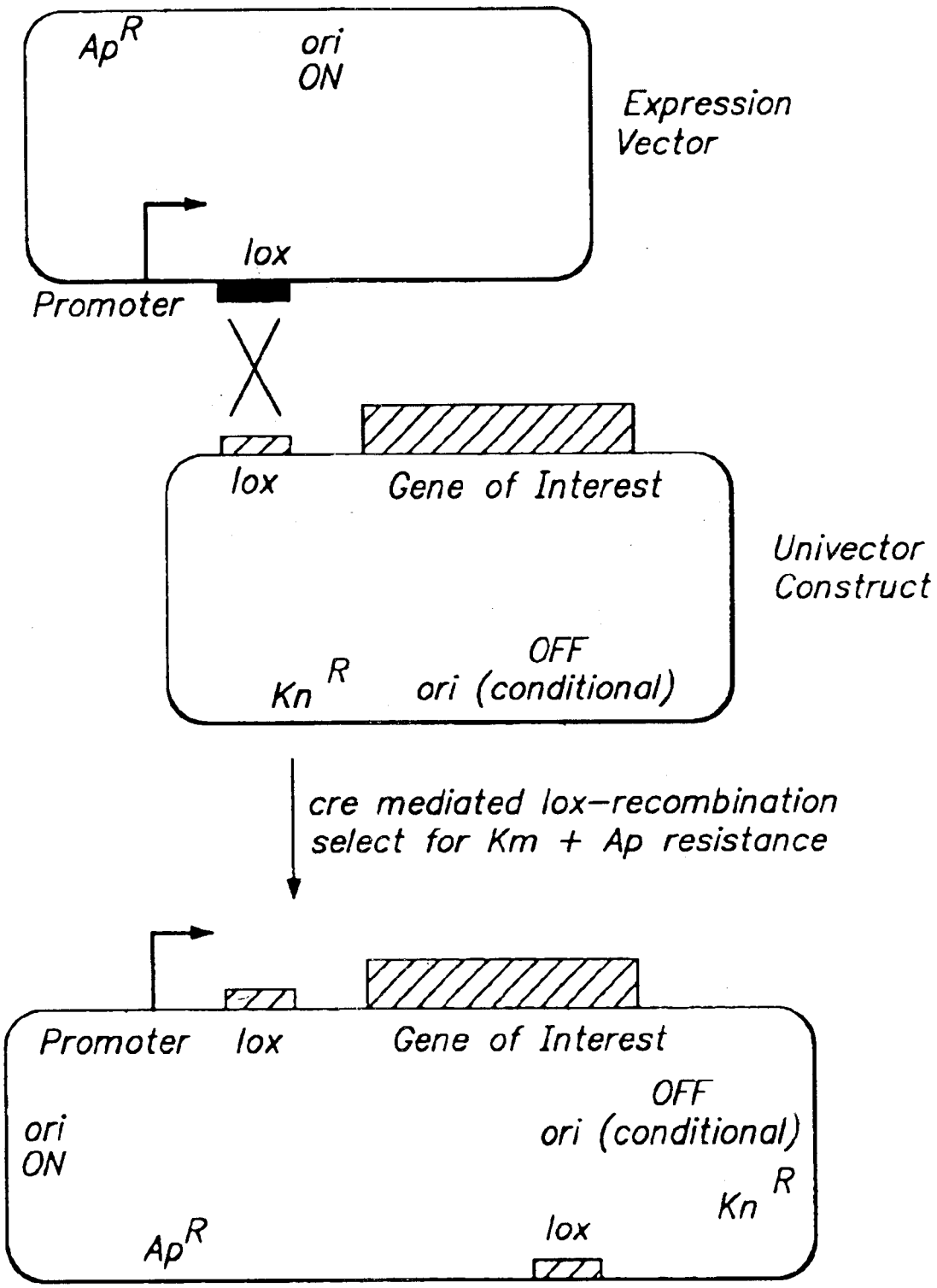
FIG. 1 provides a schematic illustrating certain elements of the pUNI vectors and the Univector Fusion System.

To facilitate understanding of the invention, a number of terms are defined below.

As used herein, "a conditional origin of replication" refers to an origin of replication that requires the presence of a functional trans-acting factor (e.g., a replication factor) in a prokaryotic host cell. Conditional origins of replication include, but are not limited to, temperature-sensitive replicons such as rep pSC101$^{ts}$.

As used herein, the term "origin of replication" refers to an origin of replication that is functional in a broad range of prokaryotic host cells (i.e., a normal or non-conditional origin of replication such as the ColE1 origin and its derivatives).

The terms "sequence-specific recombinase" and "site-specific recombinase" refer to enzymes that recognize and bind to a short nucleic acid site or sequence and catalyze the recombination of nucleic acid in relation to these sites.

The terms "sequence-specific recombinase target site" and "site-specific recombinase target site" refer to a short nucleic acid site or sequence which is recognized by a sequence- or site-specific recombinase and which become the crossover regions during the site-specific recombination event. Examples of sequence-specific recombinase target sites include, but are not limited to, lox sites, frt sites, att sites and dif sites.

The term "lox site" as used herein refers to a nucleotide sequence at which the product of the cre gene of bacteriophage P1, Cre recombinase, can catalyze a site-specific recombination. A variety of lox sites are known to the art including the naturally occurring loxP (the sequence found in the P1 genome), loxB, loxL and loxR (these are found in the E. coli chromosome) as well as a number of mutant or variant lox sites such as loxP511, loxΔ86, loxΔ117, loxC2, loxP2, loxP3, loxP23, loxS, and loxH.

The term "frt site" as used herein refers to a nucleotide sequence at which the product of the FLP gene of the yeast 2 μm plasmid, FLP recombinase, can catalyze a site-specific recombination.

The term "unique restriction enzyme site" indicates that the recognition sequence for a given restriction enzyme appears once within a nucleic acid molecule.

For example, the EcoRI site is a unique restriction enzyme site within the plasmid pUNI-10 (SEQ ID NO:1).

A restriction enzyme site is said to be located "adjacent to the 3' end of a sequence-specific recombinase target site" if the restriction enzyme recognition site is located downstream of the 3' end of the sequence-specific recombinase target site. The adjacent restriction enzyme site may, but need not, be contiguous with the last or 3' nucleotide comprising the sequence-specific recombinase target site. For example, the EcoRI site of pUNI-10 is located adjacent (within 3 nucleotides) to the 3' end of the loxP site (see FIG. 2B); the XhoI, NdeI, and NcoI sites are also adjacent (i.e., within about 10–150 nucleotides) to the loxP site but these sites are not contiguous with the 3' end of the loxP site in pUNI-10.

The terms "polylinker" or "multiple cloning site" refer to a cluster of restriction enzyme sites on a nucleic acid construct which are utilized for the insertion and/or excision of nucleic acid sequences such as the coding region of a gene, lox sites, etc.

The term "prokaryotic termination sequence" refers to a nucleic acid sequence which is recognized by the RNA polymerase of a prokaryotic host cell and results in the termination of transcription. Prokaryotic termination sequences commonly comprise a GC-rich region that has a twofold symmetry followed by an AT-rich sequence [Stryer, supra]. A commonly used prokaryotic termination sequence is the T7 termination sequence. A variety of termination sequences are known to the art and may be employed in the nucleic acid constructs of the present invention including, but not limited to, the $T_{INT}$, $T_{L1}$, $T_{L2}$, $T_{L3}$, $T_{R1}$, $T_{R2}$, $T_{6S}$ termination signals derived from the bacteriophage lambda [Lambda II, Hendrix et al. Eds., supra] and termination signals derived from bacterial genes such as the trp gene of E. coli [Stryer, supra].

The term "eukaryotic polyadenylation sequence" (also referred to as a "poly A site" or "poly A sequence") as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [J. Sambrook, supra, at 16.6–16.7]; numerous vectors contain the SV40 poly A signal [e.g., pCEP4, pREP4, pEBVHis (Invitrogen)]. Another commonly used heterologous poly A signal is derived from the bovine growth hormone (BGH) gene; the BGH poly A signal is available on a number of commercially available vectors [e.g., pcDNA3.1, pZeoSV2, pSecTag (Invitrogen)]. The poly A signal from the Herpes simplex virus thymidine kinase (HSV tk) gene is also often used as a poly A signal on expression vectors. Vectors containing the HSV tk poly A signal include the pBK-CMV, pBK-RSV, and pOP13CAT vectors from Stratagene.

As used herein, the terms "selectable marker" or "selectable marker gene" refers to the use of a gene which encodes an enzymatic activity that confers the ability to grow in medium lacking what would otherwise be an essential nutrient (e.g., the TRP1 gene in yeast cells). In addition, a selectable marker may confer resistance to an antibiotic or drug upon the cell in which the selectable marker is expressed. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose and the ΦX174 E gene). Selectable markers used in this manner are referred to as negative selectable markers or counter-selectable markers.

As used herein, the term "vector" is used in reference to nucleic acid molecules that transfer DNA segment(s) from one cell to another. The term "vehicle" is sometimes used interchangeably with "vector." A "vector" is a type of "nucleic acid construct." The term "nucleic acid construct" includes circular nucleic acid constructs such as plasmid constructs, phagemid constructs, cosmid vectors, etc. as well as linear nucleic acid constructs (e.g., λ phage constructs and PCR products). The nucleic acid construct may comprise expression signals such as a promoter and/or an enhancer (in such a case it is referred to as an expression vector).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "transformation" and "transfection" as used herein refer to the introduction of foreign DNA into prokaryotic or eukaryotic cells. Transformation of prokaryotic cells may be accomplished by a variety of means known to the art including the treatment of host cells with $CaCl_2$ to make competent cells, electroporation, etc. Transfection of eukaryotic cells may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics, among other means.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that comprises segments of DNA joined together by means of molecular biological techniques.

The term "recombinant protein" or "recombinant polypeptide" as used herein refers to a protein molecule that is expressed from a recombinant DNA molecule.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The 3' end of a promoter element is said to be located upstream of the 5' end of a sequence-specific recombinase target site when (moving in a 5' to 3' direction along the nucleic acid molecule) the 3' terminus of a promoter element (the transcription start site is taken as the 3' end of a promoter element) precedes the 5' end of the sequence-specific recombinase target site. The 3' end of the promoter element may be located adjacent (generally within about 0 to 500 bp) to the 5' end of the sequence-specific recombinase target site. Such an arrangement is used when the pHOST vector is not intenrded to permit the expression of a translational fusion with the gene of interest donated by a pUNI vector. Alternatively, when the pHOST vector is intended to permit the expression of a translational fusion, the 3' end of the promoter element is located upstream of both the sequences encoding the amino-terminus of a fusion protein and the 5' end of the sequence-specific recombinase target site. In this case, the 5' end of the sequence-specific recombinase target site is located within the coding region of the fusion protein (e.g., located downstream of both the promoter element and the sequences encoding the affinity domain, such as Gst).

As used herein, the phrase "an oligonucleotide having a nucleotide sequence encoding a gene" refers to a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription [Maniatis, T. et al., *Science* 236:1237 (1987)]. Promoter and enhancer elements have been isolated from a variety of eukaryotic sources including genes in yeast, insect, and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review, see Voss, S. D. el al., *Trends Biochem. Sci.*, 11:287 (1986) and Maniatis, T. et al., supra (1987)]. For example, the SV40 early gene enhancer is very active in a wide variety of cell types from many mammalian species and has been widely used for the expression of proteins in mammalian cells [Dijkema, R. et al., *EMBO J.* 4:761 (1985)]. Two other examples of promoter/enhancer elements active in a broad range of mammalian cell types are those from the human elongation factor 1α gene [Uetsuki, T. et al., *J Biol. Chem.*, 264:5791 (1989), Kim, D. W. et al., *Gene* 91:217 (1990) and Mizushima, S. and Nagata, S., *Nuc. Acids. Res.*, 18:5322 (1990)] and the long terminal repeats of the Rous sarcoma virus [Gorman, C. M. et al., *Proc. Natl. Acad Sci. USA* 79:6777 (1982)] and the human cytomegalovirus [Boshart, M. et al., *Cell* 41:521 (1985)].

As used herein, the term "promoter/enhancer" denotes a segment of DNA that contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al, *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high copy number (up to $10^4$ copies/cell) in cells that express the appropriate viral T antigen. Vectors that contain the replicons from bovine papillomavirus or Epstein-Barr virus replicate extrachromosomally at low copy number (~100 copies/cell).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and the including sequences located adjacent to the coding region on both the 5' and 3' ends such that the gene corresponds to the length of the full-length mRNA. The sequences that are located 5' of the coding region and which are present on the MRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript. Introns therefore are absent in the messenger RNA (mRNA) transcript. The mRNA functions during translation to specify the sequence or order of amino acids in a nascent polypeptide. When a gene is altered such that its product is no longer biologically active in a wild-type fashion, the mutation is referred to as a "loss-of-function" mutation. When a gene is altered such that a portion or the entirety of the gene is deleted or replaced, the mutation is referred to as a "knockout" mutation.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage, and polyadenylation.

As used herein, the term "purified" or "to purify" refers to the removal of contaminants from a sample. For example, recombinant Cre polypeptides are expressed in bacterial host cells (e.g., as a Gst-Cre fusion protein) and the Cre polypeptides are purified by the removal of at least a portion of the host cell proteins; the percent of recombinant Cre polypeptides is thereby increased in the sample.

The term "native protein" is used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (e.g., the Cre protein) joined to an exogenous protein fragment (e.g., the fusion partner which consists of non-Cre protein sequences). The fusion partner may enhance solubility of the protein of interest as expressed in a host cell, may provide an affinity tag to allow purification of the recombinant fusion protein from the host cell or culture supernatant, or both, among other desired characteristics. If desired, the fusion protein may be removed from the protein of interest by a variety of enzymatic or chemical means known to the art.

DESCRIPTION OF THE INVENTION

The present invention provides compositions and methods that comprise a system for the rapid subcloning of nucleic acid sequences in vivo and in vitro without the need to use restriction enzymes. This system is referred to as the Univector Fusion System or Univector Plasmid-fusion System (UPS). The UPS employs site-specific recombination to catalyze plasmid fusion between a Univector (i.e., a plasmid containing a gene of interest) and host vectors containing regulatory information. In some embodiments of the present invention, plasmid fusion events are genetically selected and result in placement of the gene of interest under the control of novel regulatory elements. A second UPS-related method of the present invention allows for the precise transfer of coding sequences alone from a Univector into a host vector. UPS further provides means for the subcloning of entire nucleic acid libraries and the directional cloning of linear nucleic acid molecules (e.g., PCR products).

The UPS offers many advantages over previously available technologies for the manipulation of genes. For example, for a routine analysis of a new gene, it may be desirable to express it in bacteria as a glutathione-S-transferase (Gst) or polyhistidine fusion for purification and antibody production, to fuse it to the DNA-binding domain of GAL4 or lexA for two hybrid analysis, to express it from the T7 promoter to allow generation of a riboprobe or mRNA for in vitro transcription and translation, and express it in baculovirus, all in the course of a single study. One might also wish to express the gene under the regulation of different promoters in a variety of organisms or to mark it with different epitope tags to facilitate subsequent biochemical or immunological analysis. All of these manipulations consume significant amounts of time and energy using previous available technologies for two reasons. First, each of the different vectors required for these studies were, for the most part, developed independently and thus contain different sequences and restriction sites for insertion of genes. Therefore, genes must be individually tailored to adapt to each of these vectors. Secondly, the DNA sequence of any given gene varies and can contain internal restriction sites that make it incompatible with particular vectors, thereby complicating manipulation. The advent of the polymerase chain reaction (PCR) has greatly facilitated the alteration of gene sequences and creation of compatible restriction sites for subcloning purposes. However, the high error rate of thermostable polymerases requires the sequence of each PCR-derived DNA fragment to be verified, a time consuming process.

The availability of whole genome sequences now provides the opportunity to analyze large sets of genes for both genetic and biochemical properties. The need to perform parallel processing of large gene sets exponentially amplifies the current defects associated with conventional cloning methods. The methods and compositions of the present invention provide a series of recombination-based approaches that significantly reduce the time and effort involved in generating multiple transcriptional and translational fusions for gene analysis and cDNA library construction. The present invention provides a system whereby a gene can be placed under the control of any of a variety of promoters or fused in frame to other proteins or peptides without the use of restriction enzymes. As discussed above, the UPS uses site-specific recombination to fuse two plasmids at a unique sequence adjacent to both a regulatory region and the 5' end of the gene or interest, thereby placing the gene under new regulation. This system, together with the other methods and compositions of the present invention discussed herein, provide a multifaceted approach for the rapid and efficient generation and manipulation of recombinant DNA, thus making possible parallel processing of whole genome sets of coding sequences.

The basis of the UPS is a vector termed the "Univector" or the "pUNI" vector into which sequences encoding a gene of interest (cDNA or genomic) are inserted. The pUNI vector has a sequence-specific recombinase target site, such as a loxP site, preceding the insertion site for the gene of interest, a selectable marker gene (this feature is optional) and a conditional origin of replication that is active only in host cells expressing the requisite trans-acting replication factor (this feature is optional). The pUNI vectors are designed to contain a gene of interest but lack a promoter for the expression of the gene of interest. The gene of interest may be cloned directly into the pUNI vector (i.e., the pUNI vector may be used as a cloning vector, particularly for the cloning of cDNA libraries) or a previously cloned gene of interest may be inserted (i.e., subcloned) into the pUNI vector.

Using a sequence-specific recombinase (e.g., Cre recombinase), a precise fusion of the pUNI vector into a second vector containing another sequence-specific recombinase target site is catalyzed. The second vector, referred to generically as a "pHOST" vector, is a vector (e.g., expression vector) that contains the sequence-specific recombinase target site downstream of regulatory element (e.g., a promoter) contained within the pHOST vector. Following the site-specific recombination event which occurs between the single sequence-specific recombinase target sites located on each vector (e.g., the pUNI vector and the pHOST vector), the two vectors are stably fused in a manner that places the gene of interest under the control of the regulatory element contained within the pHOST vector. When used for transfer into an expression vector, this fusion event also occurs in a manner that retains the proper translational reading frame of the gene of interest.

In some embodiment of the present invention, the fusion or recombination event can be selected for by selecting for the ability of host cells, which do not express a trans-acting replication factor required for replication of a conditional origin contained on the pUNI vector, to acquire a selectable phenotype conferred by the selectable marker gene (if present) on the pUNI vector. In these embodiments, the pUNI vector cannot replicate in cells that do not express the trans-acting replication factor and therefore, unless the pUNI vector has integrated into the second vector that contains a non-conditional origin of replication, pUNI will be lost from the host cell.

The Univector Fusion System allows any number of expression or fusion constructs containing the gene of interest present on the pUNI vector to be made rapidly (e.g., within a single day). Using conventional cloning or subcloning techniques which employ restriction enzyme digestion(s), the production of a single expression vector containing a gene of interest can take several days (i e., for the design and construction of each expression vector). In contrast, with the methods and compositions of the present invention, once a battery of expression vectors modified to contain the appropriate sequence-specific recombinase target site is made, a gene of interest can be transferred to any number of expression vectors in an afternoon using the Univector Fusion System. For example, FIG. 1 provides a schematic illustrating the straightforward recombination methods of the pUNI vectors and the Univector Fusion System.

The present invention further provides methods and compositions for directional subcloning of PCR fragments and other nucleic acid molecules into Univectors or other vectors and methods and compositions for generation of epitope tags and other fusions at the 3' end of open reading frames using homologous recombination.

In general, UPS can be used to fuse any coding region of interest either with a specific promoter to gain novel transcriptional regulation, with another coding sequence to produce a fusion protein with novel properties (e.g., an epitope tag for immunological detection or a DNA binding domain or transcriptional activation domain for two hybrid analysis), or with any other desired regulatory element. As discussed above, the UPS eliminates the need for restriction enzymes, DNA ligases, and many in vitro manipulations required for subcloning. This relieves the constraints on cloning vectors with respect to DNA sequence and size since the UPS reaction is independent of vector size or sequence. Furthermore, the time-consuming processed inherent in conventional cloning such as the identification of a suitable vector, designing a cloning strategy, restriction endonuclease digestion, agarose gel electrophoresis, isolation of DNA fragments, and the ligation reaction is shortened to a 20 minute UPS reaction. Due to the uniform nature of the UPS reaction and its simplicity, dozens of constructs can be made simultaneously by simply using different recipient vectors. In addition, in contrast to restriction enzymes and DNA ligases, recombinases (e.g., Gst-Cre) can be made inexpensively in large quantities. These features will save investigators significant amounts of time and expense.

Together, these methods constitute a comprehensive recombinational strategy for the generation and manipulation of recombinant DNA that can be used for the parallel processing of gene sets, an ability required for genomic analyses.

a) Conditional Origins of Replication and Suitable Host Cells

In some embodiments of the present invention, the pUNI vector comprises a conditional origin of replication. Conditional origins of replication are origins that require the presence or expression of a trans-acting factor in the host cell for replication. A variety of conditional origins of replication functional in prokaryotic hosts (e.g., *E. coli*) are known to the art. The present invention is illustrated with, but not limited by, the use of the R6Kγ origin, oriR, from the plasmid R6K. The R6Kγ origin requires a trans-acting factor, the II protein supplied by the pir gene [Metcalf et al. (1996) Plasmid 35:1]. *E. coli* strains containing the pir gene will support replication of R6Kγ origins to medium copy number. A strain containing a mutant allele of pir, pir-116, will allow an even higher copy number of constructs containing the R6Kγ origin (i.e., 15 copies per cell for the wild type versus 250 copies per cell for the mutant). This property may be useful when potentially toxic genes are manipulated, although the chances of expression of a toxic gene are low because, in preferred embodiments of the present invention, the Univector either contains no promoter or contains a promoter driving the neo gene which is transcribed in the opposite direction from the gene of interest.

*E. coli* strains that express the pir or pir-116 gene product include BW18815 (ATCC 47079; this strain contains the pir-116 gene), BW19094 (ATCC 47080; this strain contains the pri gene), BW20978 (this strain contains the pir-16 gene), BW20979 (this strain contains the pir gene), BW21037 (this strain contains the pir-116 gene) and BW21038 (this strain contains the pir gene) (Metcalf et al., supra).

Other conditional origins of replication suitable for use on the pUNI vectors of the present invention include, but are not limited to:

1) the RK2 oriV from the plasmid RK2 (ATCC 37125). The RK2 oriV requires a trans-acting protein encoded by the trfA gene [Ayres et al. (1993) *J Mol Biol*. 230:174];
2) the bacteriophage P1 ori which requires the repA protein for replication [Pal et al. (1986) *J Mol. Biol*. 192:275];
3) the origin of replication of the plasmid pSC101 (ATCC 37032) which requires a plasmid encoded protein, repA, for replication [Sugiura en al. (1992) *J Bacteriol*. 175: 5993]. The pSC101 ori also requires IHF, an *E. coli* protein. *E. coli* strains carrying the himA and himD (hip) mutants (the him and hip genes encode subunits of IHF) cannot support pSC101 replication [Stenzel et al. (1987) *Cell* 49:709];
4) the bacteriophage lambda ori which requires the lambda O and P proteins [Lambda II, Hendrix et al. Eds., Cold Spring Harbor Press, Cold Spring Harbor, N.Y. (1983)];
5) pBR322 and other ColE1 derivatives will not replicate in polA mutants of *E. coli* and therefore, these origins of replication can be used in a conditional manner [Grindley and Kelley (1976) *Mol Gen. Genet*. 143:311]; and
6) replication-thermosensitive plasmids such pSU739 or pSU300 which contain a thermosensitive replicon derived from plasmid pSC101, rep pSC101$^{ts}$ which comprises oriV [Mendiola and de la Cruz (1989) *Mol. Microbiol*. 3:979 and Francia and Lobo (1996) *J Bact*. 178:894]. pSU739 and pSU300 are stably maintained in *E. coli* strain DH5α (Gibco BRL) at a growth temperature of 30° C. (42° C. is non-permissive for replication of this replicon).

Other conditional origins of replication, including other temperature sensitive replicons, are known to the art and may be employed in the vectors and methods of the present invention.

b) Sequence-Specific Recombinases And Target Recognition Sites

The precise fusion between the pUNI vector and the expression vector is catalyzed by a site-specific recombinase. Site-specific recombinases are enzymes that recognize a specific DNA site or sequence (referred to herein generically as a "sequence-specific recombinase target site") and catalyze the recombination of DNA in relation to these sites. Site-specific recombinases are employed for the recombination of DNA in both prokaryotes and eukaryotes. Examples of site-specific recombination include, but are not limited to: 1) chromosomal rearrangements that occur in *Salmonella typhimurium* during phase variation, inversion of the FLP sequence during the replication of the yeast 2 μm circle, and in the rearrangement of immunoglobulin and T cell receptor genes in vertebrates, 2) integration of bacteriophages into the chromosome of prokaryotic host cells to form a lysogen, and 3) transposition of mobile genetic elements (e.g., transposons) in both prokaryotes and eukaryotes. The term "site-specific recombinase" refers to enzymes that recognize short DNA sequences that become the cross-over regions during the recombination event and includes recombinases, transposases, and integrases.

Figures 14, 15:
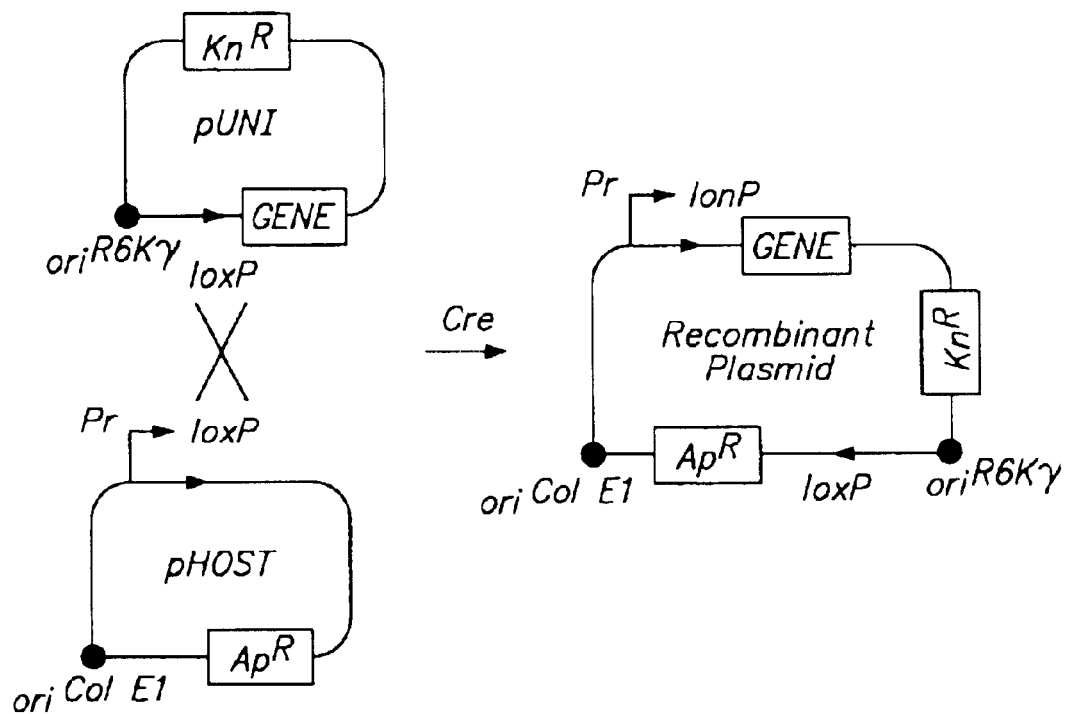
FIG. 14 shows a schematic for one embodiment of Cre-mediated plasmid fusion.
FIG. 15 shows data demonstrating the efficiency of Gst-Cre recombinase activity as measured by UPS.

The present invention is illustrated with, but not limited by, the use of vectors containing lox sites (e.g., loxP sites) and the recombination of these vectors using the Cre recombinase of bacteriophage P1. The Cre protein catalyzes recombination of DNA between two loxP sites and is involved in the resolution of P1 dimers generated by replication of circular lysogens [Stemberg et al. (1981) Cold Spring Harbor Symp. Quant. Biol. 45:297]. Cre can function in vitro and in vivo in many organisms including, but not limited to, bacteria, fungi, and mammals [Abremski et al. (1983) *Cell* 32:1301; Sauer (1987) *Mol Cell. Biol.* 7:2087; and Orban et al. (1992) *Proc. Natl. Acad. Sci.* 89:6861]. A schematic for one embodiment of Cre-mediated plasmid fusion is shown in FIG. 14. In this figure, the Univector, pUNI, is the plasmid into which the gene of interest is inserted and pHOST represents the recipient vector that contains the appropriate transcriptional and/or translational regulatory sequences that will eventually control the expression of the gene of interest. A recombinant expression construct is made through Cre-loxP-mediated site-specific recombination that fuses these two plasmids. This in vitro reaction generates a dimeric recombinant plasmid in which the gene of interest from pUNI is placed downstream of the promoter present on the host vector. In this example, the recombinant plasmid in FIG. 14 can be selected in a pir bacterial strain by selecting Kn$^r$.

The loxP sites may be present on the same DNA molecule or they may be present on different DNA molecules; the DNA molecules may be linear or circular or a combination of both. The loxP site consists of a double-stranded 34 bp sequence (SEQ ID NO: 12) which comprises two 13 bp inverted repeat sequences separated by an 8 bp spacer region [Hoess et al. (1982) *Proc. Natl. Acad Sci. USA* 79:3398 and U.S. Pat. No. 4,959,317, the disclosure of which is herein incorporated by reference]. The internal spacer sequence of the loxP site is asymmetrical and thus, two loxP sites can exhibit directionality relative to one another [Hoess et al. (1984) *Proc. Natl Acad Sci. USA* 81:1026]. When two loxP sites on the same DNA molecule are in a directly repeated orientation, Cre excises the DNA between these two sites leaving a single loxP site on the DNA molecule [Abremski et al. (1983) *Cell* 32:1301]. If two loxP sites are in opposite orientation on a single DNA molecule, Cre inverts the DNA sequence between these two sites rather than removing the sequence. Two circular DNA molecules each containing a single loxP site will recombine with one another to form a mixture of monomer, dimer, trimer, etc. circles. The concentration of the DNA circles in the reaction can be used to favor the formation of monomer (lower concentration) or multimeric circles (higher concentration).

Circular DNA molecules having a single loxP site will recombine with a linear molecule having a single loxP site to produce a larger linear molecule. Cre interacts with a linear molecule containing two directly repeating loxP sites to produce a circle containing the sequences between the loxP sites and a single loxP site and a linear molecule containing a single loxP site at the site of the deletion.

The Cre protein has been purified to homogeneity [Abremski et al. (1984) *J Mol. Biol.* 259:1509] and the cre gene has been cloned and expressed in a variety of host cells [Abremski et al (1983), supra]. Purified Cre protein is available from a number of suppliers (e.g., Novagen and New England Nuclear/DuPont).

The Cre protein also recognizes a number of variant or mutant lox sites (variant relative to the loxP sequence), including the loxB, loxL and loxR sites which are found in the *E. coli* chromosome [Hoess et al. (1982), supra]. Other variant lox sites include loxP511 [5'-ATAACTTCGTATA GTATAC<u>AT</u>TATACGAAGTTAT-3' (SEQ ID NO: 16); spacer region underlined; Hoess et al. (1986), supra], and loxC2 [5'-<u>ACAAC</u> TTCGTATA ATGTATGCTATACGAAGTTAT-3' (SEQ ID NO: 17); spacer region underlined; U.S. Pat. No. 4,959,317]. Cre catalyzes the cleavage of the lox site within the spacer region and creates a six base-pair staggered cut [Hoess and Abremski (1985) *J Mol Biol.* 181:351]. The two 13 bp inverted repeat domains of the lox site represent binding sites for the Cre protein. If two lox sites differ in their spacer regions in such a manner that the overhanging ends of the cleaved DNA cannot reanneal with one another, Cre cannot efficiently catalyze a recombination event using the two different lox sites. For example, it has been reported that Cre cannot recombine (at least not efficiently) a loxP site and a loxP511 site; these two lox sites differ in the spacer region. Two lox sites which differ due to variations in the binding sites (i.e., the 13 bp inverted repeats) may be recombined by Cre provided that Cre can bind to each of the variant binding sites. The efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxP site, as these two lox sites differ by a single nucleotide in the left binding site.

A variety of other site-specific recombinases may be employed in the methods of the present invention in place of the Cre recombinase. Alternative site-specific recombinases include, but are not limited to:

1) the FLP recombinase of the 2 μ plasmid of *Saccharomyces cerevisiae* [Cox (1983) *Proc. Nail. Acad Sci. USA* 80:4223] which recognizes the frt site. Like the loxP site, the frt site comprises two 13 bp inverted repeats separated by an 8 bp spacer [5' - GAAGTTC-CTATT<u>CTCTAGAAA</u>GTATAGG AACTTC-3' (SEQ ID NO: 18); spacer underlined]. The FLP gene has been cloned and expressed in *E. coli* (Cox, supra) and in mammalian cells (PCT International Patent Application PCT/US92/01899, Publication No.: WO 92/15694, the disclosure of which is herein incorporated by reference) and has been purified [Meyer-Lean et al. (1987) *Nucleic Acids Res.* 15:6469; Babineau et al. (1985) *J Biol. Chem.* 260:12313; and Gronostajski and Sadowski (1985) *J Biol. Chem.* 260:12328];

2) the Int recombinase of bacteriophage lambda (with or without Xis) which recognizes att sites (Weisberg et al. In: Lambda II, supra, pp. 211–250);

3) the xerC and xerD recombinases of *E. coli* which together form a recombinase that recognizes the 28 bp dif site [Leslie and Sherratt (1995) *EMBO J* 14:1561];
4) the Int protein from the conjugative transposon Tn916 [Lu and Churchward (1994) *EMBO J*. 13:1541];
5) TpnI and the β-lactamase transposons [Levesque (1990) *J Bacteriol*. 172:3745];
6) the Tn3 resolvase [Flanagan et al. (1989) *J Mol. Biol*. 206:295 and Stark et al. (1989) *Cell* 58:779];
7) the SpoIVC recombinase of *Bacillus subtilis* [Sato et al. (1990) *J Bacteriol* 172:1092];
8) the Hin recombinase [Galsgow et al. (1989) *J Biol Chem*. 264:10072];
9) the Cin recombinase [Hafter et al. (1988) *EMBO J* 7:3991]; and
10) the immunoglobulin recombinases [Malynn et al. *Cell* (1988) 54:453].

c) Modification of Expression Vectors

As discussed above, pUNI vectors are used to transfer a gene of interest into a suitably modified vector via site-specific recombination. The modified vectors or host vectors used in the Univector Fusion System are referred to as pHOST vectors. pHOST vectors are generally expression vectors (e.g., plasmids) which have been modified by the insertion of a sequence-specific recombinase target site (e.g., a lox site). However, the pHOST can comprise any regulatory sequence desired for manipulation of nucleic acids. The presence of the sequence-specific recombinase target site on the pHOST plasmid permits the rapid subcloning or insertion of the gene interest contained within a pUNI vector to generate an expression vector capable of expressing the gene of interest. In some embodiments of the present invention, the pHOST vector may encode a protein domain such as an affinity domain including, but not limited to, glutathione-S-transferase (Gst), maltose binding protein (MBP), a portion of staphylococcal protein A (SPA), a polyhistidine tract, etc. A variety of commercially available expression vectors encoding such affinity domains are known to the art. The affinity domain may be located at either the amino- or carboxy-terminus of the fusion protein. When the pHOST plasmid contains a vector-encoded affinity domain, a fusion protein comprising the vector-encoded affinity domain and the protein of interest is generated when the pUNI and pHOST vectors are recombined.

To generate expression vectors intended to generate transcriptional fusions (i.e., pHOST does not contain a vector-encoded protein domain), a sequence-specific recombinase target site is placed after (i.e., downstream of) the start of transcription in the host vector. This is easily accomplished using synthetic oligonucleotides comprising the desired sequence-specific recombinase target site. In designing the oligonucleotide comprising the sequence-specific recombinase target site, care is taken to avoid introducing an ATG or start codon that might initiate translation inappropriately.

To generate expression vectors intended to generate a fusion protein between a vector-encoded protein domain located at the amino-terminus of the fusion protein and the protein of interest (encoded by the gene of interest contained within the pUNI vector) (i.e., a translational fusion), care is taken to place the sequence-specific recombinase target site in the correct reading frame such that: 1) an open reading frame is maintained through the sequence-specific recombinase target site on pHOST, and 2) the open reading frame in the sequence-specific recombinase target site on pHOST is in frame with the open reading frame found on the sequence-specific recombinase target site contained within the pUNI vector. In addition, the oligonucleotide comprising the sequence-specific recombinase target site on pHOST is designed to avoid the introduction of in-frame stop codons. The gene of interest contained within the pUNI vector is cloned in a particular reading frame so as to facilitate the creation of the desired fusion protein.

The modification of several expression vectors is provided in the examples below to illustrate the creation of suitable pHOST vectors. At present, approximately 40 pHOST vectors have been generated, including GST expression vectors, yeast GAL1 expression vectors, mammalian CMV expression vectors, and baculovirus expression vectors. In each case, expression was at or near the levels achieved by conventional cloning. A general strategy for generating any pHOST of interest involves the generation of a linker containing the desired sequence-specific recombinase target site (e.g., a lox site such as loxP or loxH) by annealing two complementary oligonucleotides. The annealed oligonucleotides form a linker having sticky ends that are compatible with ends generated by restriction enzymes whose sites are conveniently located in the parental expression vector (e.g., within a polylinker of the parental expression vector). Thus, any vector can be easily adapted for use with the UPS method.

d) In Vitro Recombination

The fusion of a pUNI vector and a pHOST vector is accomplished in vitro using a purified preparation of a site-specific recombinase (e.g., Cre recombinase). The pUNI vector and the pHOST vector are placed in reaction vessel (e.g., a microcentrifuge tube) in a buffer compatible with the site-specific recombinase to be used. For example, when a Cre recombinase (native or a fusion protein form) is employed, the reaction buffer may comprise 50 mM Tris-HCl (pH 7.5), 10 mM $MgCl_2$, 30 mM NaCl and 1 mg/ml BSA. When a FLP recombinase is employed, the reaction buffer may comprise 50 mM Tris-HCl (pH 7.4), 10 mM $MgCl_2$, 100 μg/ml BSA [Gronostajski and Sadowski, supra]. The concentration of the pUNI vector and the pHOST vector may vary between 100 ng to 1.0 μg of each vector per 20 μl reaction volume with about 0.1 μg of each nucleic acid construct (0.2 μg total) per 20 μl reaction being preferred. The concentration of the site-specific recombinase may be titered under a standard set of reaction conditions to find the optimal concentration of enzyme to be used as described in, Example 4.

Following the in vitro fusion reaction, a portion of the reaction mixture is used to transform a suitable host cell to permit the recovery and propagation of the fused vectors. In some embodiments of the present invention, the host cell employed will not express the trans-acting factor required for replication of the conditional origin of replication contained within the pUNI vector (or alternatively the host cell will be grown at a temperature which is non-permissive for replication of a temperature sensitive replicon contained within the pUNI vector). The host cells will be grown under conditions that select for the presence of the selectable marker contained within the pUNI vector (e.g., growth in the presence of kanamycin when the pUNI vector contains a kanamycin resistance gene). Plasmid or non-chromosomal DNA is isolated from host cells which display the desired phenotype and subjected to restriction enzyme digestion to confirm that the desired fusion event has occurred.

e) Recombination in Prokaryotic Host Cells

The fusion of a pUNI vector and a pHOST vector may be accomplished in vivo using a host cell that expresses the appropriate site-specific recombinase (e.g., Cre recombinase). The host cell may express the recombinase as part of its genome or may be supplied with means for expressing the recombinase (e.g., a recombinase expression vector). In embodiments of the present invention that employ a pUNI vector with a conditional origin of replication, the host cell employed lack the ability to express the trans-acting factor required for replication of the conditional origin of replication (or alternatively the host cell will be grown at a temperature which is non-permissive for replication of a temperature sensitive replicon contained within the pUNI vector).

The pUNI vector and the pHOST vector are cotransformed into the host cell using a variety of methods known to the art (e.g., transformation of cells made competent by treatment with $CaCl_2$, electroporation, etc.). The cotransformed host cells are grown under conditions that select for the presence of the selectable marker contained within the pUNI vector (e.g., growth in the presence of kanamycin when the pUNI vector contains the kanamycin resistance gene). Plasmid or non-chromosomal DNA is isolated from host cells which display the desired phenotype and subjected to restriction enzyme digestion to confirm that the desired fusion event has occurred.

f) Precise ORF Transfer (POT)

UPS results in the fusion of two plasmids and is suitable for the vast majority of expression needs. In rare cases where the size of the recombinant molecule is limiting (e.g., in the generation of retrovirus or adeno-associated viral [AAV] expression constructs), it might be desirable to transfer only the gene of interest and not the approximately 2 kb remainder of the Univector. To accomplish this, a second recombination event is utilized. In some embodiments of the present invention, this second recombination is catalyzed by the R recombinase [Araki et al. (1992) *J Mol. Biol.* 225:25] that allows a resolution of the UPS generated heterodimer as described in Example 9, although a variety of second recombinases will find use with the present invention (e.g., the Res system). POT function in vivo and in vitro. It is recommended that POT only be used in those cases where size is a limitation.

In some embodiments of the present invention, a standard UPS method is utilized to generate a dimer containing the entire pUNI and pHOST vectors, followed by a reaction with the second recombinase that excises the unwanted portions of the Univector. Alternatively, host cells or reaction conditions can be applied that allow both recombination reactions to occur in a single step (See Example 9). Cells containing the desired recombinant product can be selected for by using selectable markers, and/or conditional origins of replication.

g) Generation of 3' Gene Fusions on the Univector

While UPS greatly facilitates the generation of fusion proteins at the N-terminus of the protein of interest, it is often necessary to modify proteins on the C-terminus (e.g., to add an epitope tag). To facilitate this class of modification, the present invention takes advantage of *E. coli*'s endogenous homologous recombination system. It has been shown [Winans et al. (1985) *J Bacteriol* 161:1219] that *E. coli* strains mutant for recBC, but containing a suppressor sbc, could take up linear DNA and recombine it onto the *E. coli* chromosome or resident plasmids, much as has been shown for *S. cerevisiae*. recD mutants have been shown to behave in a similar manner [Russell et al. (1989) *J Bacteriol.* 171:2609]. However, such systems have not been used for recombinant cloning in *E. coli*. In fact, these systems are incompatible with many cloning protocols, as the endogenous restriction modification systems of the cell would digest the samples to be cloned.

Figure 25:
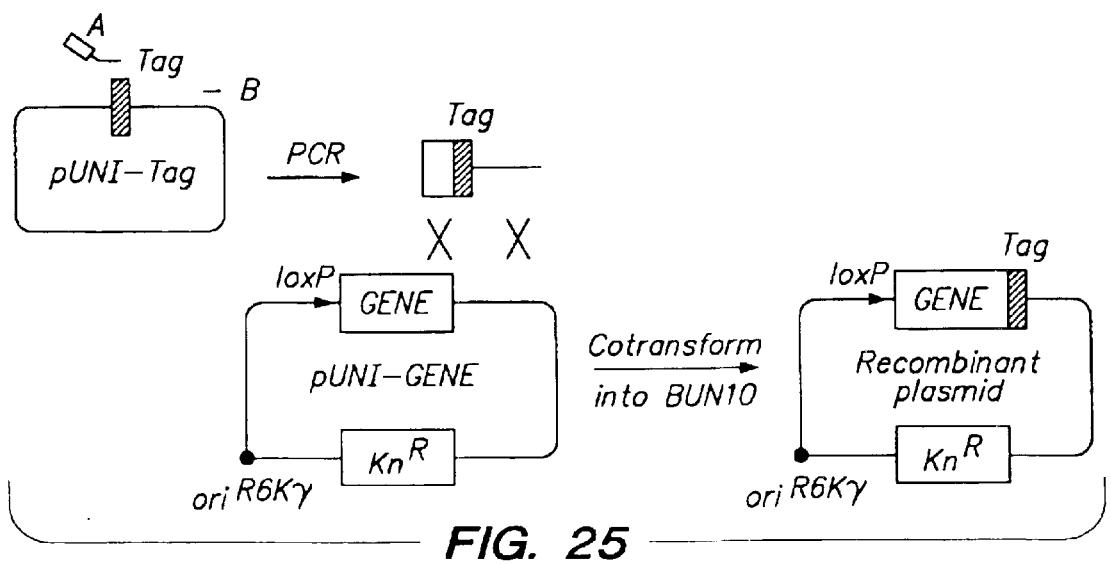
FIG. 25 shows a schematic of a gap repair scheme for modification of the 3' end of coding regions using homologous recombination.

The present invention provides means to overcome these problems and to provide for effective cloning and recombination (e.g., with the UPS). To facilitate recombination onto Univector plasmids, the present invention provides BUN10, a recBCsbcBhsdR strain expressing pir-116. The hsdR mutation prevents restriction of nucleic acid (e.g., PCR amplified DNA) by the endogenous restriction modification system of *E. coli*. In one embodiment of the present invention, this system was tested using a 3×MYC epitope tag and the SKP1 gene in pUNI-10 as the recipient. pML74, which is pUNI-Amp containing a triple (3×) MYC epitope tag followed by a stop codon, was used as template DNA for PCR amplification with two primers, A and B. Primer A (SEQ ID NO:30) is 71 nt long, the first 50 nt of which correspond to the last 50 nt of the SKP1 coding region and the last 21 nt, the 3' end of the primer, correspond to the first 21 nt of the DNA encoding the 3×MYC tag. The reading frames of SKP1 and the 3×MYC tag are in register. Primer B (SEQ ID NO:31) is 22 nt long and recognizes a site on pML74 common to pUNI vectors that begins 367 bp from the polylinker region. Amplification using primers A and B and pML74 as a template generated a fragment of DNA with 50 bp homology to the Univector. This amplification product was co-transformed with BamHI-SacI-cleaved pUNI-SKP1 into BUN10 cells and $Kn^r$ transformants were selected and analyzed by restriction mapping. Homologous recombination events are selected because they allow the recircularization of the linearized vector. A schematic representation of this method is provided in FIG. 25. Ten percent of $Kn^r$ transformants resulted in homologous recombination at the C-terminus of the SKP1 gene to generate a SKP1-3×MYC tag. This experiment demonstrates that homologous recombination in *E. coli* can be used to alter the sequence of genes in 3' regions adjacent to restriction sites.

Furthermore, it is clear that this method is generally applicable to broader cloning strategies. Although the example above describes the use of an amplification product for recombination into the pUNI vector, any nucleic acid sample with sufficient sequence complementarity can be used. Thus, the sample to be inserted could be artificially synthesized or prepared by any other means. Additionally, the recombination event can be designed to occur at any desired location on any desired recipient vector (i.e., is not limited to the production of 3' gene fusions).

h) Method for Directional Subcloning into pUNI Vectors

When cloning blunt ended nucleic acid molecules, such as those generated by thermostable polymerases, it is desirable to have a way of identifying desired recombinant molecules (e.g., vectors containing the insert in a desired orientation). This is of great relevance to the UPS because the initial cloning of genes into pUNI will often utilize PCR amplified material. To facilitate this process, the present invention provides a method for directional subcloning into vectors (e.g., pUNI derivatives) that relies upon the generation of a reconstituted regulatory element from two partial sites located on the fragment to be cloned and the recipient vector, respectively. For example, a linear nucleic acid molecule to be inserted into a vector can be designed with a portion of a promoter at its 3' or 5' ends. The recipient vector is then designed with the remainder of the promoter, arranged such that, when the cloned fragment is inserted in the desired direction, an intact promoter is reconstituted and provides a means of detecting the successful directional cloning event.

It is clear that a variety of reconstituted regulatory elements can be employed to achieve detectable directional cloning. For example, reconstituted regulatory elements that find use with the present invention include, but are not limited to, promoters, repressors, operators, enhancers, enzyme recognitions sites, selectable markers, and conditional origins of replication, among others. It is also contemplated that the reconstituted regulatory element may comprise a negative selection capability, such that fragments cloned in an undesired orientation reconstitute the regulatory element and are selected against. One skilled in the art will recognize the wide range of regulatory elements and applications that can be applied to this system.

Figure 22A:
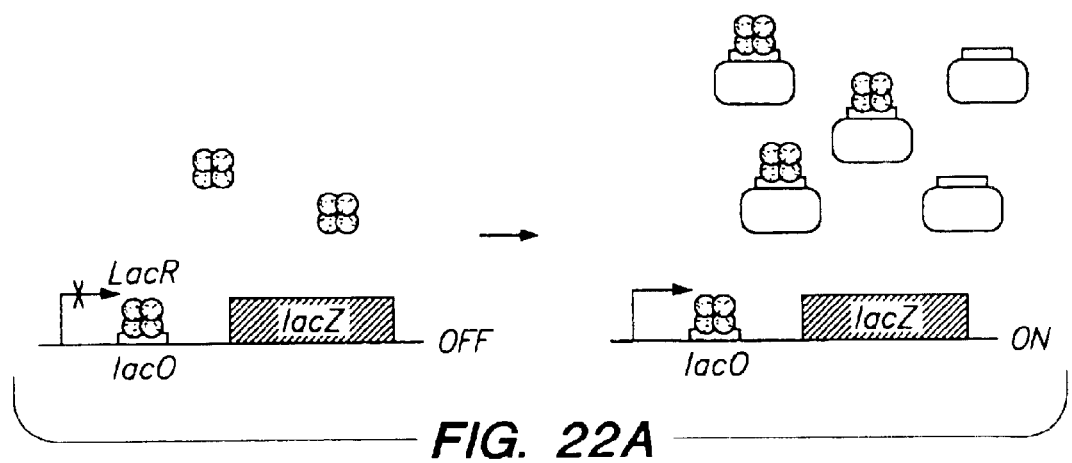
FIGS. 22A–C shows schematic of a method for directional subcloning of nucleic acid samples into a Univector.

To demonstrate the effectiveness of the above approach, the lac operator was employed to direct directional subcloning events. Luria and colleagues observed in the early 1960s that phage carrying the binding site for the lac repressor, lacO, could induce the expression of the endogenous lacZ gene by titrating out a limited number of repressor proteins [Miller and Reznikoff, Eds. (1978) *The Operon*, Cold Spring Harbor Laboratory, Cold Spring Harbor, N.Y.] and this was shown to be true when lacO was present on high copy number plasmids [Marians et al. (1976) *Nature* 263:744; and Heyneker et al (1976) *Nature* 263:748], as illustrated in FIG. 22A. FIG. 22A shows a schematic representation of normal conditions in the absence of inducer (left diagram) where lacR is bound to the lac operator sites in front of lacZ and represses transcription. In the presence of high copy number plasmid containing the lacO sequence (right diagram), LacR repressors are titrated out by binding to plasmid borne lacO sites and the endogenous lacZ gene is expressed.

Figure 22B:
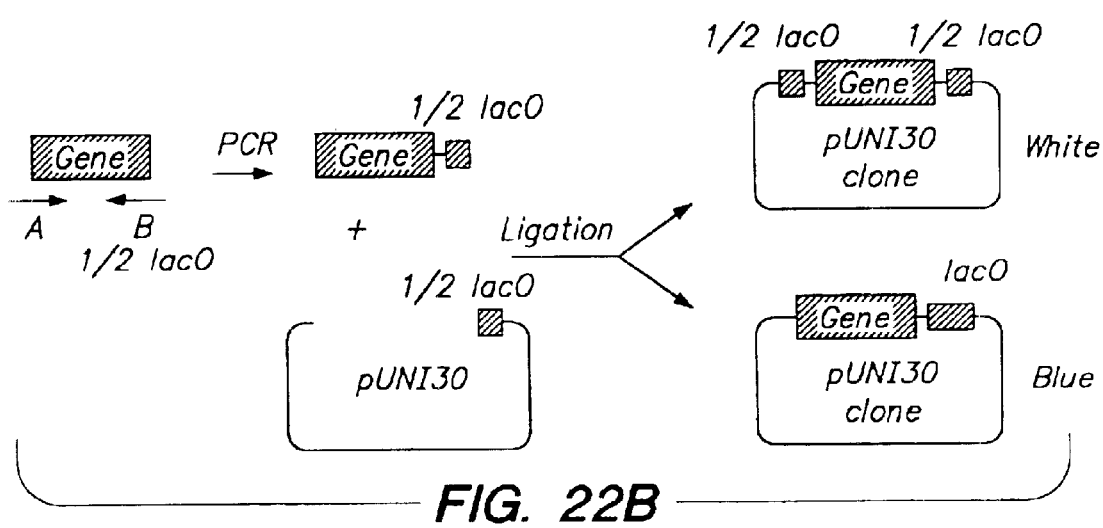
Figure 22C:
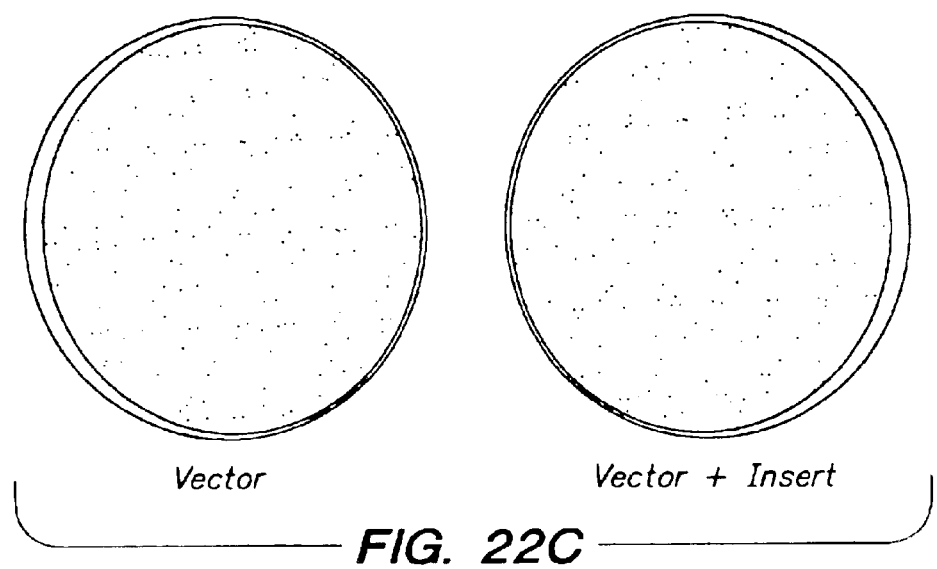

This observation was taken advantage of by the methods of the present invention, whereby the 3' half of a lacO site was placed on a pUNI vector (i.e., pUNI-30). The lacO derivative used was a symmetrical 20 bp site that has a Eco47III site at the center. To utilize this method for cloning PCR derived material, primers were made corresponding to the SKP1 gene A 10 bp sequence corresponding to the 5' half of the symmetrical lacO sequence (shown in FIG. 22B) was added to the 5' end of the 3' primer. FIG. 22B shows this strategy, whereby primer A (5') and B (3') are used to amplify the gene of interest. The 5' end of primer B contains a half lacO site which subsequently becomes the 3-end of the PCR fragment indicated in the Figure. After ligating the PCR fragment into linearized pUNI-30 containing the other half of lacO, an intact lacO site is reconstituted and, in Lac$^+$ cells, results in induction of endogenous β-galactosidase and production of blue colonies in the presence of X-Gal. The PCR fragment was ligated into Eco47III-cleaved pUNI-30 and transformed into BUN10, a Lac$^+$ *E. coli* strain, and Kn$^r$ colonies were selected on plates containing X-gal. Plasmids containing SKP1 in the proper orientation were identified by their dark blue color (shown by arrows in FIG. 22C). Reclosure of the vector without insert as well as the presence of the PCR fragment in the incorrect orientation result in the production of white or pale blue colonies. Ten out of 10 dark blue colonies contained SKP1 in the correct orientation. In particularly preferred embodiments, phosphorylated PCR primers are used. In other preferred embodiments, Taq polymerase is used, and the material is preferably treated briefly with T4 polymerase and dNTPs to remove the 3' overhangs generated.

i) Library Transfer Using UPS

In addition to permitting the rapid transfer of a gene of interest from a particular pUNI vector containing a gene of interest into a pHOST vector, the Univector Fusion System permits the rapid exchange of an entire cDNA library to a variety of expression vectors. This capability to essentially transform one library into many libraries is one of the most significant advances made possible by the UPS methods provided by the present invention. The high efficiency of the in vitro UPS reaction (i.e., a minimum of 16.8%) coupled with the extremely high efficiency of modem transformation methods makes possible the conversion of whole cDNA libraries constructed in the Univector into expression libraries without loss of representation. Thus, it is contemplated that single cDNA libraries will be converted into any of a number of different expression libraries such as those used in the two hybrid systems [Durfee et al. (1993) *Gene. & Dev.* 7:55; and Aronheim et al. (1997) *Mol. Cell. Biol.* 17:3094], for complementation cloning in yeast [Elledge et al. (1991) *Proc. Natl. A cad. Sci.* 88:1731], mammalian expression systems [Okayama and Berg (1982) *Mol Cell. Biol.* 2:161], etc. Thus, the present invention provides methods such that libraries made for one purpose will no longer need to be remade from scratch when needed in a different context; clones isolated from these libraries are easily converted back into simple Univector plasmids compatible with other pHOST vectors for future analysis.

In these methods, the cDNA library is generated using a pUNI vector as the cloning vector (a pUNI library). The entire library may then be transferred (using either an in vitro or an in vivo recombination reaction) into any expression vector modified to contain a sequence-specific recombinase target site (e.g., a lox site) (i.e., into a pHOST vector). This solves an existing problem in the art, in that there is no way, using existing vector systems, to exchange the inserts in a library made in one expression vector en masse (i.e., as an entire library) to a different expression vector. Example 10 provides an illustration of such capabilities using methods of the present invention.

In addition, the sequences contained within a pUNI library can be used to recombine with linear x constructs (which can then be used to isolate specific genes by complementation of appropriate host cell such as *E. coli* or *S. cerevisiae* mutant cells). For example, UPS is compatible with the λYES series of lambda cloning vectors that use cre-lox recombination to convert phage clones into plasmids. These vectors are capable of making extremely large cDNA libraries (i.e., greater than $10^8$ recombinants per 100 ng of cDNA) and, unlike plasmid libraries, can be propagated with minimal loss of representation. Further as described in Example 7, the in vivo gene trap method, a variation of the Univector Fusion System, can be used to transfer linear DNA fragments that lack a selectable marker, such as a PCR product, into a variety of expression vectors.

An extremely important application of the UPS method is in the manipulation of whole genome sets of coding regions. For organisms whose genomes have been sequenced, a complete set of identified ORFS, or "Unigene" set, can be constructed in the Univector and be systematically converted by UPS into any kind of expression library. Also, the simplicity and uniformity of the UPS reaction makes it readily amenable to automation for systematic conversion of arrayed clones. This greatly expedites the functional characterization of whole genomes and help further the progression of genome projects into proteome projects.

EXPERIMENTAL

The following examples serve to illustrate certain preferred embodiments and aspects of the present invention and are not to be construed as limiting the scope thereof.

In the experimental disclosure which follows, the following abbreviations apply: ° C. (degrees Centigrade); g (gravitational field); vol (volume); DNA (deoxyribonucleic acid); RNA (ribonucleic acid); kdal or kD (kilodaltons); OD (optical density); EDTA (ethylene diamine tetra-acetic acid); *E. coli* (*Escherichia coli*); SDS (sodium dodecyl sulfate);

PAGE (polyacrylamide gel electrophoresis); ts (temperature sensitive); p (plasmid); LB (Luria-Bertani medium: per liter: 10 g Bacto-tryptone, 5 g yeast extract, 10 g NaCl, pH to 7.5 with NaOH); ml (milliliter); µl (microliter); M (Molar); mM (millimolar); µM (microMolar); g (gram); µg (microgram); ng (nanogram); U (units), mU (milliunits); min. (minutes); sec. (seconds); % (percent); bp (base pair); kb (kilobase); PCR (polymerase chain reaction); Tris (tris (hydroxymethyl)-aminomethane); PMSF (phenylmethylsulfonylfluoride); BSA (bovine serum albumin); IPTG (isopropyl-β-D-thiogalactoside); ORF (open reading frame); ATCC (American Type Culture Collection, Rockville, Md.); Bio-Rad (Bio-Rad Corp., Hercules, Calif.); Invitrogen (Invitrogen, Corp., San Diego, Calif.); New England Nuclear/Du Pont (Boston, Mass.); Novagen (Novagen, Inc., Madison, Wis.); Pharmacia or Pharmacia Biotech (Pharmacia Biotech, Piscataway, N.J.); Pharmingen (PharMingen, San Diegi, Calif.); Gibco BRL (Gaithersburg, Md.); and Stratagene (Stratagene Cloning Systems, La Jolla, Calif.).

EXAMPLE 1

Construction of Univector Constructs

Figure 23A:
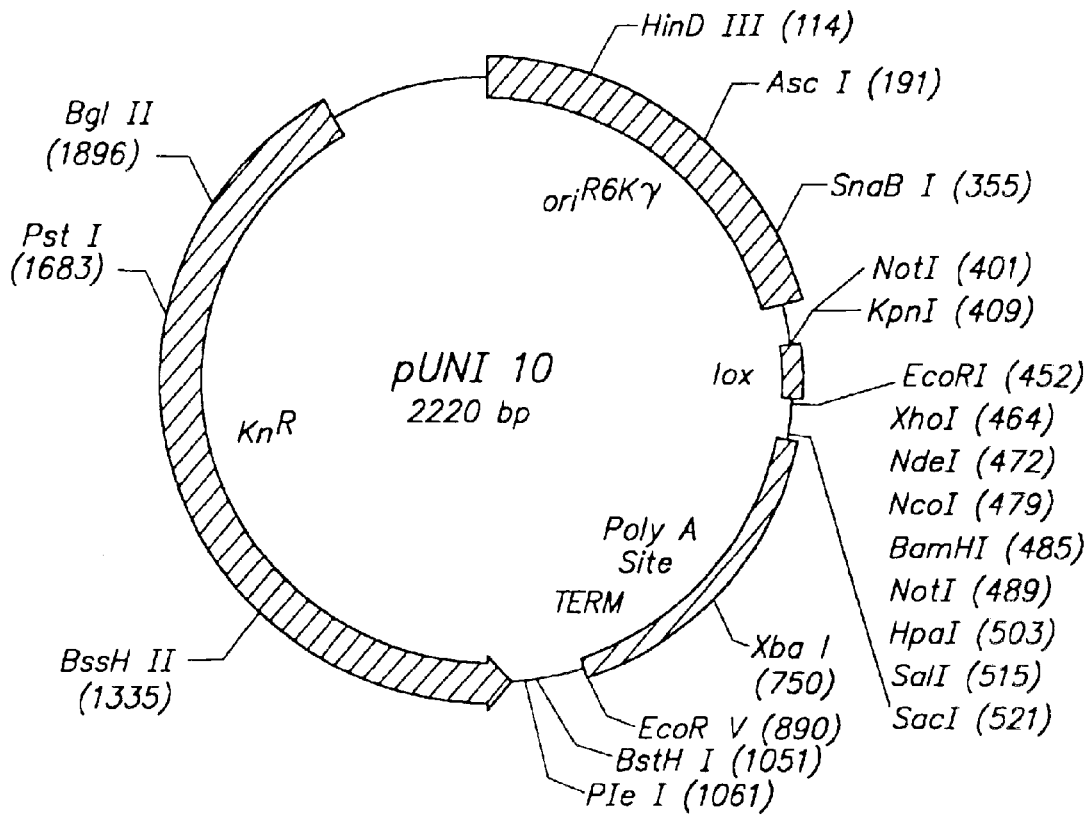
FIG. 23 provides a schematic map of the pUNI-10, pUNI-20, and pUNI-30 vectors.
Figure 23B:
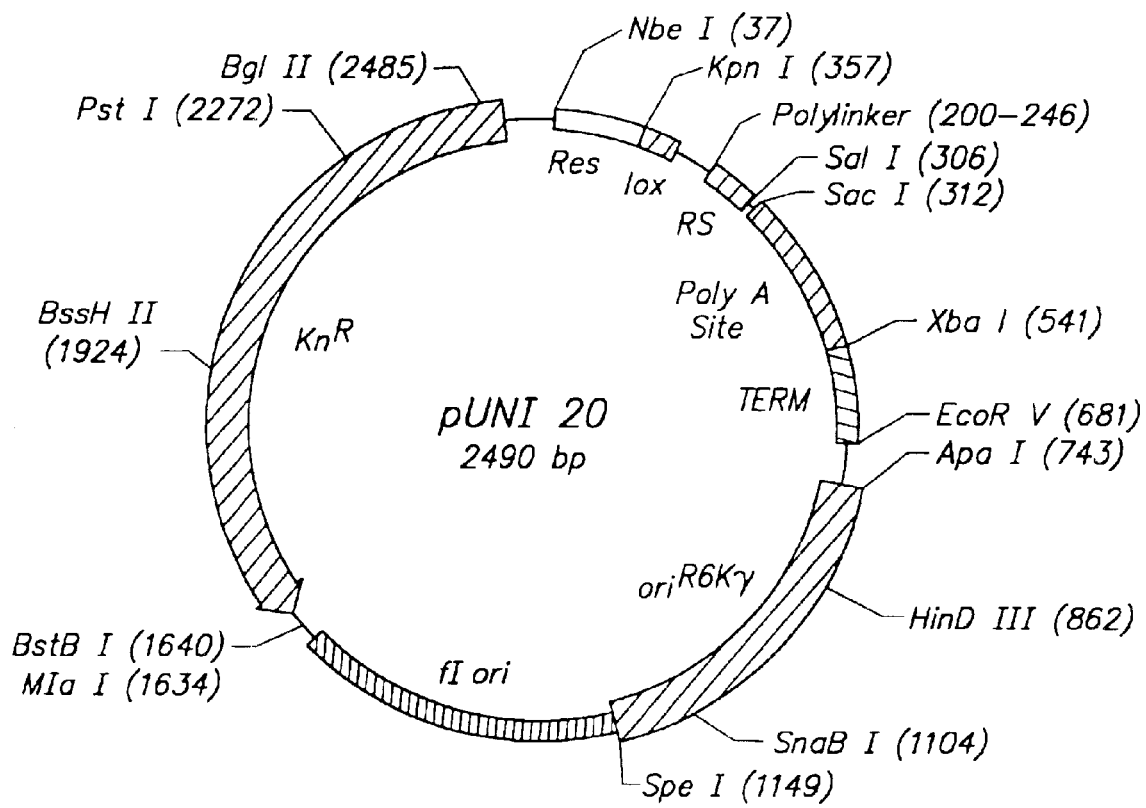
Figure 23C:
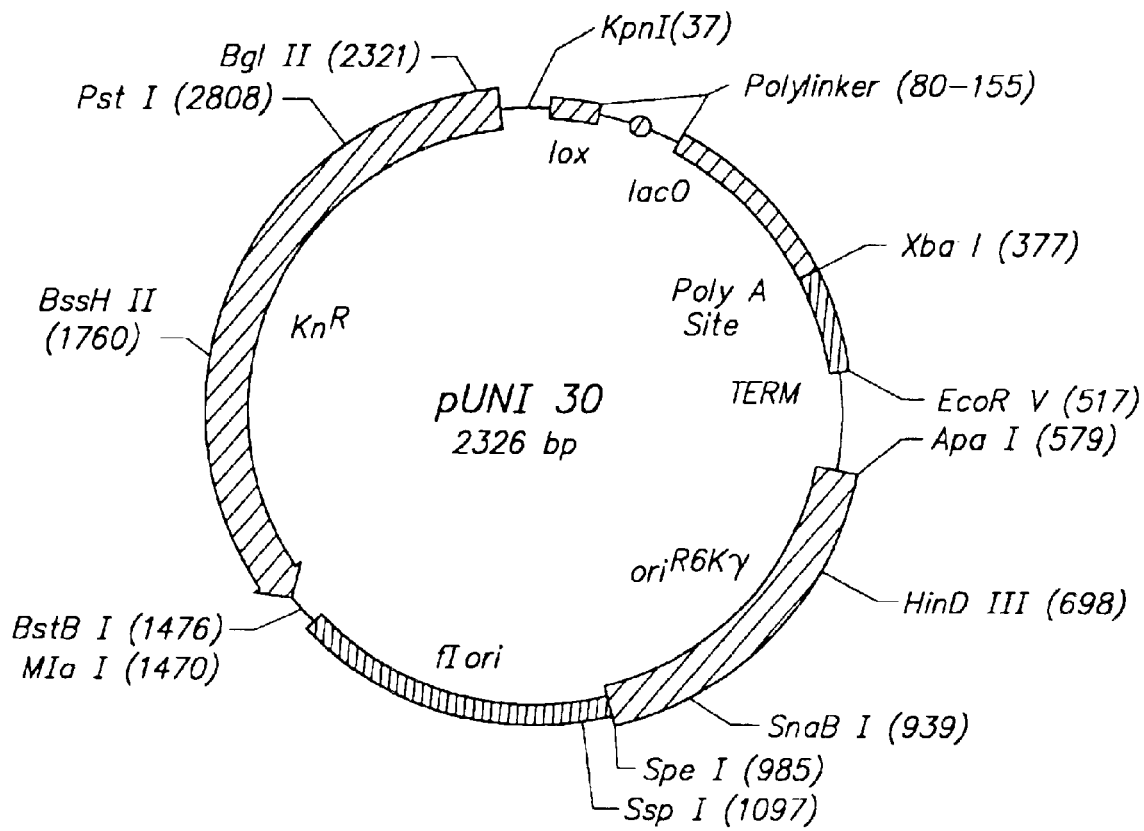

In this example, illustrative Univector constructs are provided. The map for several Univectors is shown in FIG. 23, showing pUNI-10, pUNI-20, and pUNI-30. In this figure, nucleotide positions (in parentheses) of unique restriction enzyme cleavage sites are shown. Functional sequences are shown as filled boxes and are labeled inside of the circle. Boxes with arrows are genes transcribed in the direction of the arrow. Below each map is the sequence of the polylinker region displayed as coding triplets in frame with the open reading frame of loxP. Unique restriction enzyme cleavage sites are in bold. General features of these Univectors include a loxP site placed adjacent to the 5' end of a polylinker for insertion of cDNAs. loxP has a single open reading frame that is in frame with the ATG of the NdeI and NcoI sites of the polylinker. This facilitates the subsequent generation of protein fusions as noted below. Following the polylinker are bacterial and eukaryotic transcriptional terminators to facilitate 3' end formation of transcripts. The Univectors also comprise a conditional origin or replication derived from R6Kγ that allows their propagation only in bacterial hosts expressing the pir gene originally from R6Kγ [Metcalf et al. (1994) Gene 138:1]. The Univectors also have the neo gene from Tn5 for selection in bacteria (e.g., selection of recombinant products of UPS is achieved by selecting for kanamycin resistance after transformation into a pir strain because the neo gene on the pUNI can only be propagated when covalently linked to an origin or replication that is functional in a pir, background). pUNI-20 contains additional site specific recombination sites, such as RS, that facilitate precise ORF transfer (POT), as described below.

One Univector construct, the pUNI-10 vector, contains a loxP site, a kanamycin resistance gene ($Kn^R$) and the R6Kγ conditional origin of replication ($OriR_{R6K\gamma}$). The $OriR_{R6K\gamma}$ is functional only in E. coli strains expressing the Π replication protein (i.e., the product of the pir gene). A gene of interest is placed within pUNI-10 (either as a result of constructing a library in pUNI-10 or by subcloning a previously cloned gene of interest). Once the gene of interest is contained within pUNI-10, any number of plasmid expression constructs containing this gene of interest can be constructed rapidly (e.g., within a single day). The expression constructs will contain an antibiotic resistance gene other than kanamycin (e.g., ampicillin). Using the site-specific recombinase, Cre, a precise fusion between the pUNI vector and any other loxP site-containing vector comprising the desired expression signals adjacent to the loxP site is catalyzed. The site-specific recombination event which occurs between the single loxP sites located on each plasmid (e.g., pUNI and the expression vector) results in the stable fusion of these two plasmids in such a manner as to place the expression of the gene of interest under the control of the expression signals contained within the expression vector. This subcloning event occurs without the need to use restriction enzymes. The fusion of pUNI-10 and the expression vector is selected for by selecting for the ability of E. coli cells that do not express the Π protein to grow in the presence of kanamycin. pUNI cannot replicate in E. coli cells that do not express the Π protein unless pUNI has fused or integrated into another plasmid that contains a normal (i.e., not a conditional) origin of replication (e.g., the Col E1 origin). In this case, pUNI will be replicated (as part of the fusion plasmid) and kanamycin resistance will be conferred on the host cell.

a) Generation of pUNI-10

Figures 2A, 2B:
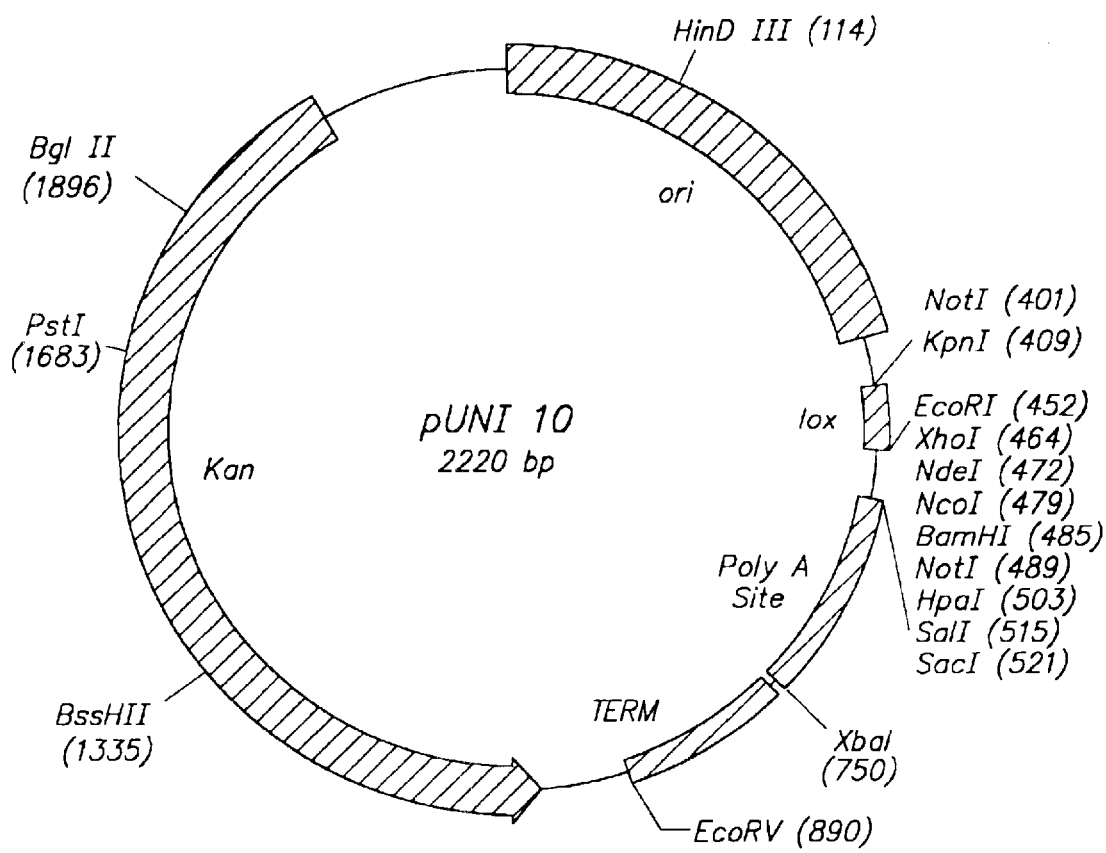
FIG. 2A provides a schematic map of the pUNI-10 vector; the locations of selected restriction enzyme sites are indicated and unique sites are indicated by the use of bold type.
FIG. 2B shows the DNA sequence of the loxP site and the polylinkers contained within pUNI-10 (i.e., nucleotides 401–530 of SEQ ID NO:1).

FIG. 2A provides a schematic map of the pUNI-10 vector; the locations of selected restriction enzyme sites are indicated (with the exception of NotI, all sites shown are unique). FIG. 2B shows the DNA sequence of the loxP site and the polylinkers contained within pUNI-10 (i.e., nucleotides 401–530 of SEQ ID NO:1).

Nucleotides 1–400 of pUNI-10 contain the conditional origin of replication from R6Kγ ($OriR_{R6K\gamma}$); the $OriR_{R6K\gamma}$ was derived from the plasmid R6K (ATCC 37120) [Metcalf et al. (1996) Plasmid 35:1]; nucleotides 401–414 comprise a NotI-KpnI polylinker that facilitates the exchange of lox sites; pUNI-10 contains a wild-type loxP site (as discussed above, pUNI vectors containing modified lox sites may be employed). Nucleotides 415–448 comprise the wild-type loxP site; nucleotides 449–527 comprise a polylinker used for the insertion of the gene of interest (genomic or cDNA sequences). Nucleotides 528–750 contain the polyA addition sequence from bovine growth hormone (BGH) (the BGH polyA sequence is available on a number of commercially available vectors including pcDNA3.1 (Invitrogen)); the BGH polyA sequence provides a 3' end for transcripts expressed in mammalian and other eukaryotic cells. The art is aware of other eukaryotic polyA sequences that may be used in place of the BGH polyA sequence (e.g., the SV40 poly A sequence, the TK polyA sequence, etc.). Nucleotides 751–890 contain the T7 terminator sequence which is used to terminate transcription in prokaryotic hosts (numerous prokaryotic termination signals are known to the art and may be employed in place of the T7 terminator sequence). Nucleotides 890–895 comprise an EcoRV restriction enzyme recognition site and nucleotides 896–2220 comprise the kanamycin resistance gene (Kan or $Kn^R$) from Tn5 which provides a positive selectable marker. The $Kn^R$ gene found on pUNI-10 was modified using site-directed mutagenesis to remove the naturally occurring NcoI site such that pUNI-10 contains a unique NcoI site in the polylinker region located at nucleotides 449–527. pUNI vectors need not contain a $Kn^R$ gene (modified or wild-type); other selectable genes may be used in place of the $Kn^R$ gene (e.g., ampicillin resistance gene, tetracycline resistance gene, zeocin™ resistance gene, etc.). The pUNI vector need not contain a selectable marker, although the use of a selectable marker is preferred. When a selectable marker is present on the pUNI vector, this marker is preferably a different selectable marker than that present on the pHOST vector. The nucleotide sequence of pUNI-10 is provided in SEQ ID NO:1.

EXAMPLE 2

Construction of Host Plasmids for Use in the Univector Plasmid-Fusion System Host plasmids used in the Univector plasmid fusion system are referred to as pHOST plasmids. pHOST plasmids or vectors are generally expression vectors that have been modified by the insertion of a site-specific recombination site, such as a lox site. The presence of the lox site on the pHOST plasmid permits the rapid subcloning or insertion of the gene interest contained within a pUNI vector to generate an expression vector capable of expressing the gene of interest. The pHOST vector may encode a protein domain such as an affinity domain including, but not limited to, glutathione-S-transferase (Gst), maltose binding protein (MBP), a portion of staphylococcal protein A (SPA), a polyhistidine tract, etc. A variety of commercially available expression vectors encoding such affinity domains are known to the art. When the pHOST plasmid contains a vector-encoded affinity domain, a fusion protein comprising the vector-encoded affinity domain and the protein of interest is generated when the pUNI and pHOST vectors are recombined.

In some embodiments of the present invention, the host vector features include the Col E1 origin of replication and the bla gene for propagation and selection in bacteria, a loxP site for plasmid fusions and a specific promoter residing upstream of, and adjacent to, the loxP site. Host vectors may also comprise sequences responsible for propagation, selection, and maintenance in organisms other than E. coli.

To generate expression vectors intended to generate transcriptional fusions (i.e., pHOST does not contain a vector-encoded protein domain), a lox site is placed after (i.e., downstream of) the start of transcription in the host vector. This is easily accomplished using synthetic oligonucleotides comprising the desired lox site. In designing the oligonucleotide comprising the lox site, care is taken to avoid introducing an ATG or start codon that might initiate translation inappropriately.

To generate expression vectors intended to generate a fusion protein between a vector-encoded protein domain and the protein of interest (encoded by the gene of interest contained within the pUNI vector), care is taken to place the lox site in the correct reading frame such that 1) an open reading frame is maintained through the lox site on pHOST and 2) the open reading frame in the lox site on pHOST is in frame with the open reading frame found on the lox site contained within the pUNI vector. In addition, the oligonucleotide comprising the lox site on pHOST is designed to avoid the introduction of in-frame stop codons. The gene of interest contained within the pUNI vector is cloned in a particular reading frame so as to facilitate the creation of the desired fusion protein.

The modification of several expression vectors is provided below to illustrate the creation of suitable pHOST vectors. In each case, the general strategy involved the generation of a linker containing a lox site by annealing two complementary oligonucleotides. The annealed oligonucleotides form a linker having sticky ends that are compatible with ends generated by restriction enzymes whose sites are conveniently located in the parental expression vector (e.g., within the polylinker of the parental expression vector).

a) Modification of the pGEX-2TKcs Prokaryotic Expression Vector pGEX-2TKcs is an expression vector active in E. coli cells which is designed for inducible, intracellular expression of genes or gene fragments as fusions with Gst. pGEX-2TKcs contains the IPTG-inducible tac promoter ($P_{tac}$) and was derived from pGEX-2TK (Pharmacia Biotech) as follows. The polylinker sequence of pGEX-2TK, 5'-GGATCCCCGGGAATTC-3' (SEQ ID NO:2), was replaced with the following sequence: 5'-GGATCGCATATGCCCATGGCTCGAGGATCCGA ATTC-3' (SEQ ID NO:3) to generate the pGEX-2TKcs vector.

Figure 3:
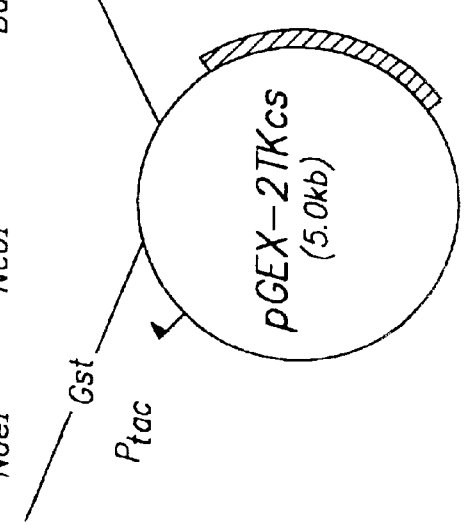
FIG. 3A shows the oligonucleotides (SEQ ID NOS:4 and 5) which were annealed to insert a loxP site into the polylinker of pGEX-2TKcs to create pGst-lox.
FIG. 3B provides a schematic map of pGEX-2TKcs which includes an enlargement of the multiple cloning site (MCS).
Figure 4:
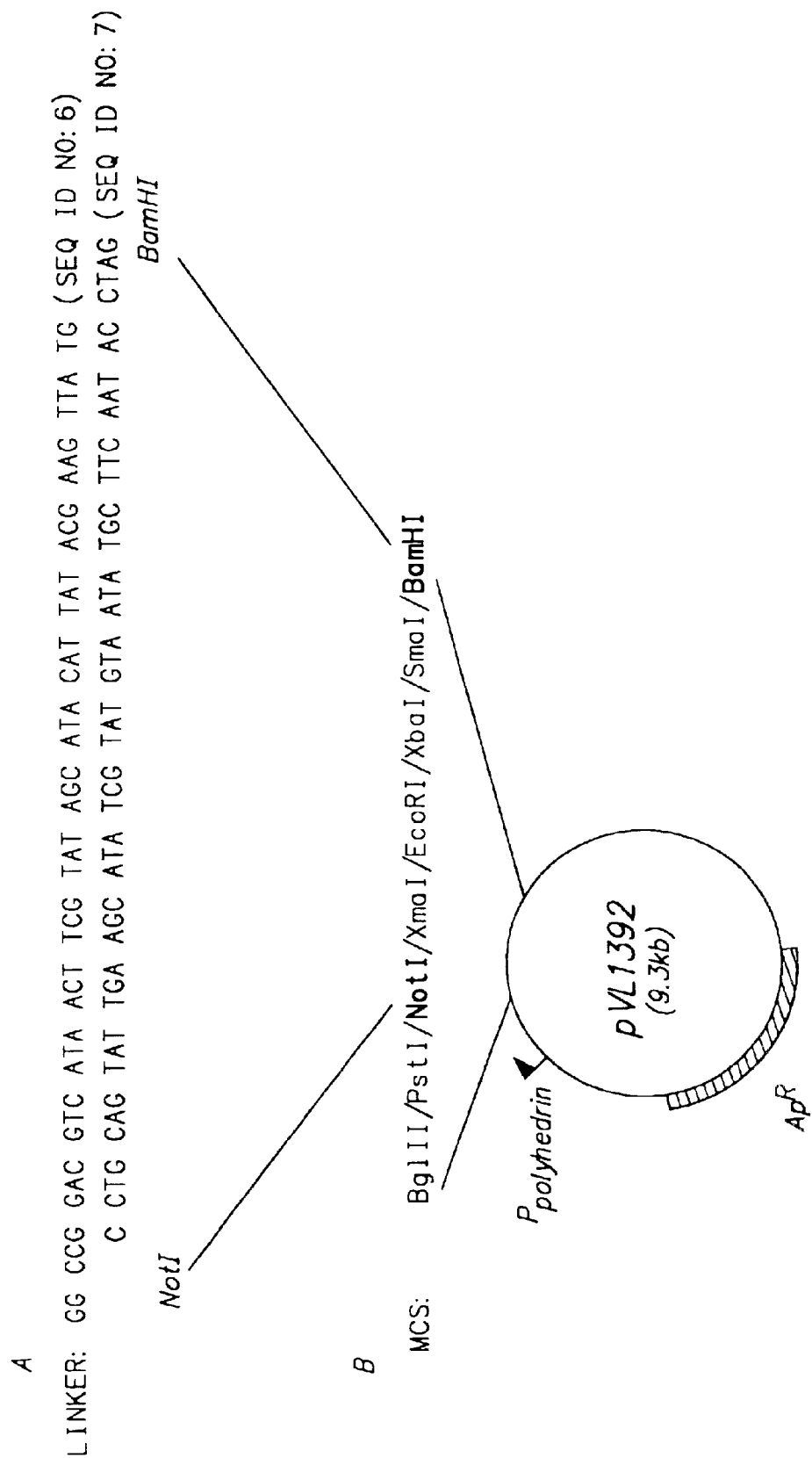
FIG. 4A shows the oligonucleotides (SEQ ID NOS:6 and 7) which were annealed to insert a loxP site into the polylinker of pVL1392 to create pVL1392-lox.
FIG. 4B provides a schematic map of pVL1392 which includes an enlargement of the multiple cloning site (MCS); the ampicillin resistance gene ($Ap^R$) and the tac promoter ($P_{tac}$) are indicated.
Figure 5:
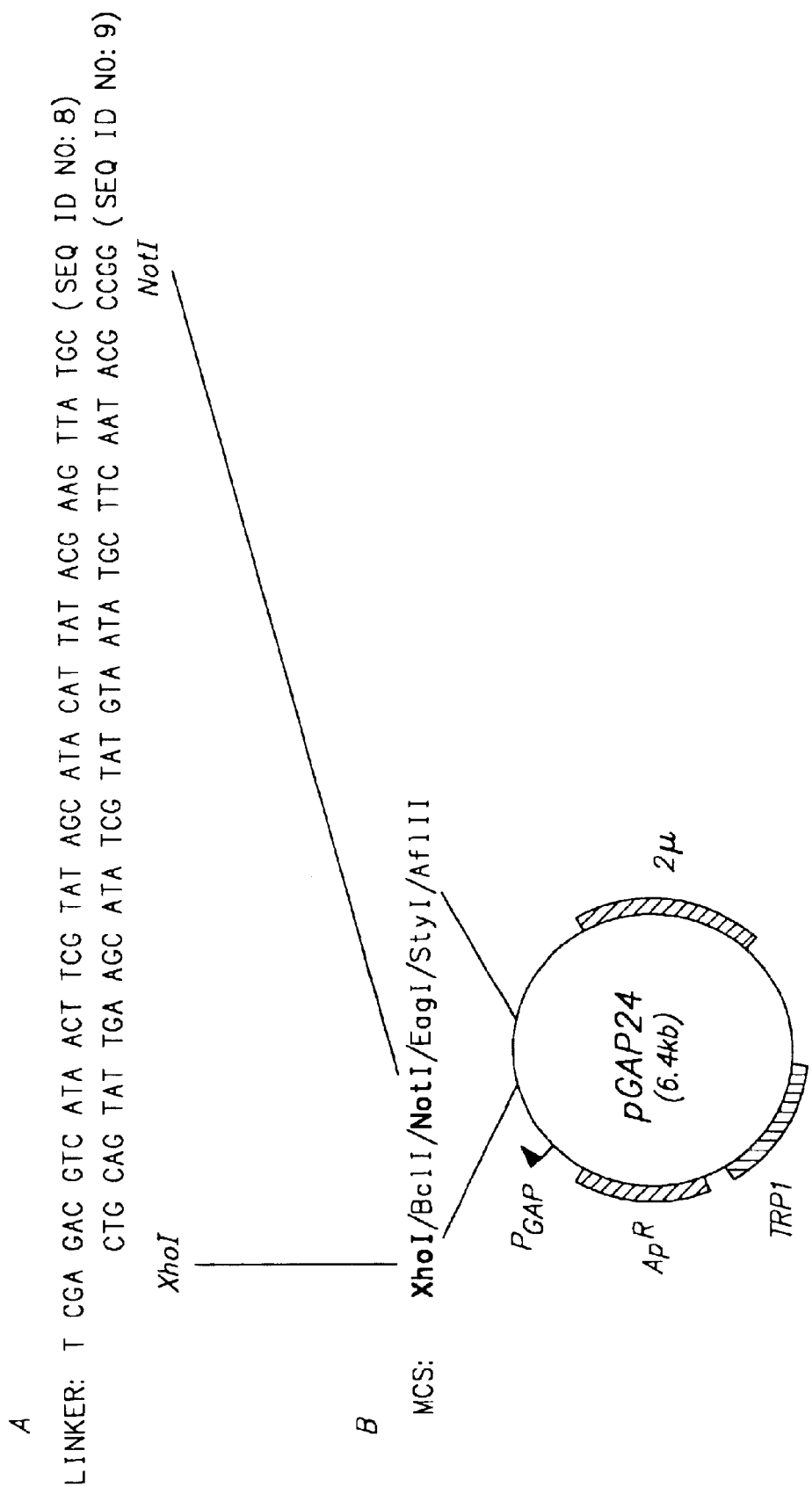
FIG. 5A shows the oligonucleotides (SEQ ID NOS:8 and 9) which were annealed to insert a loxP site into the polylinker of pGAP24 to create pGAP24-lox.
FIG. 5B provides a schematic map of pGAP24 which includes an enlargement of the multiple cloning site (MCS); the ampicillin resistance gene ($Ap^R$), the GAP promoter ($P_{GAP}$), the origin from the 2 µm circle (2 µ) and the TRP1 gene, encoding N-(5'-phosphoribosyl)-anthranilate synthetase, (TRP1) are indicated.
Figure 6:
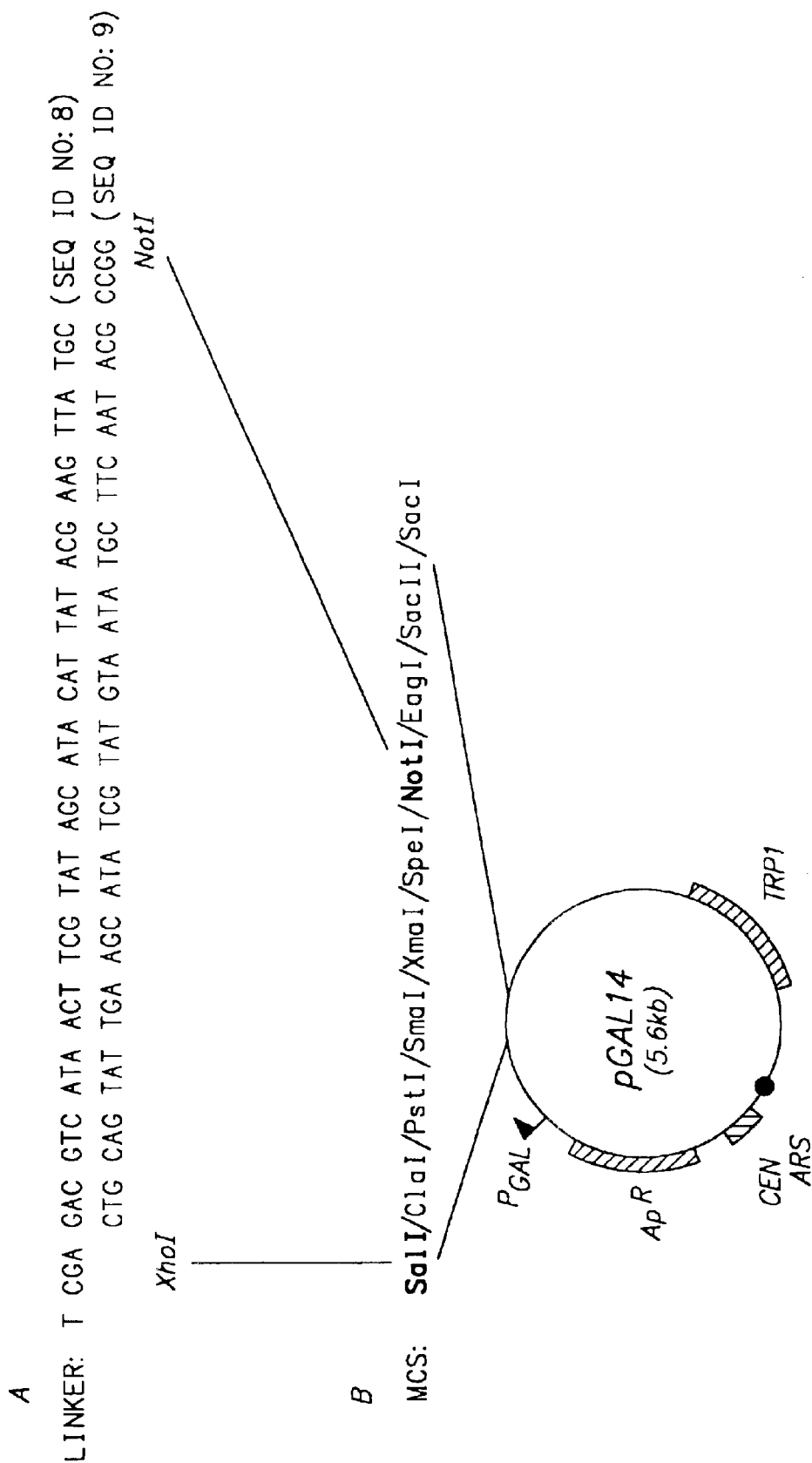
FIG. 6A shows the oligonucleotides (SEQ ID NOS:8 and 9) which were annealed to insert a loxP site into the polylinker of pGAL14 to create pGAL14-lox.
FIG. 6B provides a schematic map of pGAL14 which includes an enlargement of the multiple cloning site (MCS); the ampicillin resistance gene ($Ap^R$), the GAL promoter ($P_{GAL}$), the yeast centromeric sequences (CEN), yeast autonomous replication sequences (ARS) and the TRP1 gene (TRP1) are indicated.

A linker containing a loxP site was generated by annealing the following oligonucleotides: 5'-CATGGCTATAACTTCGTATAGCATACATTATACGAA GTTATG-3' (SEQ ID NO:4) and 5'-GATCCATAACTTCGTATAATGTATGC TATACGAAGTTATAGC-3' (SEQ ID NO:5). When annealed, these two oligonucleotides form a double-stranded linker having a 5' end compatible with an NcoI sticky end and a 3' end compatible with a BamHI sticky end (FIG. 3A). pGEX-2TKcs was digested with NcoI and BamHI (FIG. 3B) and the annealed loxP linker was inserted to form pGst-lox.

b) Modification of the pVL1392 Baculovirus Expression Vector pVL 1392 is an expression vector that contains the polyhedrin promoter which is active in insect cells (Pharmingen). A linker containing a loxP site was generated by annealing the following oligonucleotides: 5'-GGCCGGACGTCATAACTTCGTAT AGCATACATTATACGAAGTTATG-3' (SEQ ID NO:6) and 5'-GATCCATAACTTC GTATAATGTATGCTATACGAAGTTATGACGTCC-3' (SEQ ID NO:7). When annealed, these two oligonucleotides form a double-stranded linker having a 5' end compatible with a NotI sticky end and a 3' end compatible with a BamHI sticky end (FIG. 4A). pVL1392 was digested with NotI and BamHI (FIG. 4B) and the annealed loxP linker was inserted to form pVL1392-lox.

c) Modification of the pGAP24 Yeast Expression Vector pGAP24 is an expression vector that is based on the yeast 2 μm circle and contains the constitutive GAP (glyceraldehyde 3-phosphate dehydrogenase) promoter ($P_{GAP}$) which is active in yeast cells and the TRP1 gene (used a selectable marker when the cells are grown in medium lacking tryptophan) [the GAP promoter is available on pAB23; Schilds (1990) Proc. Natl. Acad. Sci. USA 87:2916]. A linker containing a loxP site was generated by annealing the following oligonucleotides: 5'-TCGAGAC GTCATAACTTCGTATAGCATACATTATACGAAGTTAT GC-3' (SEQ ID NO: 8) and 5'-GGCCGCATAACTTC GTATAATGTATGCTATACGAAGTTATGACGTC-3' (SEQ ID NO:9). When annealed, these two oligonucleotides form a double-stranded linker having a 5' end compatible with a XhoI sticky end and a 3' end compatible with a NotI sticky end (FIG. 5A). pGAP24 was digested with XhoI and NotI (FIG. 5B) and the annealed loxP linker was inserted to form pGAP24-lox.

d) Modification of the pGAL14 Yeast Expression Vector pGAL14 is a yeast centromeric expression vector that contains the GAL promoter ($P_{GAL}$), which is induced by the presence of galactose in the medium, and the TRP1 gene. A linker containing a loxP site was generated by annealing together the oligonucleotides listed in SEQ ID NOS:8 and 9. When annealed, these two oligonucleotides form a double-stranded linker having a 5' end compatible with a XhoI sticky end and a 3' end compatible with a NotI sticky end (FIG. 6A). pGAL14 was digested with XhoI and NotI (FIG. 6B) and the annealed loxP linker was inserted to form pGAL14-lox.

EXAMPLE 3

Expression and Purification of a Gst-Cre Fusion Protein

In order to provide a source of purified Cre recombinase for the in vitro recombination of plasmids, the cre gene was inserted into a Gst expression vector such that a fusion protein comprising Gst at the amino-terminal end and Cre recombinase at the carboxy-terminal end was produced. The Gst-Cre fusion protein was purified by chromatography using Glutathione Sepharose 4B (Pharmacia). Purified Gst-Cre can be stored at −80° C., −20° C., or 4° C. for several months without significant loss of activity.

To simplify Cre purification, a plasmid expressing a GST-cre fusion protein was constructed, pQL123. The cre gene was isolated by polymerase chain reaction (PCR) amplification using the plasmid pBS39 (U.S. Pat. No. 4,959,317). U.S. Pat. Nos. 4,683,195, 4,683,202 and 4,965,188 describe PCR methodology and are incorporated herein by reference. The primers used in the PCR were designed to introduce an NcoI site at the first ATG in the cre open reading frame. The PCR product was cloned into a TA cloning vector (pCRII.1; Invitrogen) and then was subcloned as an NcoI-EcoRI fragment into pGEX-2TKcs (Example 2) to generate pQL123. The ligation products were used to transform DH5α cells and the desired recombinant was isolated and used to transform BL21(DE3) cells (Invitrogen).

The nucleotide sequence of the Gst-Cre coding region within pQL123 is listed in SEQ ID NO:10 (FIG. 26B). The amino acid sequence of the fusion protein expressed by pQL123 is listed in SEQ ID NO:11 (FIG. 26C).

To express the Gst-Cre fusion protein, BL21(DE3) cells containing the pQL123 plasmid were grown at 37° C. in LB containing 100 μg/ml ampicillin until the $OD_{600}$ reached 0.6. Expression of the fusion protein was then induced by the addition of IPTG to a final concentration of 0.4 mM and the cells were allowed to grow overnight at 25° C. Following induction, the bacterial cells were pelleted by centrifugation at 5,000 ×g at 4° C. and the supernatant was discarded. A cell lysate was prepared as follows. Cells harvested from 0.5 liter of culture were suspended in 35 ml of a solution containing 20 mM Tris-HCl, pH 8.0, 0.1 M NaCl, 1 mM EDTA, 0.5% Nonidet P-40, 5 μg/ml of each of leupeptin, antipain, aprotinin and 1 mM PMSF at 4° C. The cells were incubated for 10 min on ice and then disrupted by sonication (3×15 sec bursts) using a sonicator (Ultrasonic Heat Systems Model 200R) at full power. The lysate was then clarified by centrifugation at 12,000 rpm using a SS34 rotor (Sorvall).

The Gst-Cre fusion protein was affinity purified from the cell lysate by chromatography on Glutathione Sepharose 4B (Pharmacia) according to the manufacturer's instructions. The protein concentration of Gst-Cre was determined by Bradford analysis (BioRad).

Figure 7:
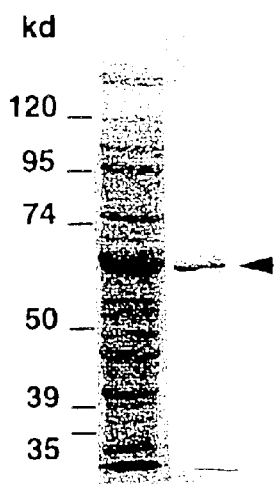
FIG. 7 shows a Coomassie blue-stained SDS-PAGE gel showing the purification of Gst-Cre from *E. coli* cells containing pQL123.

Aliquots of the cell lysate before and after chromatography on Glutathione Sepharose 4B were applied to an SDS-PAGE gel. Following electrophoresis, the gel was stained with Coomassie blue. The stained gel is shown in FIG. 7. In FIG. 7, lanes 1 and 2 contain the cell lysate before and after chromatography, respectively. The arrowhead indicates the Gst-Cre fusion protein. The migration of the molecular weight protein markers is indicated to the left of lane 1. The results shown in FIG. 7 demonstrate the purification of the Gst-Cre fusion protein. This fusion protein was shown to be functional (i.e., capable of mediating recombination between lox sites) in the in vitro recombination assay described below.

Figure 24:
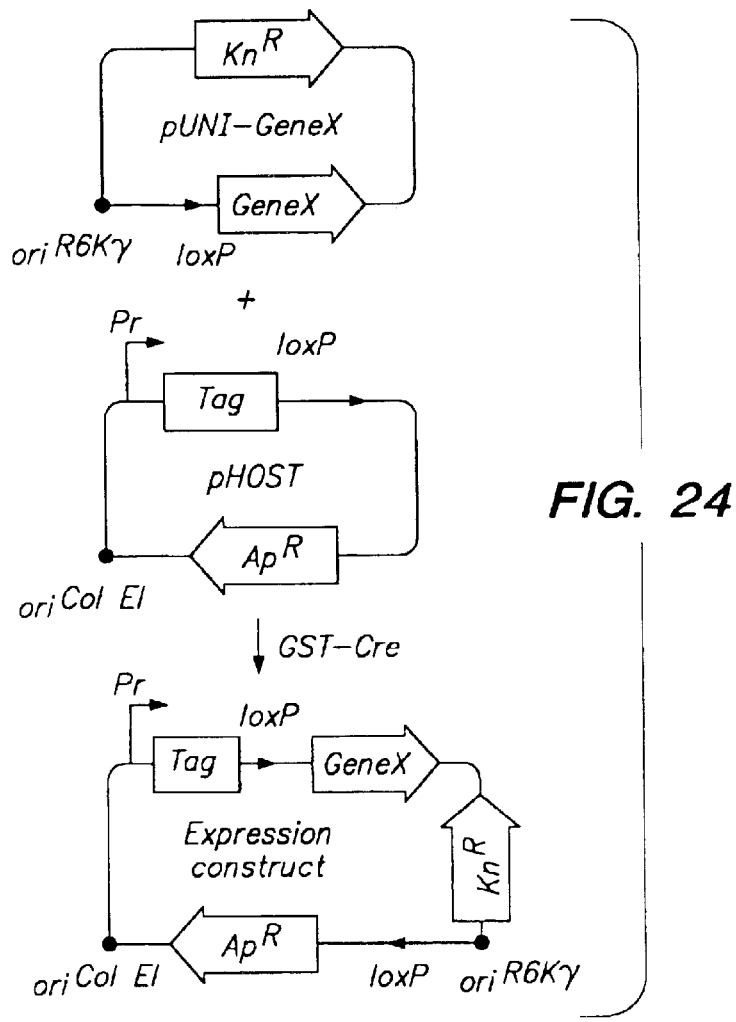
FIG. 24 shows a schematic of a method for producing a tagged recombinant protein.

Gst-Cre retained high recombinase activity as measured by UPS. The efficiency of this reaction reached up to 16.8% as shown in FIG. 15, similar to that for native Cre (Abremski et al., supra). In this figure, the indicated amounts of Gst-Cre were incubated with pUNI-10 and pQL103 plasmid DNA as described below. Percentage of recombinants were calculated by measuring the ratio of total kanamycin resistant transformants (fusion events between pUNI-10 and pQL103) relative to total ampicillin resistant transformants (pQL103 alone and pUNI-10-pQL103 fusions). The efficiency of Gst-Cre was examined in a second reaction producing a tagged recombinant protein as diagrammed in FIG. 24, fusing a Gst tag to Skp1. Recombinant plasmids isolated from $Kn^r$ transformants were shown by restriction analysis to be correct fusion products between the Univector and the host vector via the loxP sites. In this case, 10 of 12 $Kn^r$ transformants were the correct heterodimer (FIG. 9) and 2 were trimers (FIG. 9, lanes 8 and 10) with two copies of pUNI fused to a host vector. It should be noted that trimeric plasmids also have a correct fusion junction that places the gene of interest adjacent to the desired regulatory sequences and are fully functional for most needs. However, the isolation of trimeric plasmids can be nearly eliminated if gel purified monomeric supercoiled host DNA is used. This method is highly efficient and typically requires only one or two minipreps to identify the desired construct.

EXAMPLE 4

In Vitro Recombination Using the Univector Plasmid Fusion System

Figure 8:
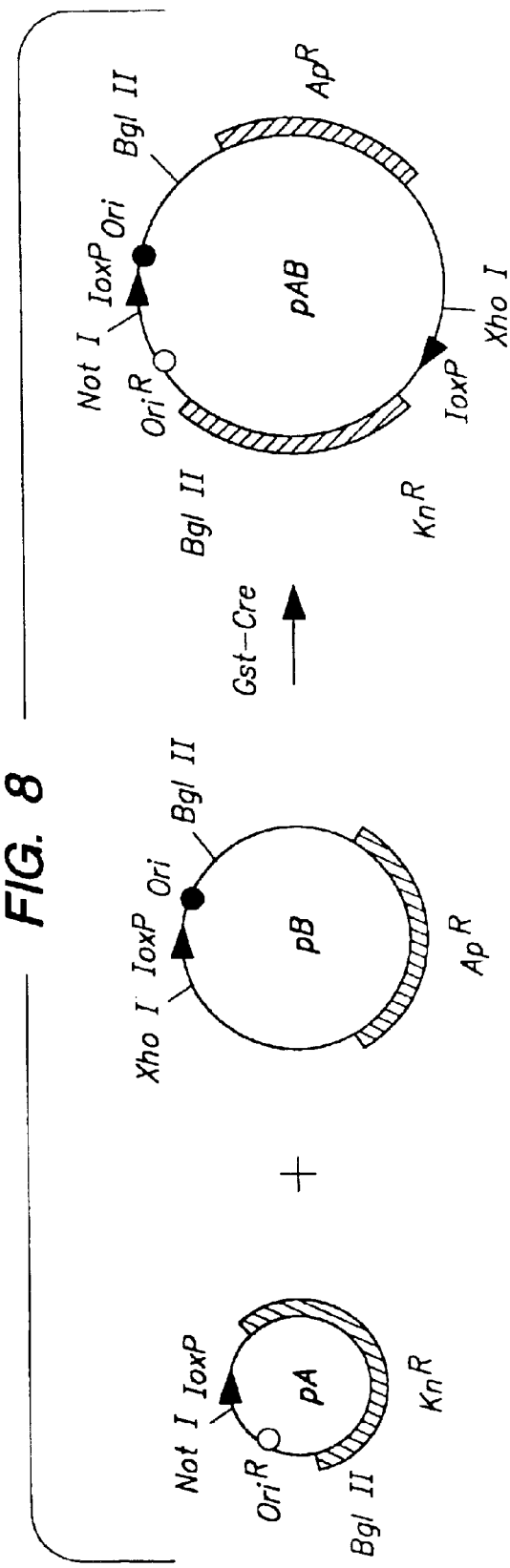
FIG. 8 provides a schematic showing the strategy employed for the in vitro recombination of a pUNI vector ("pA," pUNI-5) with a pHOST vector ("pB," pQL103) to create a fused construct ("pAB"). The relevant markers on each construct are indicated, as are selected restriction enzyme sites.

The Univector Plasmid Fusion System permits the in vitro recombination of two plasmids. FIG. 8 provides a schematic showing the strategy employed for in vitro recombination. pA represents a generic pUNI vector that contains a loxP site, a kanamycin resistance gene and the conditional R6K origin that is only functional in E. coli strains expressing the II protein (e.g., E. coli strains BW18815, BW19094, BW20978, BW20979, BW21037, BW21038). pB represents a generic pHOST vector that contains a loxP site, an ampicillin resistance gene and a Col E1 origin of replication. pAB represents the fused plasmid which results from the Cre-mediated fusion of pA and pB.

To illustrate the in vitro recombination reaction, pUNI-5 (a pUNI vector which differs from pUNI-10 only in that pUNI-5 retains the NcoI site in the $Kn^R$ gene and contains a different polylinker) was employed as pA and pQL103, an ampicillin-resistant plasmid containing a loxP site and the ColE1 origin, was employed as pB. In a total reaction volume of 20 μl, 0.2 μg of each pUNI-5 (pA) and pQL103 (pB) were mixed in a buffer containing 50 mM Tris-HCl (pH 7.5), 10 mM $MgCl_2$, 30 mM NaCl and 1 mg/ml BSA. The amount of purified Gst-Cre (Example 3) was varied from 0 to 1.0 μg. The reactions were incubated at 37° C. for 20 minutes and then the reactions were placed at 70° C. for 5 min. to inactivate the Gst-Cre protein. Five microliters of each reaction mixture were used directly to transform competent DH5α cells ($CaCl_2$ treated). The transformed cells were plated onto LB/Amp (100 μg/ml amp) and LB/Kan (40 μg/ml kan) plates and the number of ampicillin resistant ($Ap^R$) and kanamycin-resistant ($Kn^R$) colonies were counted. The results are summarized in Table 1.

TABLE 1

| Gst-Cre (μg/reaction) | AP$^R$ Colonies | Kn$^R$ Colonies | % of Total Kn$^R$/Ap$^R$ |
| --- | --- | --- | --- |
| 0 | 2.6 × 10$^4$ | 0 | 0 |
| 0.01 | 1.9 × 10$^4$ | 571 | 3 |
| 0.05 | 1.1 × 10$^4$ | 682 | 6.2 |
| 0.1 | 1.5 × 10$^4$ | 502 | 3.3 |
| 0.5 | 0.3 × 10$^4$ | 104 | 3.4 |
| 1.0 | 0.3 × 10$^4$ | 52 | 1.7 |

The results shown in Table 1 demonstrate, that under these reaction conditions 0.05 μg purified Gst-Cre per 20 μl reaction yields the most efficient rate of plasmid fusion. Plasmid DNA was isolated from individual kanamycin-resistant colonies (using standard mini-prep plasmid DNA isolation protocols) and subjected to restriction enzyme digestion to determine the structure of the fused plasmids. This analysis revealed that plasmid DNA isolated from the kanarnycin-resistant colonies represented a dimer created by the desired fusion of pUNI-5 and pQL103 via the loxP sites. These results demonstrate that the Univector Plasmid Fusion System can be used to rapidly fuse two plasmids together in vitro.

EXAMPLE 5

In Vitro Fusion Between a pUNI Vectors Containing Genes of Interest and Lox-Containing Expression Vectors Produces Fused Vectors Capable of Expressing the Gene of Interest In Example 4 it was demonstrated that the Univector Plasmid Fusion System can be used to rapidly fuse two plasmid constructs together in vitro. In this example, the ability of the Univector Plasmid Fusion System to fuse two plasmids together in a manner that places the gene of interest contained on the pUNI vector under the transcriptional control of a promoter contained on the pHOST or expression vector in such a manner that a functional protein of interest is expressed from the fused construct. A series of expression plasmids were made by UPS and tested for expression in several contexts.

a) Insertion of a Gene of Interest into the pUNI-10 Vector

The cDNA encoding the wild-type yeast Skp1 protein [Bai et al. (1996) Cell 86:263] was cloned into the pUNI-10 vector between the NdeI and BamHI sites to generate pUNI-Skp1; the yeast SKP1 cDNA sequence is available as GenBank Accession No. U61764. Skp1 is an essential protein involved in the regulation of the cell cycle in yeast. Yeast cells containing a temperature sensitive mutant of Skp1 cannot grow at the non-permissive temperature (37° C.).

b) In Vitro Fusion Reactions and Complementation Assays pUNI-Skp1 was recombined with pGAP24-lox (Example 2) and pGAL14-lox (Example 2) using the in vitro reaction described in Example 4; 0.2 μg of Gst-Cre was used per 20 μl reaction. The resulting plasmid fusions were termed pGAP24-Skp1 and pGAL14-Skp1. pGAP24-Skp1 and pGAL14-Skp1 were then transformed into the temperature sensitive (ts) skp1-11 mutant yeast strain Y555 (Bai et al., supra) and the transformed yeast cells were plated onto SC-tryptophan plates (to select for the expression of the selectable marker TRP1) and incubated at either a permissive (25° C.) or non-permissive temperature (37° C.). The plates which received yeast cells transformed with pGAL14-Skp1 contained galactose. The ability of the transformed cells to grow at the non-permissive temperature is dependent upon the expression of the wild-type skp1 gene encoded by a properly fused pUNI-Skp1/expression vector construct. As a control, the yeast SKP1 genomic clone contained in a URA3 CEN vector (produced by conventional cloning techniques) was used to transform the ts skp1-11 mutant yeast strain Y555 and the transformed cells were also plated at 25° C. and 37° C. In each case, an expression vector (e.g., pRS414 or pRS415; Bai et al., supra) lacking the SKP1 gene but containing the same selectable marker (i.e., TRP1) as either pGAP24-Skp1, pGAL14-Skp1 or URA3 CEN-Skp1 was used to transform Y555 cells as a control capable of permitting the growth of transformed Y555 cells on selective medium at the permissive temperature.

Figure 9B:
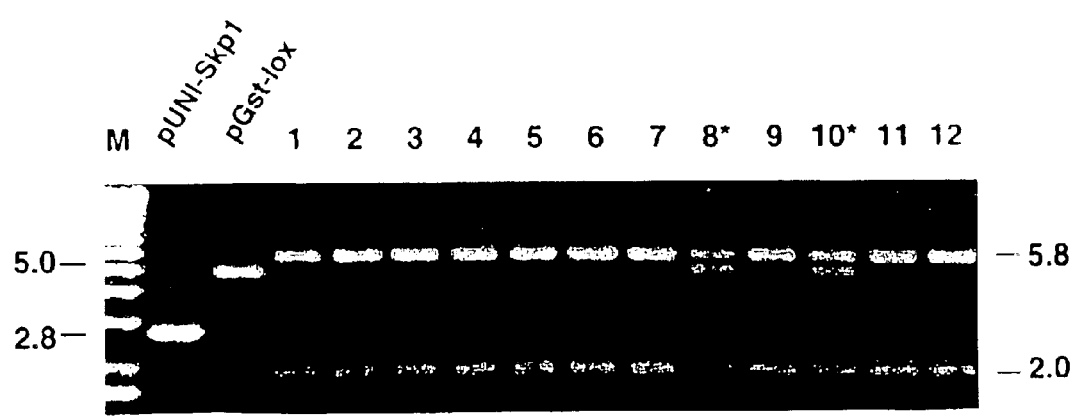
FIG. 9B provides an ethidium bromide-stained gel showing the separation of restriction fragments generated by the digestion of pUNI-Skp1, pGst-lox and pGst-Skp1.
Figure 9A:
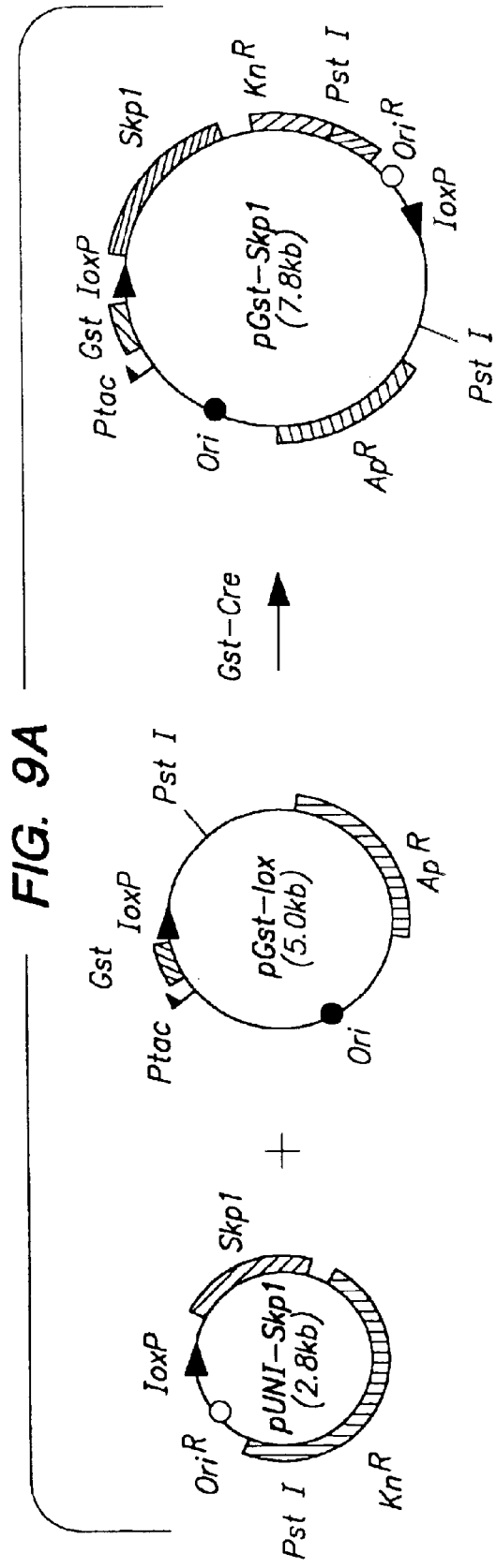
FIG. 9A provides a schematic showing the starting constructs (pUNI-Skp1 and pGst-lox) and the predicted fusion construct (pGst-Skp1) generated by an in vitro fusion reaction.

The results demonstrated that the URA3 CEN-SKP1 construct produced by conventional cloning techniques produced a functional Skp1 protein which was capable of complementing the lethality of the skp1-11 ts mutation. More importantly, the results demonstrated that the in vitro fusion reaction that created pGAP24-Skp1 and pGAL14Skp1 produced constructs capable of producing functional Skp1; that is, Y555 cells transformed with either pGAP24-Skp1 or pGAL14-Skp1 were capable of growth at 3 7° C., a temperature at which the ts Skp1-11 protein produced by the host strain is non-functional. Expression vectors lacking the SKP1 cDNA were incapable of complementing the lethality of the skp1-11 ts mutation.

c) Restriction Analysis, SDS-PAGE Analysis and Western Blot Analysis of in Vitro Fusion Reactions pUNI-Skp1 was recombined with pGst-lox (Example 2) using the in vitro reaction described in Example 4; 0.2 μg of Gst-Cre was used per 20 μl reaction. The resulting plasmid fusion was termed pGST-Skp1. FIG. 9A provides a schematic showing the starting constructs and the predicted fusion construct. Five microliters of the fusion reaction mixture was used transform DH5α cells as described in Example 4. The transformed cells were plated onto LB/Amp/Kan plates and plasmid DNA was isolated from individual Ap$^R$Kn$^R$ colonies. The plasmid DNAs were digested with PstI followed by electrophoresis on agarose gels to examine the structure of the fused plasmids. A representative ethidium bromide-stained gel is shown in FIG. 9B. In FIG. 9B, lane "M" contains DNA size markers, lanes pUNI-Skp1 and pGst-lox contain the starting plasmids digested with PstI and lanes 1–12 contain plasmid DNA from individual Ap$^R$Kn$^R$ colonies digested with PstI. Lanes marked with an "*" indicate that these colonies contained a trimeric fusion plasmid that resulted from the fusion of two Gst-lox plasmids and one pUNI-Skp1 plasmid. The sizes of the two PstI fragments which result from the fusion of pUNI-Skp1 and pGst-lox in kb are indicated (5.8 and 2.0 kb). The results shown in FIG. 9B demonstrate that the in vitro fusion reaction resulted in the production of the desired fused construct with high efficiency (about 83% of the plasmids in the Ap$^R$Kn$^R$ colonies comprised the fusion of one pUNI-Skp1 vector with one pGst-lox vector).

Three individual Ap$^R$Kn$^R$ colonies were picked and grown in liquid cultures which were induced with IPTG to examine whether the fused construct (pGst-Skp1) could produce the desired Gst-Skp1 fusion protein. The cultures were grown, induced and cell extracts were prepared as described in Example 6. An aliquot of the cell lysates prepared from induced and uninduced cells were electrophoresed on an SDS-PAGE gel and the gel was either stained with Coomaise blue or transferred to nitrocellulose to generate a Western blot. The Western blot was probed using an anti-Skp1 polyclonal antibody (the antibody was raised against the yeast Skp1 using conventional methods). The resulting Coomassie-stained gel and Western blot are shown in FIGS. 10A and 10B, respectively.

Figure 10A:
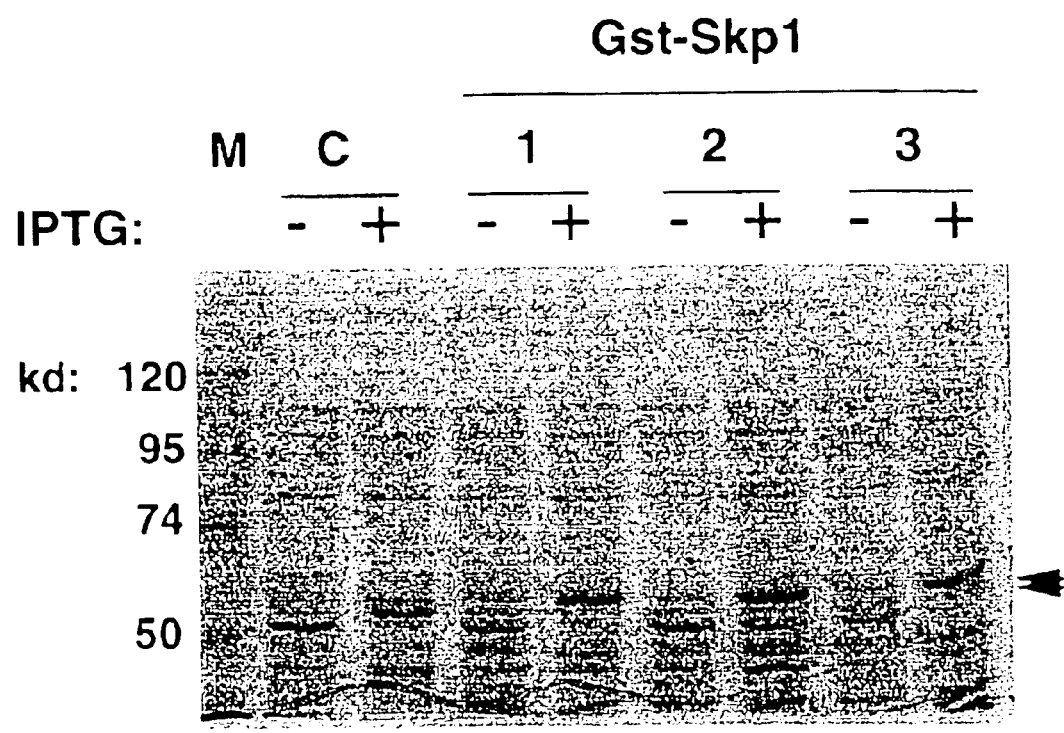
FIG. 10A shows a Coomassie blue-stained SDS-PAGE gel showing the expression of the Gst-Skp1 protein from *E. coli* cells containing pGst-Skp1.

In FIG. 10A, lane "M" contains protein molecular weight markers (size in kd is indicated). Lanes marked "C" contain extracts prepared from *E. coli* containing a GST-SKP1 construct made by conventional cloning (i.e., the SKP1 cDNA was excised using restriction enzymes and inserted into pGEX-2TKcs (Example 2)). Lanes 1–3 contain extracts from $Ap^R Kn^R$ cells transformed with in vitro fusion reaction mixtures. Extracts prepared from uninduced cells and IPTG induced cells are indicated by "−" and "+", respectively. The arrowheads indicate the location of the Gst-Skp1 fusion proteins. The Gst-Skp1 fusion product generated from the pGST-SKP1 fusion construct contains 15 additional amino acids which are located between the Gst domain and the Skp1 protein sequences relative to the Gst-Skp1 fusion protein expressed from the conventionally constructed GST-SKP1 plasmid (the additional 15 amino acids are encoded by the linker comprising the loxP site; see FIG. 3). In FIG. 10B, the lane designations are the same as described for FIG. 10A. This Western blot confirms that the bands indicated by the arrowheads in FIG. 10A represent Gst-Skp1 fusion proteins.

Figure 10B:
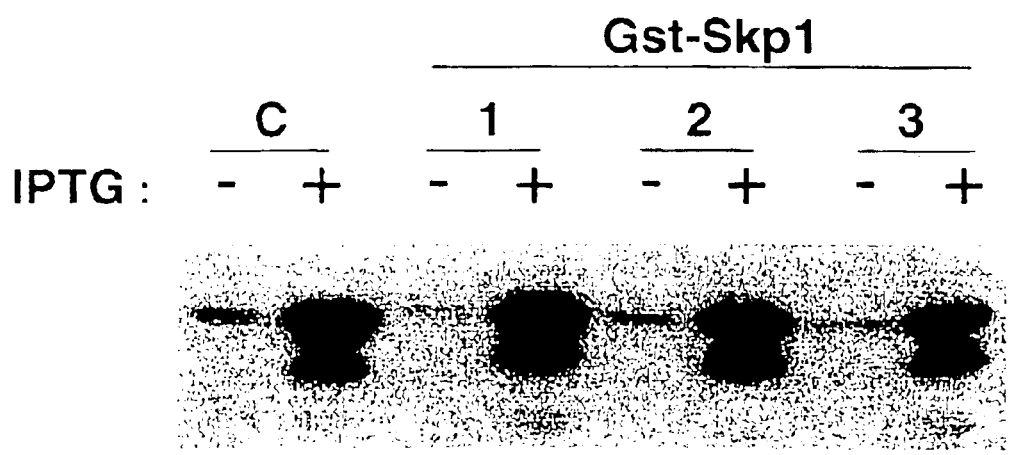
FIG. 10B shows a Western blot of an SDS-PAGE gel containing extracts prepared from *E. coli* cells containing pGst-Skp1 which was probed using an anti-Skp1 antibody.

The results shown in FIGS. 10A and 10B demonstrate that the Univector Fusion System can be used to create an expression vector that maintains the proper translational reading frame and permits the expression of a fusion protein comprising the expression vector-encoded affinity tag and the protein of interest.

The above results demonstrate that the Univector Fusion System can be used to recombine two plasmids, one containing a gene of interest but no promoter (this vector may optionally contain expression signals such as termination signals and/or polyadenylation signals) and the other containing a promoter and optionally other expression signals (e.g., splicing signals, translation initiation codons) (and optionally sequences encoding an affinity domain) but lacking a gene of interest, in vitro in such a manner that the proper translational reading frame is maintained permitting the expression of a functional protein from the fused plasmids in the host cell.

d) Additional Examples

Figure 16A:
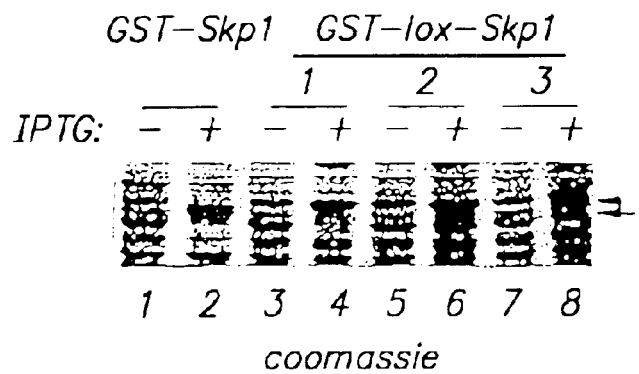
FIG. 16A and 16B shows the protein expression of UPS generated fusion proteins containing loxP following separation by SDS-PAGE and (A) staining with Coomassie blue, and (B) immunoblotting with anti-Skp1 antibodies.
Figure 16B:
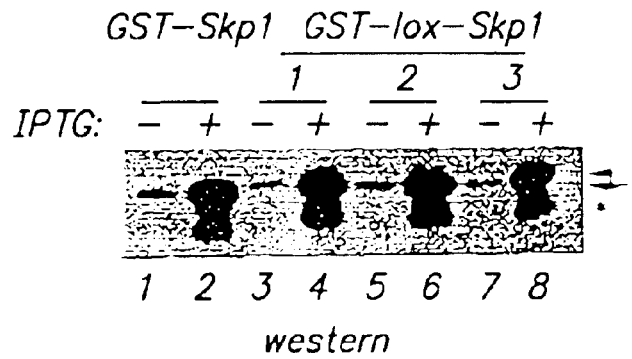

The *S. cerevisiae* SKP1 ORF (Bai et al., supra) in pUNI-10 was fused to the pGST-lox host vector pHB2-GST by UPS to create a bacterial Gst-lox-Skp1 fusion protein expressed under the control of the *E. coli* tac promoter. A similar Gst-Skp1 expression plasmid lacking loxP (i.e., pCB149) made by conventional cloning, was used as a control. Approximately equal amounts of the two fusion proteins were expressed as shown in FIG. 16A and B, indicating that the presence of loxP did not significantly affect either the transcription or translation of the fusion protein. In this figure, proteins were separated by SDS-PAGE and stained with Coomassie blue (FIG. 16A) or inimunoblotted (FIG. 16B) with anti-Skp1 antibodies. Protein from a control GST-Skp1 expression plasmid lacking loxP (lanes 1 and 2) and three independent transformants of UPS-derived Gst-lox-Skp1 expression constructs (lanes 3–8) are shown. The asterisk denotes a degradation product.

In another example, to measure the effect of the loxP sequence upon eukaryotic expression in the context of transcriptional fusions, the SKP1 ORF was placed under the control of the *S. cerevisiae* GAL1 promoter both by conventional means and by UPS. In this case, it was observed that the relative expression level of the UPS-derived plasmid was slightly lower. This reduction in expression might be explained by the ability of loxP RNA to form a 13 bp stem-loop, as secondary structures formed within the 5' UTR of an mRNA can interfere with the initiation of translation [Kozak (1989) *Mol. Cell. Biol.* 9:5134], although an understanding of the mechanism is not required to practice the present invention, and the present invention is not limited to any particular mechanistic explanation. To test this hypothesis, a series of lox sites were made containing mutations designed to reduce the stability of the stem-loop, as described in Example 8.

Figure 17:
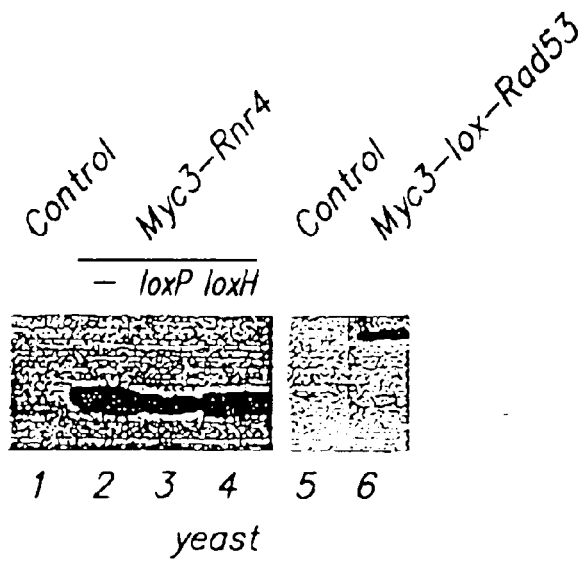
FIG. 17 shows a comparison of expression levels between loxP and loxH containing constructs.

In yet other examples, multiple genes have been tested using UPS and expressed in several different organisms. In addition to Gst-Skp1 expression in bacteria, Myc-Rnr4 and Myc-Rad53 have been expressed in *S. cervisiae* as shown in FIG. 17, showing a comparison of expression levels between loxP and loxH containing constructs. Protein extracts were prepared from Y80 cells grown in SC-ura plus galactose containing the following plasmids: vector alone (lane 1), pMH176 (GAL-MYC3-RNR4) made by conventional cloning lacking a lox sequence (lane 2), UPS-derived GAL-lox-MYC3-RNR4 constructs with either loxP (lane 3) or loxH (lane 4) present between the GAL1 promoter and the MYC3-RNR4 gene, vector alone (lane 5), and UPS-derived GAL1-MYC3-lox-RAD53 construct (lane 6). The recipient vector for RAD53 was pHY314-MYC3.

Furthermore, many baculovirus expression constructs have been made by UPS and tested. Shown in FIG. 18, as illustrative examples, are Gst-Rad53, Myc-Rad53, and HA-Rad53. For Rad53, the UPS-derived constructs express at the same level as Gst-Rad53 made by conventional methods (FIG. 18, compare lanes 1 and 2). FIG. 18 shows the expression of the UPS-derived baculovirus expression constructs in insect cells. UPS reactions were performed between pUNI-10-RAD53 clones and baculovirus expression vectors in pVL1392 backbones engineered to contain lox sites and epitope tags. Host insect expression vectors used were pHI100-GST, pHI 100-MYC3, and pHI100-HA3 and the resulting fusion plasmids were crossed onto Baculogold (Pharmingen) by standard methods. GST affinity purified protein from lysates from 1 million cells infected with baculovirus expressing either GST-RAD53 made by conventional cloning (lane 1) or UPS (lane 2) were fractionated on a SDS-PAGE and Coomassie stained. Western blots of protein prepared from cells infected with the baculoviruses containing vector alone (lane 3), UPS-derived MYC3-lox-RAD53 (lane 4), vector alone (lane 5), or UPS-derived HA3-lox-RAD53 (lane 6) were probed with anti-Myc (lanes 3–4) or anti-HA (lane 5–6) monoclonal antibodies.

In yet other examples, in mammals, the present invention demonstrated expression of a Myc-tagged F-box protein under the control of the CMV promoter when transfected into Hela cells as shown in FIG. 19. This figure shows immunoblotting of whole cell lysates with anti-HA antibodies. The cells used were Hela cells transfected by the calcium phosphate method with the CMV expression vectors pHM200-HA3 or pHM200-HA3-F3, expressing an HA-tagged F-box protein. In all, over 200 UPS derived constructs have been made and tested, showing expression success rates indistinguishable from those of conventional cloning methods.

EXAMPLE 6

Construction of an *E. coli* Strain That Inducibly Expresses Cre Recombinase

An *E. coli* strain containing a cre gene under the control of an inducible promoter, termed the QLB4 strain, was constructed as follows. The cre gene was placed under the transcriptional control of the inducible lac promoter by inserting the cre ORF into a derivative of pNN402 [Elledge et al. (1991) *Proc. Natl. Acad Sci. USA* 88:1731]; pNN402 was modified to contain a lac promoter. This construct was then crossed onto lambda phage (e.g., λgt11) using conventional techniques. The recombinant lambda phage carrying the lac-cre gene was integrated into the chromosome of *E. coli* strain JM1 07 to generate the QLB4 strain.

Figure 11:
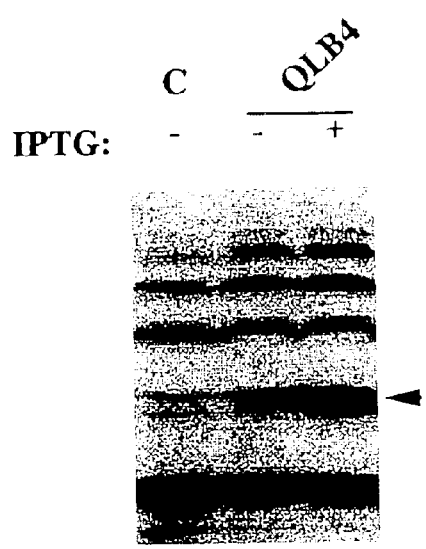
FIG. 11 shows a Western blot of an SDS-PAGE gel containing extracts prepared from *E. coli* cells (QLB4) containing either a conventionally constructed Gst-Skp1 plasmid or pGst-Skp1 (produced by an in vitro fusion reaction).

Expression of Cre recombinase was induced by growing QLB4 cells at 37° C. until an $OD_{600}$ of 0.6 was reached. The culture was then split into 2 parts and IPTG was added to one part to a final concentration of 0.4 mM. As a control, the BNN132 strain (ATCC 47059; Elledge et al. (1991), supra] which contains the cre gene under the transcriptional control of the endogenous cre promoter was treated as described for the QLB4 strain. Cell extracts (total protein) were prepared from all four samples (QLB4±IPTG and BNN132±IPTG) and examined for expression of Cre recombinase by Western blotting analysis. The Western blot was probed using a rabbit polyclonal anti-Cre antibody (Novagen) as the primary antibody and a goat anti-rabbit IgG horseradish peroxidase conjugate (Amersham) as the secondary antibody according to the manufacturer's instructions. FIG. 11 shows a Western blot containing extracts prepared from (shown left to right) BNN123 cells grown in the absence of IPTG ("C") and QLB4 cells grown in the absence ("QLB4−") and presence of IPTG ("QLB4+"), respectively. The location of the Cre recombinase band is indicated by the arrowhead. The additional bands seen on this Western blot are due to cross-reactivity of the crude (i.e., not affinity purified) rabbit anti-Cre antibody with bacterial proteins.

Western blot analysis demonstrated that Cre protein could not be detected in BNN123 cells grown in the presence or absence of IPTG. Cre protein was detected in QLB4 cells grown in the presence of IPTG, but not in the absence of IPTG, by Western blot analysis. Therefore, the expression of Cre recombinase in QLB4 cells is greatly induced by the presence of IPTG in the growth medium. By this analysis, the expression of Cre recombinase in QLB4 cells is dependent upon the induction of the lac-cre gene by IPTG. However, more sensitive functional assays indicate that the Cre protein was expressed constitutively at very low levels in both BNN132 cells and QLB4 cells in the absence of IPTG. In these functional assays, a pUNI vector ($Kn^R$) and a pHOST vector ($Ap^R$) were cotransformed into QLB4 cells and the transformed cells were grown on plates containing kanamycin to select for the presence of the pUNI-pHOST fusion plasmid. Plasmid DNA was isolated from individual kanamnycin-resistant colonies and subjected to restriction enzyme digestion to examine the structure of the plasmid DNA. This analysis revealed that multiple isoforms of the plasmid fusion product were present in the plasmid DNA isolated from any single kanarnycin-resistant colony. While not limiting the present invention to any particular mechanism, it is believed that low level constitutive expression of Cre recombinase leads to multiple fusion events between the pUNI and pHOST vectors resulting in the production of multimeric forms (i.e., trimer, tetramer, etc.) of the fused plasmid (the desired fused plasmid is a dimer formed by fusion of pUNI and pHOST). The multimeric plasmid fusion products would be expected to be unstable due to the fact that the Cre protein is constitutively expressed in QLB4 cells.

To overcome the potential problems that low level constitutive expression of the cre gene in the host cell may cause, the expression of cre can be more tightly controlled as described below. In addition to the approaches described below, the pUNI a nd pHOST vectors can b e modified as described in Example 7 and these modified vectors can be fused using a host cell that constitutively expresses the Cre protein.

The expression of Cre recombinase can be more tightly controlled by a variety of means. For example, the expression of the cre gene can be made conditional when expressing cre under the control of the lac promoter by growing the host cells in medium containing glucose. The presence of 0.2% glucose in the growth medium virtually shuts down transcription from the lac promoter. In addition, the lac promoter can be modified to insert additional operator (o) sites which bind the lac repressor. Other tightly controlled promoters are known to the art (e.g., the T7 promoter which requires the expression of T7 RNA polymerase; these promoters are available on the pET vectors (Novagen)) and may be employed to control the expression of the cre gene.

In addition to placing the cre ORF under the control of a tightly controlled promoter, Cre expression can be tightly controlled by placing the cre gene on a plasmid containing a temperature-sensitive (ts) replicon (e.g., rep $pSC101^{ts}$). When the cre gene is carried on a ts replication plasmid, Cre will be expressed during the transformation of the host cell (because the host cell containing the ts plasmid containing the cre gene was maintained at the permissive temperature) but will be absent following recombination of the prNI and pHOST vectors when the host cell is grown at a temperature non-permissive for replication of the ts replicon.

EXAMPLE 7

In Vivo Recombination in Prokaryotic Hosts Using the Univector Fusion System

As discussed above, Cre-loxP-mediated plasmid fusion can occur in vivo, although the reverse reaction, resolution of heterodimers, might decrease its utility. Ideally, it would be desirable to have Cre present only transiently to catalyze the initial fusion event, then absent to allow the stable propagation of the recombinant products. Therefore, a model was tested whereby UPS was explored in vivo in the *E. coli* stain BUN13 that conditionally expresses Cre recombinase under lac control and in a second strain carrying cre on a plasmid, pQL269, with a Ts origin of replication derived from pSC101. Experiments using BUN13 and co-transformation of pUNI-10 and pQL103, an $Ap^r$loxP containing plasmid, showed that the UPS reaction occurred efficiently, but many colonies had a mixture of plasmids that required retransformation into non-cre-expressing strain to stabilize. However, results with the Ts plasmid were better. Competent cells were prepared from JM107/pQL269 cells grown at 42° C. for several hours to cause loss of pQL269. Co-transformation of pUNI-10 and pQL103 into these cells followed by selection on kanamycin plates at 42° C. revealed that 25% contained the desired single pUNI-10-pQL103 co-integrant. These two experiments demonstrated that UPS can be used to generate plasmid fusions in vivo and provide an alternative to the in vitro reaction when Gst-Cre is not available.

As described in Example 6 and the experiments above, cotransformation of *E. coli* cells expressing Cre protein (e.g., QLB4, BNN 132) with a pUNI construct and a pHOST construct (each construct containing a single lox site) results in the fusion of these two constructs in vivo. If the host cell used for the recombination reaction constitutively expresses the Cre protein, multimeric forms of the fused constructs are generated. In addition to the methods outlined above for tightly regulating the expression of the cre gene in the host cell, cells constitutively producing Cre protein can be employed with modified pUNI and pHOST vectors as described in this example. The pUNI construct is modified such that two different lox sites flank the kanamycin resistance gene (the modified pUNI construct is termed pUNI-D). The two lox sites differ in their spacer regions by one or two nucleotides and for the sake of discussion the two different lox sites are referred to as "loxA" and "loxB" (e.g., loxP and loxP511; "loxB" is used in this discussion to distinguish it from the first lox site termed "loxA" and does not indicate the use of the loxB sequence found in the E. coli chromosome). Cre cannot efficiently catalyze a recombination event between a loxA site and a loxB due to the sequence changes located in the spacer regions between the Cre binding sites; however Cre can efficiently catalyze the recombination between two loxA sites or two loxB sites [Hoess et al. (1986) Nucleic Acids Res. 14:2287]. The pHOST construct is modified such that one loxA site and one loxB site flank the selectable marker gene (the modified pHOST construct is termed pHOST-D). In this example, pHOST contains the sacB gene as the selectable marker (a negative selectable marker). The presence of the sacB gene on pHOST-D provides a means of counter-selection as cells expressing the sacB gene are killed when the cell is grown in medium containing 5% sucrose [Gay et al. (1985) J. Bacteriol. 164:918 and (1983) J Bacteriol. 153:1424].

Figure 12:
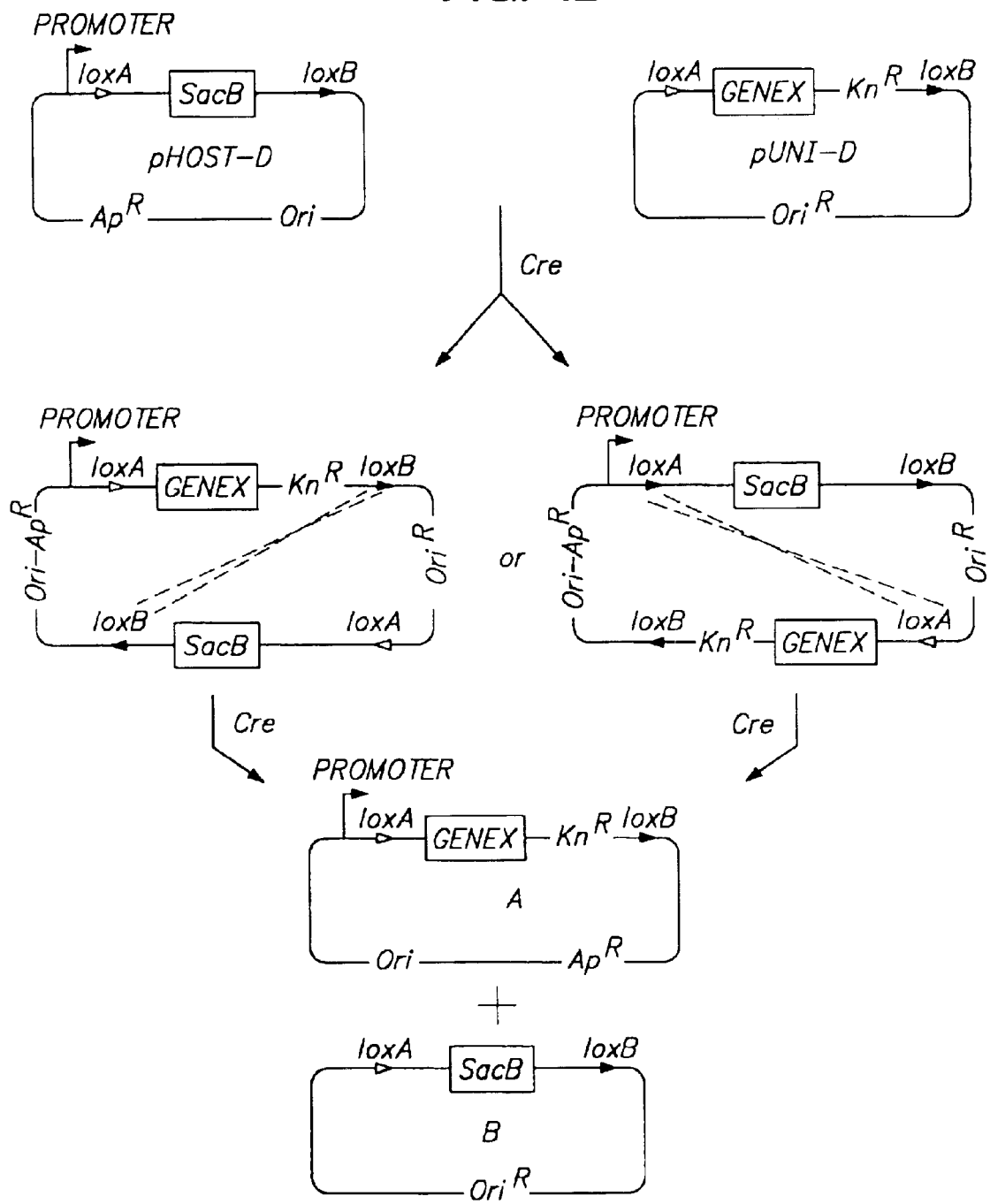
FIG. 12 provides a schematic illustrating the in vivo gene trap method for the recombination of lox-containing vectors in a host cell constitutively expressing the Cre protein.

FIG. 12 provides a schematic showing the strategy for in vivo recombination in a Cre-expressing host cell (e.g., QLB4 cells) using the pUNI-D and pHOST-D constructs. Arrows are used to indicate the direction of transcription of various genes or gene segments in FIG. 12. In FIG. 12, the following abbreviations are used: $Ap^R$ (ampicillin resistance gene); $Kn^R$ (kanamycin resistance gene); Ori (non-conditional plasmid origin of replication); $Ori^R$ (the R6Kγ conditional origin of replication); Cre (Cre recombinase); GENEX (gene of interest). The strategy outlined in FIG. 12 is referred to as the "in vivo gene-trap." FIG. 12 illustrates that the second lox site (loxB) in pUNI-D (relative to the design of the pUNI-10 vector) is inserted between the kanarnycin resistance gene and the R6Kγ conditional origin of replication.

To generate a pHOST-D construct, a commercially available expression vector containing the desired promoter (and optionally enhancer) is modified as described in Example 2 to insert the loxA site downstream of the promoter. However, it is not necessary that a commercially available expression vector be employed as the art is well aware of methods for the generation of expression vectors. Sequences encoding the sacB gene [Gay et al (1983) J Bacteriol. 153:1424; GenBank Accession Nos. X02730 and K01987] and the second lox site (loxB) are inserted downstream of the first lox site (loxA).

The pUNI-D and pHOST-D constructs are cotransformed into QLB4 cells (Example 6) and the transformed cells are plated onto LB/Ap/Kn plates containing 5% sucrose to select for the desired recombinant. FIG. 12 illustrates the recombination events that will occur in the presence of Cre in the QLB4 cells. First pUNI-D and pHOST-D will fuse to form two dimers in which two possible double cross-over events can occur. These two double cross-over events are diagrammed in FIG. 12. The double cross-over events will result in the exchange of the DNA segments that are flanked by loxA and loxB to produce the plasmids labelled "A" and "B." All plasmids that contain the sacB gene (the pHOST-D, the fused plasmids and plasmid B) will be selected against by the presence of sucrose in the growth medium. The pUNI-D construct will not be able to replicate in QLB4 cells as these cells do not express the II protein required for replication of the R6Kγ origin. Therefore, the only construct that will be maintained in QLB4 cells selected on LB/Kn containing sucrose is the desired plasmid A in which the gene of interest from pUNI-D has been placed under the transcriptional control of the promoter located on pHOST-D.

To illustrate this method, pUNI-10 was modified to place a second lox site, comprising the loxP511 sequence (SEQ ID NO:16) between the kanamycin resistance gene and the R6Kγ conditional origin of replication to create pUNI-10-D. A second lox site, comprising the loxP511 site, was inserted onto a loxP-containing expression plasmid (i.e., a pHOST vector) to create a pHOST-D vector. One-half of one microgram of each plasmid was cotransformed into competent QLB4 cells and an aliquot of the transformed cells were plated onto LB/Ap plates and onto LB/Ap/Kn plates containing 5% sucrose and the number of colonies on each type of plate were counted. The percentage of $Ap^R Kn^R$ colonies which grew on sucrose-containing plates relative to the number of $Ap^R$ colonies was 1% ($1 \times 10^3 / 1 \times 10^5$). Restriction enzyme digestion of plasmid DNA isolated from individual $Ap^R Kn^R$ colonies which grew on sucrose-containing plates confirmed that the desired fusions had been generated. These results indicate that the in vivo gene trap method can be used to recombine a gene of interest carried on a pUNI-D vector into an expression vector using host cells that constitutively express the Cre protein.

In addition to providing a means for recombining a gene of interest carried on a pUNI-D vector into an expression vector using host cells that constitutively express the Cre protein, the in vivo gene trap method provides a means to transfer a gene of interest contained on a linear DNA molecule (e.g., a PCR product) that lacks a selectable marker into an expression vector(s). The desired PCR product is amplified using two primers, each of which encode a different lox site (a "loxA" and "loxB" site such as a loxP and loxP511 site). A pUNI vector is constructed that contains (5' to 3') a loxA site, a counter-selectable marker such as the sacB gene and a loxB site (i.e., the two different lox sites flank the counter-selectable marker). This pUNI vector also contains a conditional origin of replication and an antibiotic resistance gene as described above and in Example 1. The PCR product (loxA-amplified sequence-loxB) is recombined with the modified pUNI vector (which comprises loxA-counter-selectable marker-loxB) to create a pUNI vector containing the PCR product which now lacks the counter-selectable marker. This recombination event is selected for by growing the host cells in medium that kills the host if the counter-selectable gene is expressed. The PCR product in the pUNI vector (containing 2 lox sites) can then be placed under the control of the desired promoter element by recombining the pUNI/PCR product construct with the appropriate pHOST-D vector.

EXAMPLE 8

The Use of Modified LoxP Sites to Increase Expression of the Protein of Interest The pUNI and pHOST constructs employed in the Univector Plasmid Fusion System were designed such that plasmid fusion resulted in the introduction of a lox site between the promoter and the gene of interest. LoxP sites consist of two 13 bp inverted repeats separated by an 8 bp spacer region [Hoess et al. (1982) Proc. Natl. Acad. Sci. USA 79:3398 and U.S. Pat. No. 4,959,317]. Transcripts of the gene of interest produced from a pUNI-pHOST fusion construct comprising a loxP site may have two 13 nucleotide perfect inverted repeats within the 5' untranslated region (UTR) that have the potential to form a stem-loop structure (this will occur in those cases where pHOST does not encode an affinity domain at the amino-terminus of the fusion protein). It is currently believed that the ribosome scanning mechanism is the most commonly used mechanism for initiation of translation in eukaryotes (e.g., yeast and mammalian cells). Using this mechanism, the ribosome binds to the 5' cap structure of the mRNA transcript and scans downstream along the 5' UTR searching for the first ATG or translation start codon. Without limiting the present invention to any particular mechanism, it is possible that a stem-loop structure formed by the presence of a loxP sequence on the 5' UTR of the mRNA encoding the protein of interest would block or reduce the efficiency of ribosome scanning and thus the translation initiation step could be impaired. There is evidence that stem-loop structures in the 5' UTR of particular mRNAs reduce the efficiency of translation in eukaryotes [see, e.g., Donahue et al. (1988) Mol. Cell. Biol. 8:2964 and Yoon et al. Genes and Dev. (1992) 6:2463]. It is noted that no evidence suggests that the presence of a stem-loop structure in the coding region (as opposed to the 5' UTR) of a transcript negatively affects its ability to be translated. It is likely that the energy of protein synthesis is sufficient to overcome secondary structures present in mRNAs. Indeed the data presented in Example 5 shows that a GST-SKP1 fusion construct produced using the Univector Fusion System (i.e., the construct contains a loxP site between the sequences encoding the Gst and Skp1 domains) produced the same level of fusion protein as did a conventional construct encoding a Gst-Skp1 fusion protein which lacks the loxP sequence. Therefore, concerns over the presence of a stem-loop structure caused by the presence of a lox sequence in a transcript encoded by a pUNI-pHOST fusion construct are limited to those constructs that do not generate fusion proteins.

If low levels of expression are observed when a gene of interest is expressed from a pUNI-pHOST fusion constructs comprising lox sequences that comprise perfect 13 bp inverted repeats (e.g., loxP), pUNI and pHOST constructs containing mutated loxP sequences are employed. The mutated loxP sequences comprise point mutations that create mismatches between the two 13 bp inverted repeat sequences within the loxP site that disrupt the formation of or reduce the stability of a stem loop structure. Specifically, two modified loxP sites were designed that have mismatches at different positions in the inverted repeats located within a loxP site. The 13 bp inverted repeats are binding sites for the Cre protein; thus, each loxP site has two binding sites for Cre. For the purpose of discussion, these two binding sites are referred to as L and R (left and right). The wild-type loxP site is designed L(0)-R(0) wherein "0" indicates the absence of a mutation (i.e., the wild-type sequence). Two derivatives of the wild-type loxP sequence were designed and termed loxP2 and loxP3. The sequence of loxP2 (SEQ ID NO:13), loxP3 (SEQ ID NO:14), as well as the wild-type loxP sequence (SEQ ID NO:12) are shown in FIG. 13. LoxP2 is placed on the pUNI-10 construct (in place of the wild-type loxP site) and loxP3 is placed on the pHOST construct.

LoxP2 has repeats designated L(3,6)-R(0) which indicates that the third and sixth nucleotides of the left repeat are mutated; thus, a mismatch is introduced at the third and sixth positions between the L and R repeats of the loxP2 site. LoxP3 has repeats designated L(0)-R(9) which indicates that the ninth nucleotide on the right repeat sequence is mutated to introduce a mismatch at the ninth position between the L and R repeats of the loxP3 site. Fusion between the loxP2 site on the pUNI construct and the loxP3 site on the pHOST construct will generate a hybrid loxP23 site [L(3,6)-R(9)] located between the promoter and the gene of interest and a wild-type loxP site [L(0)-R(O)] at the distal junction. Thus, the loxP23 site (SEQ ID NO:15) in the 5' UTR will have three mismatches distributed at positions 3, 6 and 9 between the 13 nucleotide inverted repeats which are expected to strongly destabilize the formation of the stem-loop structure. Other mutated loxP sequences suitable for disruption of the stem-loop structure will be apparent to those skilled in the art; therefore, the present invention is not limited to the use of the loxP2 and loxP3 sequences for the purpose of disrupting stem-loop formation on the 5' UTR of transcripts produced from pUNI-pHOST fusion constructs. The suitability of any pair of mutated lox sites for use in the Univector Fusion system may be tested by placing one member of the pair on a pUNI vector and the other member on a pHOST construct. The two modified vectors are then recombined in vitro as described in Example 4 and the fusion reaction mixture is used to transform E. coli cells and the transformed cells are plated on selective medium (e.g., on LB/Amp and LB/Kan plates) in order to determine the efficiency of recombination between the two mutated lox sites (Example 4). The efficiency of recombination between the two mutated lox sites is compared to the efficiency of recombination between two wild-type loxP sites. Any pair of two different mutant lox sites that recombines at a rate that is about 5% or greater than that observed using two loxP sites is a useful pair of mutated lox sites for use in avoiding the formation of a stem-loop structure on the 5' UTR of the mRNA transcribed from the pUNI/pHOST fusion construct.

A strategy as described above was employed to determine if the reduced expression observed with the SKP1 ORF under control of the GAL1 promoter as described in Example 5 could be improved with mutated lox sites. A series of lox sites designed to reduce the stability of the stem-loop were employed. These, together with a control scrambled site, loxS, were placed between the GAL1 promoter and the lacZ reporter gene and β-galactosidase expression was measured. Mutations that decreased stem-loop stability tended to express better and one mutant, loxP$^{L369}$, did not display any inhibitory effects. This mutant also retained 25% of the wild-type recombination efficiency and has been designated loxH (i.e., for host). The oligonucleotides used to generate the loxH site are based on the loxH sequence 5'-ATTACCTCATATAGCA TACATTATACGAAGTTAT-3' (SEQ ID NO:32). LoxH was further tested by using it to place MYC-RNR4 under GAL1 control and showed no translational interference, as shown in FIG. 17 (compare lanes 2, 3, and 4). LoxH's 25% recombinational efficiency is well within the range useful for UPS-mediated plasmid constructions. Thus, it is recommended that loxH be used in pHOST recipient vectors intended for transcriptional fusions to maximize expression, while loxP should be used for all other applications because of its higher recombination efficiency.

It will be apparent to those skilled in the art that a similar strategy can be employed for the modification of frt sites when the FLP recombinase is employed for the recombination event. The frt site, like lox sites, contains two 13 bp inverted repeats separated by an 8 bp spacer region.

EXAMPLE 9

Precise ORF Transfer (POT)

Figure 20:
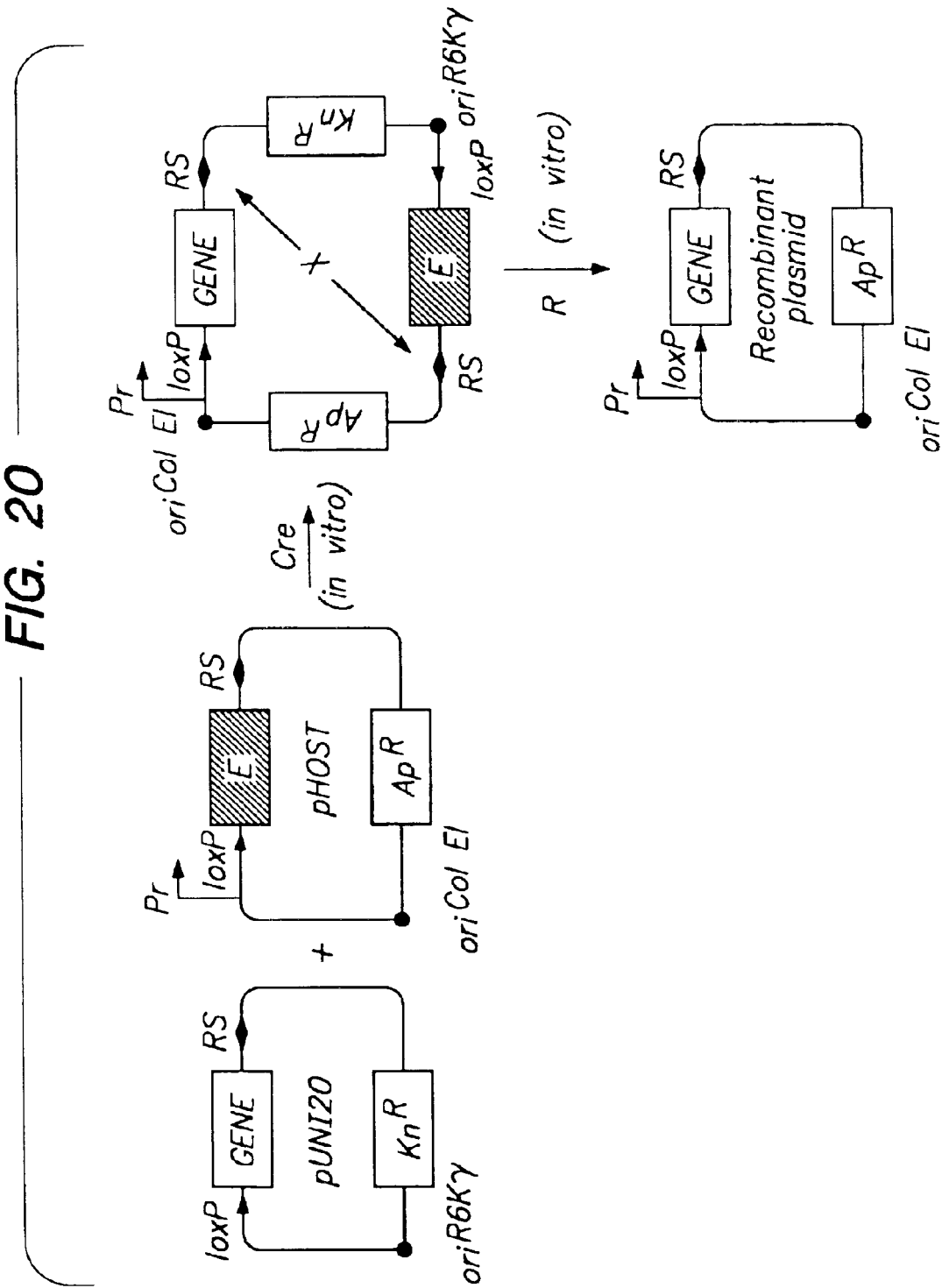
FIG. 20 shows a schematic representation of the POT reaction.

In order to transfer only the gene of interest from the Univector to the Host vector, the present invention provides a second recombination event that allows a resolution of the UPS generated heterodimer. A schematic representation of the POT reaction is shown in FIG. 20. In one embodiment of the present invention, a R-recombination site, RS, was placed after the cloning site in pUNI (i.e., pUNI-20) such that any gene inserted into pUNI-20 would be flanked on the 5' side by loxP and on the 3' side by RS, although the present invention contemplates the use of any other second recombination system (e.g., the Res system). Host recipient vectors must also contain lox and RS elements in the correct order. The initial fusion event is catalyzed go, by Cre by UPS. The second reaction can be catalyzed in vitro by incubation with purified R-recombinase (Araki et al., supra) or in vivo by transformation into a strain (e.g., BUN 15) expressing the R-recombinase under tac control on a Ts replication plasmid (e.g., pML66) that is lost when cells are plated at 42° C. POT works efficiently as a two step reaction in vivo or in vitro. Efficient resolution in vivo without a selection for the second recombination event requires incubation in LB plus IPTG after transformation prior to plating on selective media. An incubation of 1 h and 4 h gave 3% and 15% recombinants, respectively, which showed complete loss of the pUNI backbone through recombination between RS sequences. In vitro recombination catalyzed by the R recombinase achieved 30% recombinants.

The efficiency of recovering plasmids that have undergone POT can be greatly enhanced through the use of a recipient vector in which a counter-selectable marker is placed between the loxP and RS sites. For this purpose, the present invention utilized the $\Phi$X174 E gene which is toxic when expressed in $E. coli$ unless the host cell lacks the slyD gene [Maratea et al. (1985) $Gene$ 40:39]. pAS2-E, a two hybrid bait vector derived from pAS2 [Durfee et al. (1994) $Gene. \& Dev.$ 7:555] which contains in a 5' to 3' order loxP, E under control of the tac promoter, and an RS site, was fused with pUNI-20, containing the SKP1 gene and the co-integrant was selected by transformation into CX1 (slyD). This co-integrant was then transformed into BUN15 cells expressing the R recombinase and resolution events were isolated by selecting for Ap$^r$ in the presence of IPTG to induce the E protein. Since BUN15 is slyD$^{+/}$, $^{pAS}$2-E alone cannot survive in it because of toxicity due to E expression. However, when pAS2-E is fused to pUNI-20 derivatives, it can transform that strain because subsequent R-dependent site-specific recombination between RS sites will eliminate both the pUNI backbone and E. This results in the replacement of E with the corresponding region from pUNI. One hundred percent (24 of 24) Ap$^r$ transformants resulting from the transformation of the pAS2-E-pUNI-20-SKP1 fusion plasmid showed precise transfer of the SKP1 gene from pUNI-20 into pAS2-E with only 1 hr incubation prior to plating on selective media.

Transformation of a heterodimeric plasmid with E flanked by RS sites into BUN 15 gave a transformation several orders of magnitude greater than transformation of the pAS2-E plasmid itself. This demonstrated that POT can be achieved in a single step by direct transformation of a UPS reaction into BUN15 (i.e., rather than a two-step process). pUNI-20-SKP1 and pAS2-E were incubated with Gst-Cre in a standard UPS reaction and the reaction mixture was transformed directly into BUN 15 and AP$^r$ transformants were selected at 42° C. after an hour incubation. One hundred percent (20 of 20) of Ap$^r$ transformants were found to have undergone POT with SKP1 replacing the E gene in pAS2-E as determined by restriction digestion with PvuII, as shown in FIG. 21. The sample shown in FIG. 21 was generated from plasmid DNA isolated from 10 different Ap$^r$ transformants, digested as described above along with two parental plasmids, P1 (pUNI-20-SKP1) and P2 (pAS2-E) and I (the UPS generated pUNI-20-SKP1-pAS2-E recombination intermediate). Precise ORF transfer resulted in the generation of a novel 800 bp PvuII fragment indicated by the arrowhead.

For POT assays, BUN15 cells were grown overnight in LB containing spectinomycin (50 $\mu$g/ml) at 30° C. BUN15 cells were diluted 1 to 100 in fresh media LB/Spec media containing 0.3 mM IPTG and grown to OD of 0.5. Electrocompetent cells were prepared as recommended (Biorad). Forty $\mu$l of competent cells were used in each transformation. After the electrotransformation, cells were incubated in LB plus IPTG for 1–8 hr for recovery before being plated on LB/Amp/IPTG 1 mM and incubated at 42° C.

EXAMPLE 10

Library Transfer Using UPS

The ability to use the methods and compositions of the present invention for generating and subcloning entire nucleic acid libraries is demonstrated in this Example. A random shear $S. cerevisiae$ genomic library was made in pUNI- 10 using the XhoI-adaptor strategy [Elledge et al. (1991) $Proc. Natl. Acad Sci.$ 88:1731]. This library had 5×10$^5$ recombinants with 80% inserts ranging from 3 kb to 8 kb. This library was fused to pRS425-lox, a URA3 2 $\mu$ plasmid, using UPS and 1.6×10$^6$ recombinant fusion plasmids were recovered. This library was used to transform an $S. cerevisiae$ cdc4-1 mutant strain Y543 and Ura$^+$ transformants were selected at 34° C., the non-permissive temperature of cdc4-1. Of 31 plasmids capable of conferring growth at 34° C., three classes were recovered. One class was CDC4 as expected, the second was SKP1, and the third was CLB3. SKP1 and CLB4, a cyclin closely related to CLB3, had been previously shown to suppress cdc4-1 mutants when overexpressed from the GAL promoter [Bai et al. (1994) $EMBO$ $J.$ 3:6087; and Bai et al., supra]. These experiments demonstrate the feasibility of library transfer using UPS. In cases where a cDNA expression library is created, such as for the two hybrid system, once clones have been isolated, they can be rapidly converted back into simple Univector clones by Cre recombination in vivo. Using UPS, these plasmids can now be rapidly fused with any of a series of pHOST expression vectors for future analytical needs.

EXAMPLE 11

General Material and Methods

This Example provides general materials and methods used throughout the experiments discussed above and below.

I. Media, Enzymes, and Chemicals

For drug selections, LB plates or liquid media were supplemented with either kanamycin (40 $\mu$g/ml) or ampicillin (100 $\mu$g/ml). When necessary, isopropyl $\beta$-D-thiogalactoside (IPTG) was added to a final concentration of 0.3 mM and X-Gal (Sigma) was used at 80 $\mu$g/ml. Yeast growth media and plates were made according to Rose et al. [Rose et al. (1990) $Laboratory$ $course$ $manual$ $for$ $methods$ $in$ $yeast$ $genetics$, Cold Spring Harbor, N.Y., Cold Spring Harbor Laboratory Press]. Restriction endonucleases, large (klenow) fragment of $E. coli$ DNA polymerase I, T4 polynucleotide kinase, T4 DNA polymerase, T4 DNA ligase were purchased from New England Biolabs. Drugs were purchased from Sigma if not otherwise specified.

II. Bacterial and Yeast Strains

E. coli BW23474 [Δlac-169, robA1, creC510, hsdR514, uidA(ΔMluI)::pir-116, endA, recA1] and BW23473 [Δlac-169, robA1, creC510, hsdR514, uidA(ΔMluI)::pir+, endA, recA1] (Metcalf et al., supra) was a gift of B. Wanner and was used as host for propagation of all Univector based plasmids. BUN10 [hisG4 thr-1 leuB6 t lacY1kdgK51Δ(gpt-proA)62 rpsL31 tsx33 supE44 recB21 recC22 sbcA23 hsdR::cat-pir-116(Cm$^R$)] was used for homologous recombination experiments. BUN13 which has cre under the control of the lac promoter is JM107 lysogenized with $\lambda_{LC}$ (aadA lac-cre). BUN15 is XL1 blue containing pML66(tac-R, SP$^r$) and was used for the in vivo RS recombination assays. E. coli JM107 or DH5α [Sambrook et al. (1989) Molecular Cloning: A Laboratory Manual, Cold Spring Harbor Lab., Cold Spring Harbor, N.Y., 2nd Ed.] were the transformation recipients for all other plasmid construction, including those made by UPS. E. coil BL21 was used as the host for bacterial expression studies. CX1 (ara leu purE gal trp his argG rpsL thi-1 supE lacI$^Q$ slyD1) was used for propagation of E expression clones. S. cerevisiae Y80 [Zhou and Elledge (1992) Genetics 131:851] was used for yeast expression studies and Y543 (as Y80 but cdc4-1) was used for cdc4 suppression (Bai et al., 1994, supra).

III. Plasmid Construction

The construction of several of the plasmids used in the examples of the present invention are provided below. These examples are provided to illustrate strategies and general methods used in making plasmids for use in the UPS. However, these specific plasmids and methods of construction are not required to practice the present invention.

For the Gst-Cre expression construct, pQL123, the cre ORF was amplified by PCR and an NcoI site placed at the first ATG using primers
5'-CCATGGCCAATTTACTGACCGTACAC-3' (SEQ ID NO:21) and
5'-CCCGGGCTAATCGCCATCTTCCAGC-3' (SEQ ID NO:20). The PCR product was cloned into pCR™II (Invitrogen) and subcloned as a NcoI-EcoRI fragment into NcoI-EcoRI digested pGEX-2Tkcs to create pQL123.

The pHOST plasmid pQL 103 was made by deleting one loxP site from pSE1086, which contains a XhoI-loxP-Not1-loxP-SalI cassette, by digestion with NotI and SalI, filling in the ends with klenow and religation. The 590 bp NcoI-BamHI fragment containing the S. cerevisiae SKP1 ORF was subcloned from pCB149 into NcoI-BamHI-cut pUNI-10 to create pQL130(pUNI-SKP1).

A second subclone of SKP1 is pML73 which contains the same 5' end of SKP1 but an additional 800 bp of genomic DNA to the next BamHI site at the 3' end cloned into pUNI-20. pML73 was used for the POT experiments. An oligo linker containing loxP and flanked by NcoI and BamHI overhangs was made by annealing two oligos
5'-CATGGCTATAACTTCGTATAGCATACATTATACG AAGTTATG-3' (SEQ ID NO:22) and 5'-GATCCATAAC TTCGTATAATGTATGCTATACGAAGTTAT-3' (SEQ ID NO:23), and then ligating into NcoI and BamHI digested pGEX-2TKcs to create pHB2-GST. The MYC$_3$-RNR4 gene was subcloned from pMH176 [Huang and Elledge (1997) Mol. Cell. Biol. 17:6105] as a XhoI-SacI fragment into XhoI-SabI-cleaved pUNI-10 to create pQL248, or into SaiII-SacI digested pBAD104, a GAL1 expression vector to create the control lacking loxP. Two pBAD104 derived recipient vectors, pQL138 and pQL193, were constructed by insertion of either a wild type loxP or loxP$^{369}$ sequence into the polylinker using primer pairs:
5'-TCGAGACGTCATAACTTCGTATAGCATACATTATA CGAAGTTATGC-3' (SEQ ID NO:24) and
5'-GCCGCATAACTTCGTATAATGTATGCTATACGAT GTTATGACGTC-3' (SEQ ID NO:25) (pQL138), or
5'-CATGGCTATAACTTCGTATAGCATACATTATACG AAGTTATG-3' (SEQ ID NO:26) and
5'-GATCCATAACTTCGTATAATGTATGCTATACGAA GTTATAGC-3' (SEQ ID NO:27) (pQL193). Two GAL1:MYC$_3$-RNR4 constructs were made by UPS between pQL248 and pQL 138 or pQL 193.

For the construction of pQL269 (lac-cre aadA on a Ts pSC 101 ori), the EcoRI-PvuII fragment from pQL 114 containing aadA and the lac-cre gene fusion was ligated to a BglI (made blunt by T4 polymerase)-EcoRI fragment from pINT-ts [Hasan et al. (1994) Gene 150:51] containing the Ts replication origin and transformants were screened for Sp$^R$ and Ts growth at 42° C. A plasmid with those properties was designated pQL269.

pML66 was constructed by ligating the EcoRI-SalI (blunt) fragment containing the tac promoter driving the R recombinase from pNN115 (Araki et al., supra) into EcoRI-PstI (blunt) cleaved pQL269. This spectinomycin resistant plasmid expresses R protein in the presence of IPTG and is lost from cells grown at 42° C. because of a temperature sensitive replication mutation.

pUNI-Amp was made by placing the bla gene from pUC19 in place of the neo gene on pUNI-20 by generating a PCR product of bla and ligating that into MluI-NheI (blunt) cleaved pUNI-20. The subcloning of the triple MYC tag into pUNI-Amp was accomplished by PCR amplification of the 3xMYC tag present of pJBN48 by the primers MZL154,
5'-AAATTTCTCGAGGCTCTGAGCAAAAGCTCAT-3' (SEQ ID NO:28) and MZL155,
5'-TATATATAGCGGCCGCTTAATTAAGATCCTCCTC GGATA-3' (SEQ ID NO:29), followed by cleavage of the PCR product with XhoI and NotI and ligation into XhoI-NotI cleaved pUNI-Amp to generate pML74. Sequence of the PCR primers used to amplify the 3xMYC tag from pML74 for tagging the C-terminus of SKP1 by homologous recombination were primer A (MZL 160)
5'-CCAGAGGAGGAGGCTGCCATTAGGCGTG AAAATGAATGGGCTGAAGACCG TCTGAGCAAAAGCTCATTTC-3' (SEQ ID NO:30) and primer B (MZL161) 5'-GGATATAGTTCCTC-CTTTCAGC (SEQ ID NO:31).

pAS2-E was constructed by first placing a synthetic loxP site between the NcoI-SalI sites of pAS2 to make pAS2-lox, and then generating a E-containing fragment with the following features: 5' XhoI site, tac promoter driving E, SpeI site 3' and ligated the XhoI-SpeI fragment together with a SpeI-PstI synthetic RS fragment into XhoI-PstI cleaved pAS2-lox to make pAS2-E (pML71).

IV. β-galactosidase Assays

Yeast cells expressing the GAL1:lacZ reporter constructs containing different loxP sequences were grown at 30° C. to mid-log phase (OD$_{600}$=0.5–0.6) in SC-Ura media containing 2% raffinose, galactose was added to 2% final, and cells were incubated at 30° C. for two hours. β-galactosidase activities were measured as described by Zhou and Elledge (Zhou and Elledge, supra).

EXAMPLE 12

Construction of BUN13

This Example describes the construction of BUN13, a lambda lysogen with cre under lac control. pSE356 contains a cassette consisting of the Tn5 neo gene, the lac promoter, and a polylinker sequence surrounded by stretches of λ DNA sequence. pQL 114, the plasmid used to recombine the cre gene into λ, was constructed in two steps. First, the BamHI-HindIII (made blunt by T4 DNA polymerase) fragment containing the spectinomycin resistance gene aadA from pDPT270 [Taylor and Cohen (1979) J. Bacteriol 137:92] was subcloned into BamHI-SphI (made blunt by T4 DNA polymerase digested pSE356) to create pQL102, replacing neo with aadA. Secondly, a NotI site was engineered at the 5' end of the ribosomal binding site of the cre gene by PCR using primers 5'-GCGGCCGCTGAGTG TTAAATGTCCAATT-3' (SEQ ID NO:19) and 5'-CCCGGGCTAATCGCCATCTTCCAGC-3' (SEQ ID NO:20). The PCR product was cloned into pCR™II and subcloned as a NotI-EcoRI fragment into NotI-EcoRI digested pQL102 to create pQL114, placing cre under lac control adjacent to aadA and flanked by λ DNA sequence. λ$^{KC}$ (Elledge et al., supra) was amplified on JM107 containing pQL114 and the resulting phage lysate containing the desired recombinant λ$_{LC}$ phage was used to infect JM107. Sp$^r$Kn$^s$ lysogens were selected and tested for Cre expression and the ability to perform UPS. One strain with those properties was designated BUN13.

It is clear from the above that the present invention provides methods for the subcloning of nucleic acid molecules that permit the rapid transfer of a target nucleic acid sequence (e.g., a gene of interest) from nucleic acid molecule to another in vitro or in vivo without the need to rely upon restriction enzyme digestions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A composition comprising a glutathione-S-transferase-Cre-recombinase fusion polypeptide.

2. The composition of claim 1, wherein the polypeptide has an amino acid sequence according to SEQ ID NO: 11.

3. The composition of claim 1, wherein the composition comprises an enzyme activity with a Cre recombinase efficiency of about 16.8% per microgram of protein.

4. An isolated nucleic acid molecule comprising a coding region wherein the coding region encodes a glutathione-S-transferase-Cre-recombinase fusion polypeptide.

5. The nucleic acid molecule of claim 4, wherein the coding region comprises the nucleic acid sequence of SEQ ID NO:10.

6. The nucleic acid molecule of claim 4, wherein the isolated nucleic acid molecule is an expression vector.

7. The nucleic acid molecule of claim 4, wherein the coding region is operatively linked to a promoter effective to direct expression of a glutathione-S-transferase-Cre recombinase fusion polypeptide.

8. The nucleic acid molecule of claim 7, wherein the promoter is an inducible promoter.

9. The nucleic acid of claim 8, wherein the promoter is the tac promoter.

10. A host cell comprising the nucleic acid molecule of claim 4.

11. A host cell comprising the nucleic acid molecule of claim 7.

12. The host cell of claim 11, wherein the host cell expresses a Cre recombinase activity.

13. The host cell of claim 11, further defined as an *E. coli* cell.

14. A bacterial cell engineered to express a glutathione-S-transferase-Cre-recombinase fusion polypeptide.

15. The bacterial cell of claim 14, wherein the polypeptide has an amino acid sequence according to SEQ ID NO:11.

16. A method of producing a glutathione-S-transferase-Cre-recombinase fusion polypeptide comprising:

obtaining an expression vector comprising a coding region encoding a glutathione-S-transferase-Cre-recombinase fusion polypeptide operatively linked to a promoter;

transforming or transfecting the vector into a cell; and growing the cell under conditions effective to express a glutathione-S-transferase-Cre-recombinase fusion polypeptide.

17. The method of claim 16, further comprising isolating the glutathione-S-transferase-Cre-recombinase fusion polypeptide.

18. The method of claim 17, wherein isolating the polypeptide comprises glutathione affinity chromatography.

19. A method of recombining nucleic acid segments, wherein each segment comprises a lox site specific recombinase site, the method comprising contacting the nucleic acid segment with a glutathione-S-transferase-Cre-recombinase fusion polypeptide.

20. The method of claim 19, wherein the polypeptide has an amino acid sequence according to SEQ ID NO: 11.

21. A composition comprising a glutathione-S-transferase-Cre-recombinase fusion polypeptide and one or more nucleic acid molecules, wherein the nucleic acids comprise a site specific recombinase site.

22. The composition of claim 21, wherein at least one of said nucleic acid molecules comprises a lox recombination site upstream in a 5' to 3' orientation from an amino acid encoding region.

23. The composition of claim 21, wherein at least one of said nucleic acid molecules comprises a transcription regulatory element upstream in a 5' to 3' orientation of a lox recombinase site.

24. The composition of claim 22 wherein the lox recombinase site is a loxP, loxP2, loxP3, loxP23, loxP511, loxB, loxC2, loxL, loxR, loxΔ86, loxΔ117, or loxH site.

25. The composition of claim 23 wherein the lox recombinase site is a loxP, loxP2, loxP3, loxP23, loxP511, loxB, loxC2, loxL, loxR, loxΔ86, loxΔ117, or loxH site.

26. The composition of claim 22, wherein the amino acid encoding region is a member of a nucleic acid library.

* * * * *